United States Patent
Beard et al.

(10) Patent No.: US 9,926,264 B2
(45) Date of Patent: Mar. 27, 2018

(54) PHENYLCARBAMATE DERIVATIVES AS FORMYL PEPTIDE RECEPTOR MODULATORS

(71) Applicant: Allergan, Inc., Irvine, CA (US)

(72) Inventors: Richard L. Beard, Newport Beach, CA (US); Tien T. Duong, Rancho Santa Margarita, CA (US); Michael E. Garst, Newport Beach, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 15/034,793

(22) PCT Filed: Nov. 20, 2014

(86) PCT No.: PCT/US2014/066608
§ 371 (c)(1),
(2) Date: May 5, 2016

(87) PCT Pub. No.: WO2015/077451
PCT Pub. Date: May 28, 2015

(65) Prior Publication Data
US 2016/0272581 A1 Sep. 22, 2016

Related U.S. Application Data

(60) Provisional application No. 61/907,320, filed on Nov. 21, 2013.

(51) Int. Cl.
| | |
|---|---|
| *A61K 8/64* | (2006.01) |
| *C07C 271/28* | (2006.01) |
| *C07C 305/06* | (2006.01) |
| *C07C 307/06* | (2006.01) |
| *C07D 257/04* | (2006.01) |
| *C07F 9/40* | (2006.01) |
| *C07C 309/15* | (2006.01) |
| *C07C 305/12* | (2006.01) |
| *C07C 309/19* | (2006.01) |
| *C07F 9/38* | (2006.01) |

(52) U.S. Cl.
CPC .......... *C07C 271/28* (2013.01); *C07C 305/06* (2013.01); *C07C 305/12* (2013.01); *C07C 307/06* (2013.01); *C07C 309/15* (2013.01); *C07C 309/19* (2013.01); *C07D 257/04* (2013.01); *C07F 9/38* (2013.01); *C07F 9/4006* (2013.01)

(58) Field of Classification Search
USPC ...................... 514/1.3, 1.1, 21.91
See application file for complete search history.

(56) References Cited

U.S. PATENT DOCUMENTS

| | | | | |
|---|---|---|---|---|
| 6,495,522 B1 * | 12/2002 | Wang | ................... | C07C 271/12 435/1.1 |
| 2013/0109866 A1 | 5/2013 | Beard et al. | | |
| 2013/0274230 A1 | 10/2013 | Beard et al. | | |
| 2015/0291511 A1 | 12/2015 | Beard et al. | | |

FOREIGN PATENT DOCUMENTS

| | | |
|---|---|---|
| WO | WO0116093 | 3/2001 |
| WO | WO2012074785 | 6/2012 |
| WO | WO2012109544 | 8/2012 |
| WO | WO2013062947 | 5/2013 |
| WO | WO2013070600 | 5/2013 |
| WO | WO2013071203 | 5/2013 |
| WO | WO2013122953 | 8/2013 |
| WO | WO2013158597 | 10/2013 |
| WO | WO2015009545 | 1/2015 |
| WO | 2015-116566 | 8/2015 |
| WO | 2015-116574 | 8/2015 |
| WO | WO2015179707 | 11/2015 |

OTHER PUBLICATIONS

Chiang, Nan, et al., The Lipoxin Receptor ALX: Potent Ligand-Specific and Stereoselective Actions in Vivo, Pharmacological Reviews, 2006, 463-487, 58, No. 3.
Cross, LC, Rules for the Nomenclature of Organic Chemistry Section E: Sterochemistry, Pure & Appl. Chem., 1976, 11-30, 45.
Dufton, Neil et al., Anti-Inflammatory Role of Murine Formyl-Peptide Receptor 2:Ligand-Specific Effects on Leukocyte Responses and Experimental Inflammation, The Journal of Immunology, Jan. 2010, pp. 2611-2619, 184, The American Association of Immunologist, Inc., Bethesda, MD.
Gavins, Felicity N., et al., Leukocyte recruitment in the brain in sepsis: involvement of the annexin 1-FPR2/ALX anti-inflammatory system, FASEB J., Sep. 10, 2012, 4977-4989, 26.
Gronert, Karsten, Lipoxins in the eye and their role in wound healing, Prostaglandins, Leukotrienes and Essential Fatty Acids, 2005, pp. 221-229, 73, Elsevier Ltd.
Gronert, Karston, et al., A Role for the Mouse 12/15-Lipoxygenase Pathway in Promoting Epithelial Wound Healing and Host Defense, The Journal of Biological Chemistry, 2005, pp. 15267-15278, 280, No. 15.
Leedom, Alexander J., et al., Endogenous LXA4 Circuits Are Determinants of Pathological Angiogenesis in Response to Chronic Injury, The American Journal of Pathology, Jan. 2010, pp. 74-84, 176, No. 1, American Society for Investigative Pathology.
Leoni, Giovanna, et al., Annexin A1, formyl peptide receptor, and NOX1 orchestrate ephithelial repair, The Journal of Clinical Investigation, 2013, 443-54, 123.
Maderna. Paola, et al., FPR2/ALX receptor expression and internalization are critical for lipoxin A4 and annexin-derived peptide-stimulated phagocytosis, FASEB J., Nov. 2010, 4240-4249, 24 (11).
Medeiros, Rodrigo, et al., Molecular Mechanisms of Topical Anti-Inflammatory Effects of Lipoxin A4 in Endotoxi-Induced Uveitis, Molecular Pharmacology, 2008, pp. 154-161, 74.

(Continued)

*Primary Examiner* — Pancham Bakshi
(74) *Attorney, Agent, or Firm* — Barbara C. Potts

(57) ABSTRACT

The present invention relates to N-phenyl carbamate derivatives, processes for preparing them, pharmaceutical compositions containing them and their use as pharmaceuticals as modulators of the N-formyl peptide 2 receptor.

10 Claims, 1 Drawing Sheet

(56) References Cited

OTHER PUBLICATIONS

Patent Cooperation Treaty, Notification of Transmittal of The International Search Report and The Written Opinion of the International Searching Authority, or the Declaration, PCT/US2014/066608, Feb. 10, 2015, pp. 1-9.

Perretti, Mauro et al, Therapeutic Anti-Inflammatory Potential of Formyl-Peptide Receptor Agonists, Pharmacology & Research, 2010, 175-188, 127.

Reville, Keira, et al., Lipoxin A4 Redistributes Myosin IIA and Cdc42 in Macrophages: Implications for Phagocytosis of Apoptotic Leukocytes, The Journal of Immunology, 2006, pp. 1878-1888, 176.

Serhan, Charles N., Resolution Phase of Inflammation: Novel Endogenous Anti-Inflammatory and Proresolving Lipid Mediators and Pathways, The Annual Reviews of Immunology, 2007, pp. 101-137, 25, Annual reviews.

Stahl, Heinrich et al, Handbook of Pharmaceutical Salts, Verlag Helvetica Chimica Acta—Zurich, 2002, 329-345.

Takano, Tomoko, et al., Aspirin-triggered 15-Epi-Lipoxin-A4 (LXa4) and LXA4 Stable Analogues Are Potent Inbitiors of Acute Inflammation: Evidence for Anti-inflammatory Receptors, Journal of Experimental Medicine, May 5, 1997, 1693-1704, 185, No. 9, The Rockerfeller University Press.

Tsuruki, Takahiro, et al., Mechanism of the Protective Effect of Intraperitoneally Administered Agonists for Formyl Peptide Receptors against Chemotherapy-Induced Alpecia, Bioscience, Biotechnology & Biochemistry, 2007, pp. 1198-1202, 71, No. 5.

Yamasaki, Kenshi et al., Increased serine protease activity and cathelicidin promotes skin inflammation in rosacea, Nature Medicine, Aug. 2007, pp. 975-980, vol. 13, No. 8, Nature Publishing Group.

\* cited by examiner

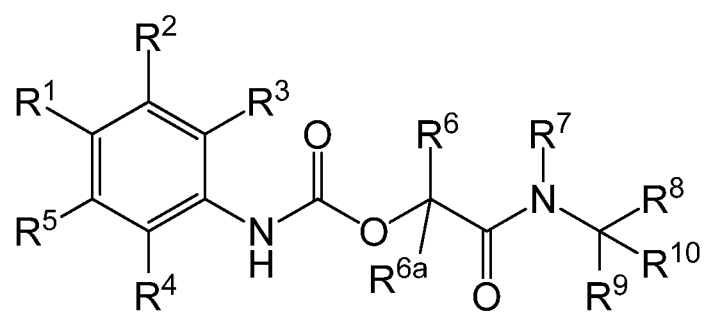
Formula I

PHENYLCARBAMATE DERIVATIVES AS FORMYL PEPTIDE RECEPTOR MODULATORS

CROSS-REFERENCE TO RELATED APPLICATIONS

This application is a national stage application under 35 U.S.C. § 371 PCT patent application PCT/US2014/066608, filed on Nov. 20, 2014, which claims the benefit of U.S. Provisional Patent Application Ser. No. 61/907,320, filed on Nov. 21, 2013, the entire contents of which is incorporated herein by this specific reference.

FIELD OF THE INVENTION

The present invention relates to N-phenyl carbamate derivatives, processes for preparing them, pharmaceutical compositions containing them and their use as pharmaceuticals as modulators of the N-formyl peptide 2 receptor (FPR2). The invention relates specifically to the use of these compounds and their pharmaceutical compositions to treat disorders associated with the FPR2 modulation.

BACKGROUND OF THE INVENTION

The formyl peptide receptor (FPR) family belongs to the seven transmembrane domain G-protein-coupled receptor (GPCR) family. This family includes 3 members in humans, and one member of this family, FPR2 (also known as FPRL-1, ALXA4), is expressed predominantly on inflammatory cells such as monocytes and neutrophils, as well as on T cells, and has been shown to play a critical role in leukocyte trafficking during inflammation and human pathology (Chiang N, Serhan C N, Dahlen, S, Drazen J M, Hay D W P, Rovati E, Shimizu T, Yokomizo T, Brink, C. The lipoxin receptor ALX: Potent ligand-specific and stereoselective actions in vivo. Pharmacological Reviews 2006; 58: 463-519). FPR2 is an exceptionally promiscuous receptor that responds to a menagerie of structurally diverse exogenous and endogenous ligands, including serum amyloid A (SAA), chemokine variant sCKβ8-1, the neuroprotective peptide humanin, anti-inflammatory eicosanoid lipoxin A4 (LXA4) and glucocorticoid-modulated protein annexin A1 (Chiang N, Serhan C N, Dahlen, S, Drazen J M, Hay D W P, Rovati E, Shimizu T, Yokomizo T, Brink, C. The lipoxin receptor ALX: Potent ligand-specific and stereoselective actions in vivo. Pharmacological Reviews 2006; 58: 463-519). FPR2 has been shown to transduce anti-inflammatory effects of arachidonic acid derived Lipoxin A4 (LXA4) in many systems, and has been shown to play a key role in the resolution of inflammation (Dufton N, Perretti M. Therapeutic anti-inflammatory potential of formyl peptide receptor agonists. Pharmacology & Therapeutics 2010; 127: 175-188). FPR2 knockout mice show exaggerated inflammation in disease conditions as expected by the biological role of the receptor (Dufton N, Hannon R, Brancaleone V, Dalli J, Patel H B, Gray M, D'Aquisto F, Buckingham J C, Perretti M, Flower R J. Anti-inflammatory role of the murine formyl-peptide receptor 2: Ligand-specific effects on leukocyte responses and experimental inflammation. Journal of Immunology 2010; 184: 2611-2619. Gavins FNE, Hughes E L, Buss N A P S, Holloway P M, Getting S J, Buckingham J C. Leukocyte recruitment in the brain in sepsis: involvement of the annexin1 FPR2/ALX anti-inflammatory system. FASEB 2012; 26: 1-13).

Activation of FPR2 by lipoxin A4 or its analogs and by Annexin I protein has been shown to result in anti-inflammatory activity by promoting active resolution of inflammation which involves inhibition of polymorphonuclear neutrophils (PMNs) and eosinophils migration and also stimulating monocyte migration enabling clearance of apoptotic cells from the site of inflammation in a nonphlogistic manner (Gavins F N E, Hughes E L, Buss N A P S, Holloway P M, Getting S J, Buckingham J C. Leukocyte recruitment in the brain in sepsis: involvement of the annexin1 FPR2/ALX anti-inflammatory system. FASEB 2012; 26: 1-13, Madema P, Cottell D C, Toivonen T, Dufton N, Dalli J, Perretti M, Godson C. FPR2/ALX receptor expression and internalization are critical for lipoxin A4 and annexin-derived peptide-stimulated phagocytosis. FASEB 2010; 24: 4240-4249). In addition, FPR2 has been shown to inhibit natural killer (NK) cytotoxicity and promote activation of T cells which further contributes to down regulation of tissue damaging inflammatory signals.

FPR2 interaction with LXA4 and Annexin has been shown to be beneficial in experimental models of dermal inflammation, angiogenesis, epithelial migration, edema, alopecia, ischemia reperfusion and ocular inflammation, such as endotoxin-induced uveitis and corneal wound healing. (Reville K, Cream J K, Vivers S, Dransfield I, Godson C. Lipoxin A4 redistributes Myosin IIA and Cdc42 in macrophages: Implications for phagocytosis of apoptotic leukocytes. Journal of Immunology 2006; 176: 1878-1888; Serhan C. Resolution phase of inflammation: Novel endogenous anti-inflammatory and proresolving lipid mediators and pathways. Annual reviews of Immunology 2007; 25: 101-137; Medeiros R, Rodrigues G B, Figueiredo C P, Rodrigues E B, Grumman A Jr, Menezes-de-Lima O Jr, Passos G F, Calixto J B. Molecular mechanisms of topical anti-inflammatory effects of lipoxin A(4) in endotoxin-induced uveitis. *Molecular Pharmacology* 2008; 74: 154-161; Gronert K, Maheshwari N, Khan N, Hassan I R, Dunn M, Schwartzmann M L. A role for the mouse 12/15-lipoxygenase pathways in promoting epithelial wound healing and host defense. Journal of Biological Chemistry 2005; 280: 15267-15278; Gronert K. Lipoxins in the eye and their role in wound healing. *Prostaglandins, Leukotrienes and Essential fatty Acids*. 2005; 73: 221-229); Takano T, Fiore S, Maddox J F, Brady H R, Petasis N A, Serhan C N. Aspirin-triggered 15-epi-lipoxin A4 and LXA4 stable analogues are potent inhibitors of acute inflammation: evidence for anti-inflammatory receptors. Journal of Experimental Medicine 1997; 185: 1693-1704; Leoni G, Alam A, Neumann P A, Lambeth J D, Cheng G, McCoy J, Hilgarth R S, Kundu K, Murthy N, Kusters D, Reutelingsperger C, Perretti M, Parkos C A, Neish A S, Nusrat A. Annexin A1, formyl peptide receptor, and NOX1 orchestrate epithelial repair. Journal of Clinical Investigation. 2013; 123:443-54; Leedom A, Sullivan A B, Dong B, Lau D, Gronert K. Endogenous LXA4 circuits are determinants of pathological angiogenesis in response to chronic injury. American Journal of Pathology 2010; 176: 74-84; Tsuruki T, Takahata K, Yoshikawa M. Mechanism of the protective effect of intraperitoneally administered agonists for formyl peptide receptors against chemotherapy-induced alopecia. Biosci Biotechnology Biochemistry. 2007; 71:1198-202).

Pharmaceutical utility of lipoxin A4 and its analogs are hampered by inherent physicochemical properties of the natural poly-olefinic natural product. Therefore, small molecule anti-inflammatory agonists of FPR2 would have a wide variety of therapeutic benefit in inflammatory disorders, including inflammatory disorders in the eye. Targeting FPR2 selectively would also have benefits of reduced side effects as compared to more broad acting anti-inflammatories such as steroids or NSAIDs which have significant side effects of elevated IOP and delays in wound healing in the eye. FPR2 is also expressed in ocular tissues in the cornea and also the posterior of eye, in addition to the inflammatory cells that migrate into the ocular tissues.

Targeting FPR2 selectively would also have benefits in skin wound healing given its potent anti-inflammatory and pro-epithelial repair role. In addition, some skin diseases have been shown to have an abnormal expression of LL37, a pro-inflammatory cathelicidin which has been shown to be a natural ligand of FPR2. In the chronic inflammatory disease rosacea, LL37 is highly expressed and is believed to play a key role in the pathogenesis (Yamasaki K, Di Nardo A, Bardan A, Murakami M, Ohtake T, Coda A, Dorschner R A, Bonnart C, Descargues P, Hovnanian A, Morhenn V B, Gallo R L. Increased serine protease activity and cathelicidin promotes skin inflammation in rosacea. Nature Medicine. 2007; 13:975-80).

FPR2 thus represents an important novel pro-resolutionary molecular target for the development of new therapeutic agents in diseases or conditions with excessive inflammatory responses.

SUMMARY OF THE INVENTION

A group of N-phenyl carbamate derivatives, which are potent and selective FPR2 modulators, has been discovered. As such, the compounds described herein are useful in treating a wide variety of disorders associated with modulation of FPR2 receptor. The term "modulator" as used herein, includes but is not limited to: receptor agonist, antagonist, inverse agonist, inverse antagonist, partial agonist, and partial antagonist.

This invention describes compounds of Formula I, which have FPR2 receptor biological activity. The compounds in accordance with the present invention are thus of use in medicine, for example in the treatment of humans with diseases and conditions that are alleviated by FPR2 modulation.

In one aspect, the invention provides a compound represented by Formula I:

Formula I wherein:

$R^1$ is optionally substituted $C_{1-8}$ alkyl, optionally substituted $C_{3-8}$ cycloalkyl, optionally substituted heterocycle, optionally substituted $C_{6-10}$ aryl, optionally substituted $C_{3-8}$ cycloalkenyl, halogen, $NR^{11}R^{12}$, fluorinated $C_{1-8}$ alkyl, perfluorinated $C_{1-8}$ alkyl, —S(O)$_m$R$^{13}$, —C(O)R$^{14}$ or —OR$^{15}$;

$R^2$ is H, optionally substituted $C_{1-8}$ alkyl, optionally substituted $C_{3-8}$ cycloalkyl, optionally substituted heterocycle, optionally substituted $C_{6-10}$ aryl, optionally substituted $C_{3-8}$ cycloalkenyl, halogen, $NR^{11}R^{12}$, fluorinated $C_{1-8}$ alkyl, perfluorinated $C_{1-8}$ alkyl, —S(O)$_m$R$^{13}$—C(O)R$^{14}$ or —OR$^{15}$;

$R^3$ is H, optionally substituted $C_{1-8}$ alkyl, optionally substituted $C_{3-8}$ cycloalkyl, optionally substituted heterocycle, optionally substituted $C_{6-10}$ aryl, optionally substituted $C_{3-8}$ cycloalkenyl, halogen, $NR^{11}R^{12}$, fluorinated $C_{1-8}$ alkyl, perfluorinated $C_{1-8}$ alkyl, —S(O)$_m$R$^{13}$—C(O)R$^{14}$ or —OR$^{15}$;

$R^4$ is H, optionally substituted $C_{1-8}$ alkyl, optionally substituted $C_{3-8}$ cycloalkyl, optionally substituted heterocycle, optionally substituted $C_{6-10}$ aryl, optionally substituted $C_{3-8}$ cycloalkenyl, halogen, $NR^{11}R^{12}$, fluorinated $C_{1-8}$ alkyl, perfluorinated $C_{1-8}$ alkyl, —S(O)$_m$R$^{13}$—C(O)R$^{14}$ or —OR$^{15}$;

$R^5$ is H, optionally substituted $C_{1-8}$ alkyl, optionally substituted $C_{3-8}$ cycloalkyl, optionally substituted heterocycle, optionally substituted $C_{6-10}$ aryl, optionally substituted $C_{3-8}$ cycloalkenyl, halogen, $NR^{11}R^{12}$, fluorinated $C_{1-8}$ alkyl, perfluorinated $C_{1-8}$ alkyl, —S(O)$_m$R$^{13}$—C(O)R$^{14}$ or —OR$^{15}$;

$R^6$ is H, optionally substituted $C_{1-8}$ alkyl, optionally substituted heterocycle, —(CH$_2$)$_p$COOH, —(CH$_2$)$_p$—NH$_2$, —(CH$_2$)$_p$—OH, —(CH$_2$)$_p$—SH, —(CH$_2$)$_p$—CONH$_2$, —(CH$_2$)$_p$—CONH$_2$, —CH(OH)CH$_3$, —(CH$_2$)$_p$SCH$_3$, —(CH$_2$)$_p$NH—C(=NH)(NH$_2$) or —CH$_2$C$_{6-10}$ aryl, wherein said —C$_{6-10}$ aryl is optionally substituted;

$R^{6a}$ is H or optionally substituted $C_{1-8}$ alkyl;

$R^7$ is H or optionally substituted $C_{1-8}$ alkyl;

$R^8$ is H;

$R^9$ is H, optionally substituted $C_{1-8}$ alkyl, optionally substituted $C_{3-8}$ cycloalkyl, optionally substituted heterocycle, optionally substituted $C_{6-10}$ aryl or optionally substituted $C_{3-8}$ cycloalkenyl;

$R^{10}$ is —(CH$_2$)$_n$OR$^{16}$, —(CH$_2$)$_n$S(O)$_2$OH, —(CH$_2$)$_n$C(O)R$^{17}$, —(CH$_2$)$_n$OS(O)$_2$OH, —(CH$_2$)$_n$NR$^{18}$R$^{19}$, —(CH$_2$)$_n$P(O)(OC$_{1-6}$ alkyl)$_2$, —(CH$_2$)$_n$P(O)(OC$_{1-6}$ alkyl)OH, —(CH$_2$)$_n$—P(O)(OH)$_2$ or optionally substituted heterocycle;

$R^{11}$ is H, optionally substituted $C_{1-8}$ alkyl, optionally substituted $C_{3-8}$ cycloalkyl, optionally substituted heterocycle, optionally substituted $C_{6-10}$ aryl or optionally substituted $C_{3-8}$ cycloalkenyl;

$R^{12}$ is H, optionally substituted $C_{1-8}$ alkyl, optionally substituted $C_{3-8}$ cycloalkyl, optionally substituted heterocycle, optionally substituted $C_{6-10}$ aryl or optionally substituted $C_{3-8}$ cycloalkenyl;

$R^{13}$ is H, optionally substituted $C_{1-8}$ alkyl, optionally substituted $C_{3-8}$ cycloalkyl, optionally substituted heterocycle, optionally substituted $C_{6-10}$ aryl, OH or optionally substituted $C_{3-8}$ cycloalkenyl;

$R^{14}$ is optionally substituted $C_{1-8}$ alkyl, optionally substituted $C_{3-8}$ cycloalkyl, optionally substituted heterocycle, optionally substituted $C_{6-10}$ aryl, optionally substituted $C_{3-8}$ cycloalkenyl or —OR$^{15}$;

$R^{15}$ is H or optionally substituted $C_{1-8}$ alkyl;

$R^{16}$ is H, —C(O)(C$_{1-8}$ alkyl) or optionally substituted $C_{1-8}$ alkyl;

$R^{17}$ is OH, —OC$_{1-8}$ alkyl or $C_{1-8}$ alkyl;

$R^{18}$ is selected from the group consisting of H, optionally substituted $C_{1-8}$ alkyl, optionally substituted $C_{3-8}$ cycloalkyl, optionally substituted heterocycle, optionally substituted $C_{6-10}$ aryl, optionally substituted $C_{3-8}$ cycloalkenyl, —C(O)R$^{17}$ and —S(O)$_2$N(C$_{1-8}$ alkyl)$_2$;

$R^{19}$ is selected from the group consisting of H, optionally substituted $C_{1-8}$ alkyl, optionally substituted $C_{3-8}$ cycloalkyl, optionally substituted heterocycle, optionally substituted $C_{6-10}$ aryl, or optionally substituted $C_{3-8}$ cycloalkenyl, —C(O)R$^{17}$ and —S(O)$_2$N(C$_{1-8}$ alkyl)$_2$;

p is 1, 2 or 3;

n is 0, 1, 2, 3, 4, 5, 6, 7 or 8; and m is 0, 1 or 2;

wherein each $C_{1-8}$ alkyl substituent is independently selected from the group consisting of halogen, hydroxyl, —$OC_{1-8}$alkyl, $C_{3-8}$cycloalkyl, amino, heterocycle, $C_{6-10}$aryl, carboxylic acid, phosphonic acid, sulphonic acid, phosphoric acid, nitro, amide, sulfonamide, carboxylate ester and ketone;

each $C_{3-8}$ cycloalkyl substituent is independently selected from the group consisting of halogen, hydroxyl, sulfonyl $C_{1-8}$ alkyl, sulfoxide $C_{1-8}$ alkyl, sulfonamide, nitro, —$OC_{1-8}$ alkyl, —$SC_{1-8}$ alkyl groups, —$C_{1-8}$ alkyl, ketone, alkylamino, amino, $C_{6-10}$ aryl and $C_{3-8}$ cycloalkyl;

each heterocycle substituent is independently selected from the group consisting of halogen, hydroxyl, —$OC_{1-8}$ alkyl, sulfonyl $C_{1-8}$ alkyl, sulfoxide $C_{1-8}$ alkyl, nitro, —$SC_{1-8}$ alkyl, —$C_{1-6}$ alkyl, ketone, alkylamino, amino, $C_{6-10}$ aryl and $C_{3-8}$ cycloalkyl;

each $C_{6-10}$ aryl substituent is independently selected from the group consisting of halogen, hydroxyl, sulfonyl $C_{1-8}$ alkyl, sulfoxide $C_{1-8}$ alkyl, sulfonamide, carboxylic acid, $C_{1-8}$ alkyl carboxylate (ester), amide, nitro, —$OC_{1-6}$ alkyl, —$SC_{1-8}$ alkyl, —$C_{1-8}$ alkyl, ketone, alkylamino, amino and $C_{3-8}$ cycloalkyl; and each $C_{3-8}$ cycloalkenyl substituent is independently selected from the group consisting of halogen, hydroxyl, sulfonyl $C_{1-8}$ alkyl, sulfoxide $C_{1-8}$ alkyl, nitro, —$OC_{1-6}$ alkyl, —$SC_{1-6}$ alkyl, —$C_{1-8}$ alkyl, ketone, alkylamino, amino, $C_{6-10}$ aryl and $C_{3-8}$ cycloalkyl;

or an enantiomer, diastereomer or tautomer thereof;

or a pharmaceutically acceptable salt of any of the foregoing.

The invention further provides for a compound selected from the group consisting of:

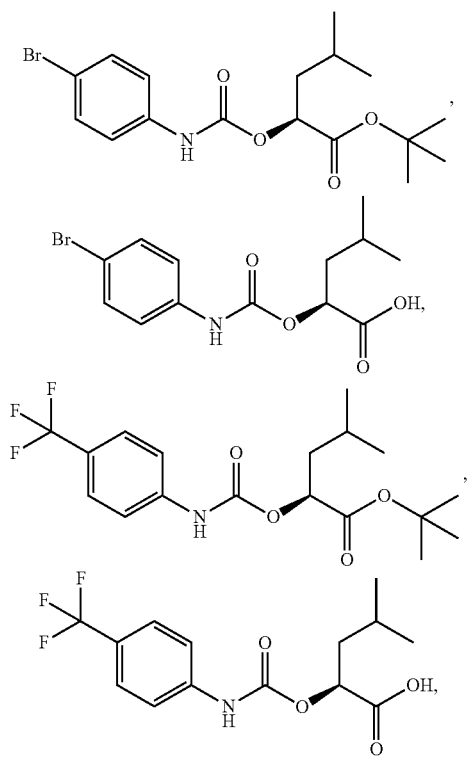

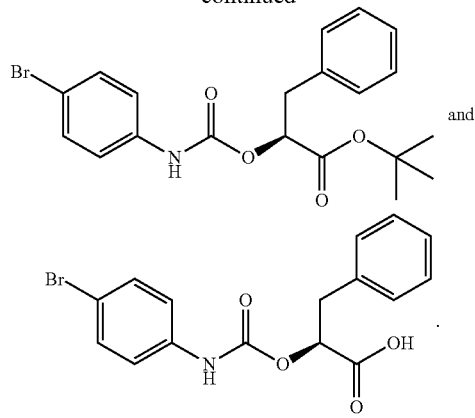

The term "alkyl", as used herein, refers to saturated, monovalent or divalent hydrocarbon moieties having linear or branched moieties or combinations thereof and containing 1 to 8 carbon atoms; one methylene (—$CH_2$—) group of the alkyl group can be replaced by oxygen, sulfur, sulfoxide, —N($R^x$)— (wherein $R^x$ is H, OH, or optionally substituted $C_{1-8}$ alkyl), carbonyl, carboxyl, sulfonyl, sulfate, sulfonate, amide, sulfonamide, by a divalent $C_{3-8}$ cycloalkyl, by a divalent heterocycle, or by a divalent aryl group. Alkyl groups can have one or more chiral centers. Alkyl groups can be independently substituted with one or more halogen atoms, hydroxyl groups, —$OC_{1-8}$ alkyl groups, cycloalkyl groups, amino groups, heterocyclic groups, aryl groups, carboxylic acid groups, phosphonic acid groups, sulphonic acid groups, phosphoric acid groups, nitro groups, amide groups, sulfonamide groups, ester groups, and/or ketone groups.

The term "cycloalkyl", as used herein, refers to a monovalent or divalent group of 3 to 8 carbon atoms derived from a saturated cyclic hydrocarbon. Cycloalkyl groups can be monocyclic or polycyclic. Cycloalkyl can be independently substituted with one or more halogen atoms, sulfonyl $C_{1-8}$ alkyl groups, sulfoxide $C_{1-8}$ alkyl groups, sulfonamide groups, nitro groups, —$OC_{1-8}$ alkyl groups, —$SC_{1-8}$ alkyl groups, —$C_{1-8}$ alkyl groups, ketone groups, alkylamino groups, amino groups, aryl groups, $C_{3-8}$ cycloalkyl groups and/or hydroxyl groups.

The term "cycloalkenyl", as used herein, refers to a monovalent or divalent group of 3 to 8 carbon atoms derived from a saturated cycloalkyl having at least one double bond. Cycloalkenyl groups can be monocyclic or polycyclic. Cycloalkenyl groups can be independently substituted with one or more halogen atoms, sulfonyl groups, sulfoxide groups, nitro groups, —$OC_{1-6}$ alkyl groups, —$SC_{1-8}$ alkyl groups, —$C_{1-6}$ alkyl groups, ketone groups, alkylamino groups, amino groups, aryl groups, $C_{3-8}$ cycloalkyl groups and/or hydroxyl groups.

The term "halogen", as used herein, refers to an atom of fluorine, chlorine, bromine, iodine.

The term "heterocycle" as used herein, refers to a 3 to 10 membered ring, which can be aromatic or non-aromatic, saturated or unsaturated, containing at least one heteroatom selected form oxygen, nitrogen, sulfur, or combinations of at least two thereof, interrupting the carbocylic ring structure. The heterocylic ring can be interrupted by a C=O; the S and N heteroatoms can be oxidized. Heterocycles can be monocyclic or polycyclic. Heterocyclic ring moieties can be substituted with one or more halogen atoms, sulfonyl groups, sulfoxide groups, nitro groups, —OC$_{1-8}$ alkyl groups, —SC$_{1-8}$ alkyl groups, —C$_{1-8}$ alkyl groups, ketone groups, alkylamino groups, amino groups, aryl groups, C$_{3-8}$ cycloalkyl groups and/or hydroxyl groups.

The term "aryl" as used herein, refers to an organic moiety derived from an aromatic hydrocarbon consisting of a ring containing 6 to 10 carbon atoms, by removal of one hydrogen atom. Aryl can be substituted with one or more halogen atoms, sulfonyl C$_{1-8}$ alkyl groups, sulfoxide C$_{1-8}$ alkyl groups, sulfonamide groups, carboxylic acid groups, C$_{1-8}$ alkyl carboxylates (ester) groups, amide groups, nitro groups, —OC$_{1-6}$ alkyl groups, —SC$_{1-8}$ alkyl groups, —C$_{1-8}$ alkyl groups, ketone groups, alkylamino groups, amino groups, C$_{3-8}$ cycloalkyl groups and/or hydroxyl groups. Aryls can be monocyclic or polycyclic.

The term "hydroxyl" as used herein, represents a group of formula "—OH".

The term "carbonyl" as used herein, represents a group of formula "—C(O)—".

The term "ketone" as used herein, represents an organic compound having a carbonyl group linked to a carbon atom such as —C(O)R$^x$ wherein R$^x$ can be alkyl, aryl, cycloalkyl, cycloalkenyl or heterocycle, as defined above.

The term "ester" as used herein, represents an organic compound having a carbonyl group linked to a carbon atom such as —C(O)OR$^x$ wherein R$^x$ can be alkyl, aryl, cycloalkyl, cycloalkenyl or heterocycle, as defined above.

The term "amine" as used herein, represents a group of formula "—NR$^x$R$^y$", wherein R$^x$ and R$^y$ can be the same or independently H, alkyl, aryl, cycloalkyl, cycloalkenyl or heterocycle, as defined above.

The term "carboxyl" as used herein, represents a group of formula "—C(O)O—".

The term "sulfonyl" as used herein, represents a group of formula "—SO$_2$—".

The term "sulfate" as used herein, represents a group of formula "—OS(O)$_2$O—".

The term "sulfonate" as used herein, represents a group of the formula "—S(O)$_2$O—".

The term "carboxylic acid" as used herein, represents a group of formula "—C(O)OH".

The term "nitro" as used herein, represents a group of formula "—NO$_2$".

The term "amide" as used herein, represents a group of formula "—C(O)NR$^x$R$^y$" wherein R$^x$ and R$^y$ can be the same or independently H, alkyl, aryl, cycloalkyl, cycloalkenyl or heterocycle, as defined above.

The term "sulfonamide" as used herein, represents a group of formula "—S(O)$_2$NR$^x$R$^y$" wherein R$^x$ and R$^y$ can be the same or independently H, alkyl, aryl, cycloalkyl, cycloalkenyl or heterocycle, as defined above.

The term "sulfoxide" as used herein, represents a group of formula "—S(O)—".

The term "phosphonic acid" as used herein, represents a group of formula "—P(O)(OH)$_2$".

The term "phosphoric acid" as used herein, represents a group of formula "—OP(O)(OH)$_2$".

The term "sulphonic acid" as used herein, represents a group of formula "—S(O)$_2$OH".

The formula "H", as used herein, represents a hydrogen atom.

The formula "O", as used herein, represents an oxygen atom.

The formula "N", as used herein, represents a nitrogen atom.

The formula "S", as used herein, represents a sulfur atom.

Some compounds of the invention are:
tert-Butyl {[(2S)-2-{[(4-Bromophenyl)carbamoyl]oxy}-4-methyl pentanoyl]amino}acetate;
tert-Butyl {[(2S)-4-Methyl-2-({[4-(trifluoromethyl)phenyl] carbamoyl}oxy)pentanoyl]amino}acetate;
tert-Butyl {[(2S)-2-{[(4-Bromophenyl)carbamoyl]oxy}-4-methylpentanoyl](methyl)amino}acetate;
(2S)-1-[(2-Hydroxyethyl)(methyl)amino]-4-methyl-1-oxopentan-2-yl (4-bromophenyl)carbamate;
Diethyl ({[(2S)-4-methyl-2-({[4-(Trifluoromethyl)phenyl] carbamoyl}oxy)pentanoyl]amino}methyl)phosphonate;
(2S)-1-[(2-Hydroxyethyl)amino]-4-Methyl-1-oxopentan-2-yl [4-(trifluoromethyl)phenyl]carbamate;
(2S)-1-[(2-Hydroxyethyl)amino]-4-methyl-1-oxopentan-2-yl (4-bromophenyl)carbamate;
Diethyl ({[(2S)-2-{[(4-bromophenyl)carbamoyl]oxy}-4-methylpentanoyl]amino}methyl)phosphonate;
tert-Butyl {[(2S)-2-{[(4-Bromophenyl)carbamoyl]oxy}-4-methylpentanoyl](propyl)amino}acetate;
tert-Butyl {[(2S)-2-{[(4-Bromophenyl)carbamoyl]oxy}-4-methylpentanoyl](propan-2-yl)amino}acetate;
tert-Butyl {[(2S)-2-{[(4-Bromophenyl)carbamoyl]oxy}-4-methylpentanoyl](ethyl)amino}acetate;
tert-Butyl {Methyl[(2S)-4-methyl-2-({[4-(trifluoromethyl) phenyl]carbamoyl}oxy)pentanoyl]amino}acetate;
tert-Butyl {Ethyl[(2S)-4-methyl-2-({[4-(trifluoromethyl) phenyl]carbamoyl}oxy)pentanoyl]amino}acetate;
(2S)-4-Methyl-1-oxo-1-[(1H-tetrazol-5-ylmethyl)amino] pentan-2-yl (4-bromophenyl)carbamate;
(2S)-4-methyl-1-oxo-1-[(1H-tetrazol-5-ylmethyl)amino] pentan-2-yl [4-(trifluoromethyl)phenyl]carbamate;
(2S)-4-methyl-1-[methyl(1H-tetrazol-5-ylmethyl)amino]-1-oxopentan-2-yl (4-bromophenyl)carbamate;
(2S)-4-methyl-1-[methyl(1H-tetrazol-5-ylmethyl)amino]-1-oxopentan-2-yl [4-(trifluoromethyl)phenyl]carbamate;
2-{[(2S)-4-Methyl-2-({[4-(trifluoromethyl)phenyl] carbamoyl}oxy)pentanoyl]amino}ethyl acetate;
{[(2S)-2-{[(4-Bromophenyl)carbamoyl]oxy}-4-methylpentanoyl]amino}acetic acid;
{[(2S)-4-Methyl-2-({[4-(trifluoromethyl)phenyl] carbamoyl}oxy)pentanoyl]amino}acetic acid;
{[(2S)-2-{[(4-Bromophenyl) carbamoyl]oxy}-4-methylpentanoyl](methyl)amino}acetic acid;
{[(2S)-2-{[(4-Bromophenyl)carbamoyl]oxy}-4-methylpentanoyl](propyl)amino}acetic acid; {[(2S)-2-{[(4-Bromophenyl)carbamoyl]oxy}-4-methylpentanoyl](propan-2-yl)amino}acetic acid;
{[(2S)-2-{[(4-Bromophenyl) carbamoyl]oxy}-4-methylpentanoyl](ethyl)amino}acetic acid;
{Methyl[(2S)-4-methyl-2-({[4-(trifluoromethyl)phenyl] carbamoyl}oxy)pentanoyl]amino}acetic acid;
{Ethyl[(2S)-4-methyl-2-({[4-(trifluoromethyl)phenyl] carbamoyl}oxy)pentanoyl]amino}acetic acid;
(2S)-4-Methyl-1-{methyl[2-(sulfooxy)ethyl]amino}-1-oxopentan-2-yl (4-bromophenyl) carbamate;
({(2S)-4-methyl-2-[({[4-(trifluoromethyl)phenyl] amino}carbonyl)oxy]pentanoyl}amino)methanesulfonic acid;
tert-Butyl [{(2S)-4-methyl-2-[({[4-(trifluoromethyl)phenyl] amino}carbonyl)oxy]pentanoyl}(propyl)amino]acetate;
tert-Butyl (isopropyl{(2S)-4-methyl-2-[({[4-(trifluoromethyl)phenyl]amino}carbonyl)oxy]pentanoyl}amino)acetate;
(1S)-1-{[ethyl(1H-tetrazol-5-ylmethyl)amino]carbonyl}-3-methylbutyl (4-bromophenyl)carbamate;
(1S)-1-{[ethyl(1H-tetrazol-5-ylmethyl)amino]carbonyl}-3-methylbutyl [4-(trifluoromethyl)phenyl]carbamate;

(1S)-1-[({2-[(tert-butoxycarbonyl)amino]ethyl}amino)carbonyl]-3-methylbutyl (4-bromophenyl)carbamate;
tert-Butyl {[(2S)-2-({[(4-bromophenyl)amino]carbonyl}oxy)-3-phenylpropanoyl]amino}acetate;
(1S)-1-benzyl-2-oxo-2-[(1H-tetrazol-5-ylmethyl)amino]ethyl (4-bromophenyl)carbamate;
tert-Butyl {[(2S)-2-({[(4-bromophenyl)amino]carbonyl}oxy)-3-phenylpropanoyl](methyl)amino}acetate;
[{(2S)-4-methyl-2-[({[4-(trifluoromethyl)phenyl]amino}carbonyl)oxy]pentanoyl}(propyl)amino]acetic acid;
(Isopropyl{(2S)-4-methyl-2-[({[4-(trifluoromethyl)phenyl]amino}carbonyl) oxy]pentanoyl}amino)acetic acid;
(1S)-1-{[(2-aminoethyl)amino]carbonyl}-3-methylbutyl (4-bromophenyl) carbamate;
{[(2S)-2-({[(4-bromophenyl)amino]carbonyl}oxy)-3-phenylpropanoyl]amino}acetic acid;
{[(2S)-2-({[(4-Bromophenyl)amino]carbonyl}oxy)-3-phenylpropanoyl](methyl)amino}acetic acid; and
(1S)-1-{[(2-{[(Dimethylamino)sulfonyl]amino}ethyl)amino]carbonyl}-3-methylbutyl (4-bromophenyl)carbamate.

Additional compounds of the invention are:
(S)-tert-Butyl 2-(((4-Bromophenyl)carbamoyl)oxy)-4-methylpentanoate;
(2S)-2-{[(4-Bromophenyl)carbamoyl]oxy}-4-methylpentanoic acid;
tert-Butyl (2S)-4-Methyl-2-({[4-(trifluoromethyl)phenyl]carbamoyl}oxy)pentanoate;
(2S)-4-Methyl-2-({[4-(Trifluoromethyl)phenyl]carbamoyl}oxy)pentanoic acid; tert-Butyl (2S)-2-({[(4-bromophenyl)amino]carbonyl}oxy)-3-phenyl propanoate; and
(2S)-2-({[(4-bromophenyl)amino]carbonyl}oxy)-3-phenyl-propanoic acid.

Some compounds of Formula I and some of their intermediates have at least one asymmetric center in their structure. This asymmetric center may be present in an R or S configuration, said R and S notation is used in correspondence with the rules described in Pure Appl. Chem. (1976), 45, 11-13.

The term "pharmaceutically acceptable salts" refers to salts or complexes that retain the desired biological activity of the above identified compounds and exhibit minimal or no undesired toxicological effects. The "pharmaceutically acceptable salts" according to the invention include therapeutically active, non-toxic base or acid salt forms, which the compounds of Formula I are able to form.

The acid addition salt form of a compound of Formula I that occurs in its free form as a base can be obtained by treating the free base with an appropriate acid such as an inorganic acid, for example, hydrochloric acid, hydrobromic acid, sulfuric acid, phosphoric acid, nitric acid and the like; or an organic acid such as for example, acetic acid, hydroxyacetic acid, propanoic acid, lactic acid, pyruvic acid, malonic acid, fumaric acid, maleic acid, oxalic acid, tartaric acid, succinic acid, malic acid, ascorbic acid, benzoic acid, tannic acid, pamoic acid, citric acid, methylsulfonic acid, ethanesulfonic acid, benzenesulfonic acid, formic and the like (Handbook of Pharmaceutical Salts, P. Heinrich Stahl & Camille G. Wermuth (Eds), Verlag Helvetica Chimica Acta-Zürich, 2002, 329-345).

The base addition salt form of a compound of Formula I that occurs in its acid form can be obtained by treating the acid with an appropriate base such as an inorganic base, for example, sodium hydroxide, magnesium hydroxide, potassium hydroxide, calcium hydroxide, ammonia and the like; or an organic base such as for example, L-Arginine, ethanolamine, betaine, benzathine, morpholine and the like. (Handbook of Pharmaceutical Salts, P. Heinrich Stahl & Camille G. Wermuth (Eds), Verlag Helvetica Chimica Acta-Zürich, 2002, 329-345).

The compounds of the invention are indicated for use in treating or preventing conditions in which there is likely to be a component involving the N-formyl peptide receptor 2.

In another embodiment, there are provided pharmaceutical compositions including at least one compound of the invention in a pharmaceutically acceptable carrier.

In a further embodiment of the invention, there are provided methods for treating disorders associated with modulation of the N-formyl peptide 2 receptor.

Such methods can be performed, for example, by administering to a subject in need thereof a pharmaceutical composition containing a therapeutically effective amount of at least one compound of the invention.

Therapeutic utilities of the N-formyl peptide 2 receptor modulators are ocular inflammatory diseases and conditions including, but not limited to, wet and dry age-related macular degeneration (ARMD), uveitis, dry eye, keratitis, allergic eye disease and conditions affecting the posterior part of the eye, such as maculopathies and retinal degeneration including non-exudative age related macular degeneration, exudative age related macular degeneration, choroidal neovascularization, diabetic retinopathy (proliferative), retinopathy of prematurity (ROP), acute macular neuroretinopathy, central serous chorioretinopathy, cystoid macular edema, and diabetic macular edema; infectious keratitis, herpetic keratitis, corneal angiogenesis, lymphangiogenesis, retinitis, choroiditis such as acute multifocal placoid pigment epitheliopathy, Behcet's disease, birdshot retinochoroidopathy, infectious (syphilis, lyme, tuberculosis, toxoplasmosis), intermediate uveitis (pars planitis), multifocal choroiditis, multiple evanescent white dot syndrome (mewds), ocular sarcoidosis, posterior scleritis, serpiginous choroiditis, subretinal fibrosis and uveitis syndrome, Vogt-Koyanagi- and Harada syndrome; vascular diseases/exudative diseases such as retinal arterial occlusive disease, central retinal vein occlusion, cystoids macular edema, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, and Eales disease; traumatic/surgical conditions such as sympathetic ophthalmia, uveitic retinal disease, retinal detachment, trauma, post surgical corneal wound healing, post-cataract surgical inflammation, conditions caused by laser, conditions caused by photodynamic therapy, photocoagulation, hypoperfusion during surgery, radiation retinopathy, and bone marrow transplant retinopathy; proliferative disorders such as proliferative vitreal retinopathy and epiretinal membranes, and proliferative diabetic retinopathy; infectious disorders such as ocular histoplasmosis, ocular toxocariasis, presumed ocular histoplasmosis syndrome (POHS), endophthalmitis, toxoplasmosis, retinal diseases associated with HIV infection, choroidal disease associate with HIV infection, uveitic disease associate with HIV infection, viral retinitis, acute retinal necrosis, progressive outer retinal necrosis, fungal retinal diseases, ocular syphilis, ocular tuberculosis, diffuse unilateral subacute neuroretinitis, and myiasis; genetic disorders such as retinitis pigmentosa, systemic disorders with associated retinal dystrophies, congenital stationary night blindness, cone dystrophies, Stargardt's disease and fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, and pseudoxanthoma elasticum; retinal tears/holes such as retinal detachment, macular hole, and giant retinal tear; tumors such as retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors; and miscellaneous other diseases affecting the posterior part of the eye such as punctate inner choroidopathy, acute posterior multifocal placoid pigment epitheliopathy, myopic retinal degeneration, and acute retinal pigment epitheliitis, systemic inflammatory diseases such as stroke, coronary artery disease, obstructive airway diseases, HIV-mediated retroviral infections, cardiovascular disorders including coronary artery disease, neuroinflammation, neurological disorders, pain and immunological disorders, asthma, allergic disorders, inflammation, systemic lupus erythematosus, psoriasis, CNS disorders such as Alzheimer's disease, arthritis, sepsis, inflammatory bowel disease, cachexia, angina pectoris, post-surgical corneal inflammation, blepharitis, meibomian gland dysfunction; dermal inflammation and dermal diseases including but not limited to dermal wound healing, hypertrophic scars, keloids, burns, rosacea, atopic dermatitis, acne, psoriasis, seborrheic dermatitis, actinic keratoses, basal cell carcinoma, squamous cell carcinoma, melanoma, viral warts, photoaging, photodamage, melasma, post-inflammatory hyperpigmentation, disorders of pigmentation, alopecia, scarring and non-scarring forms; viral warts, photoaging rheumatoid arthritis and related inflammatory disorders, alopecia, glaucoma, branch vein occlusion, Best's vitelliform macular degeneration, retinitis pigmentosa, proliferative vitreoretinopathy (PVR), and any other degenerative disease of either the photoreceptors or the RPE (Perretti, Mauro et al. Pharmacology & Therapeutics 127 (2010) 175-188).

The compounds of the invention are useful for the treatment of mammals, including humans, with a range of conditions and diseases that are alleviated by the N-formyl peptide 2 receptor modulation, including, but not limited to the treatment of wet and dry age-related macular degeneration (ARMD), dry eye, keratitis, allergic eye disease, infectious keratitis, herpetic keratitis, corneal angiogenesis, lymphangiogenesis, retinitis, choroiditis, acute multifocal placoid pigment epitheliopathy, Behcet's disease, post-surgical corneal wound healing, post-cataract surgical inflammation, uveitis, diabetic retinopathy (proliferative), retinopathy of prematurity (ROP), diabetic macular edema, retinal vein occlusion, cystoids macular edema, glaucoma, branch vein occlusion, Best's vitelliform macular degeneration, retinitis pigmentosa, proliferative vitreoretinopathy (PVR), and any other degenerative disease of either the photoreceptors or the RPE; also dermal inflammation and dermal diseases including but not limited to dermal wound healing, hypertrophic scars, keloids, burns, rosacea, atopic dermatitis, acne, psoriasis, seborrheic dermatitis, actinic keratoses, basal cell carcinoma, squamous cell carcinoma, melanoma, viral warts, photodamage, melasma, post-inflammatory hyperpigmentation, disorders of pigmentation, alopecia, scarring and non-scarring forms.

In still another embodiment of the invention, there are provided methods for treating disorders associated with modulation of the FPR2 receptor. Such methods can be performed, for example, by administering to a subject in need thereof a therapeutically effective amount of at least one compound of the invention, or any combination thereof, or pharmaceutically acceptable salts, individual enantiomers, and/or diastereomers thereof.

The present invention concerns the use of a compound of Formula I or a pharmaceutically acceptable salt thereof, for the manufacture of a medicament for the treatment of ocular inflammatory diseases including, but not limited to, wet and dry age-related macular degeneration (ARMD), uveitis, dry eye, keratitis, allergic eye disease and conditions affecting the posterior part of the eye, such as maculopathies and retinal degeneration including non-exudative age related macular degeneration, exudative age related macular degeneration, choroidal neovascularization, diabetic retinopathy (proliferative), retinopathy of prematurity (ROP), acute macular neuroretinopathy, central serous chorioretinopathy, cystoid macular edema, and diabetic macular edema; infectious keratitis, herpetic keratitis, corneal angiogenesis, lymphangiogenesis, uveitis, retinitis, and choroiditis such as acute multifocal placoid pigment epitheliopathy, Behcet's disease, birdshot retinochoroidopathy, infectious (syphilis, lyme, tuberculosis, toxoplasmosis) intermediate uveitis (pars planitis), multifocal choroiditis, multiple evanescent white dot syndrome (mewds), ocular sarcoidosis, posterior scleritis, serpiginous choroiditis, subretinal fibrosis and uveitis syndrome, Vogt-Koyanagi- and Harada syndrome; vasuclar diseases/exudative diseases such as retinal arterial occlusive disease, central retinal vein occlusion, cystoids macular edema, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, and Eales disease; traumatic/surgical conditions such as sympathetic ophthalmia, uveitic retinal disease, retinal detachment, trauma, post surgical corneal wound healing, post-cataract surgical inflammation, wet and dry age-related macular degeneration (ARMD), conditions caused by laser, conditions caused by photodynamic therapy, photocoagulation, hypoperfusion during surgery, radiation retinopathy, and bone marrow transplant retinopathy; proliferative disorders such as proliferative vitreal retinopathy and epiretinal membranes, and proliferative diabetic retinopathy; infectious disorders such as ocular histoplasmosis, ocular toxocariasis, presumed ocular histoplasmosis syndrome (POHS), endophthalmitis, toxoplasmosis, retinal diseases associated with HIV infection, choroidal disease associate with HIV infection, uveitic disease associate with HIV infection, viral retinitis, acute retinal necrosis, progressive outer retinal necrosis, fungal retinal diseases, ocular syphilis, ocular tuberculosis, diffuse unilateral subacute neuroretinitis, and myiasis; genetic disorders such as retinitis pigmentosa, systemic disorders with associated retinal dystrophies, congenital stationary night blindness, cone dystrophies, Stargardt's disease and fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, and pseudoxanthoma elasticum; retinal tears/holes such as retinal detachment, macular hole, and giant retinal tear; tumors such as retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors; and miscellaneous other diseases affecting the posterior part of the eye such as punctate inner choroidopathy, acute posterior multifocal placoid pigment epitheliopathy, myopic retinal degeneration, and acute retinal pigment epitheliitis, systemic inflammatory diseases such as stroke, coronary artery disease, obstructive airway diseases, HIV-mediated retroviral infections, cardiovascular disorders including coronary artery disease, neuroinflammation, neurological disorders, pain and immunological disorders, asthma, allergic disorders, inflammation, systemic lupus erythematosus, CNS disorders such as Alzheimer's disease, arthritis, sepsis, inflammatory bowel disease, cachexia, angina pectoris, post-surgical corneal inflammation, blepharitis, meibomian gland dysfunction, viral warts, photoaging rheumatoid arthritis and related inflammatory disorders, alopecia, glaucoma, branch vein occlusion, Best's vitelliform macular degeneration, retinitis pigmentosa, proliferative vitreoretinopathy (PVR), and any other degenerative disease of either the photoreceptors or the RPE; dermal inflammation and dermal diseases including but not limited to dermal wound healing, hypertrophic scars, keloids, burns, rosacea, atopic dermatitis, acne, psoriasis, seborrheic dermatitis, actinic keratoses, basal cell carcinoma, squamous cell carcinoma, melanoma, viral warts, photoaging, photodamage, melasma, post-inflammatory hyperpigmentation, disorders of pigmentation, alopecia, scarring and non-scarring forms.

The actual amount of the compound to be administered in any given case will be determined by a physician taking into account the relevant circumstances, such as the severity of the condition, the age and weight of the patient, the patient's general physical condition, the cause of the condition, and the route of administration.

The patient will be administered the compound orally in any acceptable form, such as a tablet, liquid, capsule, powder and the like, or other routes may be desirable or necessary, particularly if the patient suffers from nausea. Such other routes may include, without exception, transdermal, parenteral, subcutaneous, intranasal, via an implant stent, intrathecal, intravitreal, topical to the eye, back to the eye, intramuscular, intravenous, and intrarectal modes of delivery. Additionally, the formulations may be designed to delay release of the active compound over a given period of time, or to carefully control the amount of drug released at a given time during the course of therapy.

In another embodiment of the invention, there are provided pharmaceutical compositions including at least one compound of the invention in a pharmaceutically acceptable carrier thereof. The phrase "pharmaceutically acceptable" means the carrier, diluent or excipient must be compatible with the other ingredients of the formulation and not deleterious to the recipient thereof.

Pharmaceutical compositions of the present invention can be used in the form of a solid, a solution, an emulsion, a dispersion, a patch, a micelle, a liposome, and the like, wherein the resulting composition contains one or more compounds of the present invention, as an active ingredient, in admixture with an organic or inorganic carrier or excipient suitable for enteral or parenteral applications. Invention compounds may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition, auxiliary, stabilizing, thickening and coloring agents and perfumes may be used. Invention compounds are included in the pharmaceutical composition in an amount sufficient to produce the desired effect upon the process or disease condition.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin or olive oil.

Pharmaceutical compositions containing invention compounds may be in a form suitable for topical use, for example, as oily suspensions, as solutions or suspensions in aqueous liquids or nonaqueous liquids, or as oil-in-water or water-in-oil liquid emulsions. Pharmaceutical compositions may be prepared by combining a therapeutically effective amount of at least one compound according to the present invention, or a pharmaceutically acceptable salt thereof, as an active ingredient with conventional ophthalmically acceptable pharmaceutical excipients and by preparation of unit dosage suitable for topical ocular use. The therapeutically efficient amount typically is between about 0.0001 and about 5% (w/v), preferably about 0.001 to about 2.0% (w/v) in liquid formulations.

For ophthalmic application, preferably solutions are prepared using a physiological saline solution as a major vehicle. The pH of such ophthalmic solutions should preferably be maintained between 4.5 and 8.0 with an appropriate buffer system, a neutral pH being preferred but not essential. The formulations may also contain conventional pharmaceutically acceptable preservatives, stabilizers and surfactants. Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose cyclodextrin and purified water.

Tonicity adjustors may be added as needed or convenient They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar manner an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edetate disodium, although other chelating agents may also be used in place of or in conjunction with it.

The ingredients are usually used in the following amounts:

| Ingredient | Amount (% w/v) |
|---|---|
| active ingredient | about 0.001-5 |
| preservative | 0-0.10 |
| vehicle | 0-40 |
| tonicity adjustor | 0-10 |
| buffer | 0.01-10 |
| pH adjustor | q.s. pH 4.5-7.8 |
| antioxidant | as needed |
| surfactant | as needed |
| purified water | to make 100%. |

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate application to the eye. Containers suitable for dropwise application are usually made of suitable inert, non-toxic plastic material, and generally contain between about 0.5 and about 15 ml solution. One package may contain one or more unit doses. Especially preservative-free solutions are often formulated in non-resealable containers containing up to about ten, preferably up to about five unit doses, where a typical unit dose is from one to about 8 drops, preferably one to about 3 drops. The volume of one drop usually is about 20-35 microliters.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

The compounds of the invention may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquefy and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner.

The compounds and pharmaceutical compositions described herein are useful as medicaments in mammals, including humans, for treatment of diseases and/or alleviations of conditions which are responsive to treatment by agonists or functional antagonists of the N-formyl peptide 2 receptor. Thus, in further embodiments of the invention, there are provided methods for treating a disorder associated with modulation of the N-formyl peptide 2 receptor. Such methods can be performed, for example, by administering to a subject in need thereof a pharmaceutical composition containing a therapeutically effective amount of at least one invention compound. As used herein, the term "therapeutically effective amount" means the amount of the pharmaceutical composition that will elicit the biological or medical response of a subject in need thereof that is being sought by the researcher, veterinarian, medical doctor or other clinician. In some embodiments, the subject in need thereof is a mammal. In some embodiments, the mammal is human.

The present invention concerns also processes for preparing the compounds of Formula I. The compounds of formula I according to the invention can be prepared analogously to conventional methods as understood by the person skilled in the art of synthetic organic chemistry.

Synthetic Scheme 1 set forth below illustrates how the compounds according to the invention can be made. Those skilled in the art will be able to routinely modify and/or adapt the following scheme to synthesize any compounds of the invention covered by Formula I or their synthetic precursors.

Scheme 1

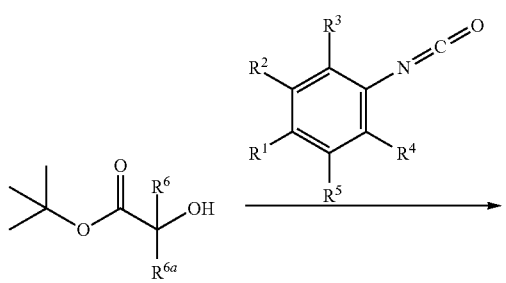

-continued

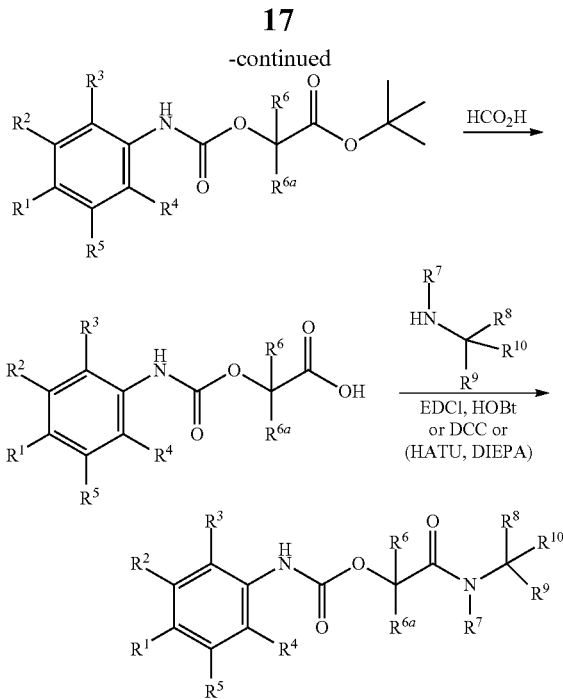

Compounds of Formula I were prepared as depicted in Scheme 1. In general, a t-butyl ester derivative of an alpha-hydroxy carboxylic acid is reacted with a substituted phenylisocyanate to produce a phenylcarbamate derivative. The t-butyl ester protecting group is then removed under acidic conditions to give a phenylcarbamate acetic acid derivative. The carboxylic acid group is then converted to an amide by treating the compound with activating reagents, such as 1-ethyl-3-(3-dimethylaminopropyl) carbodiimide (EDC) and hydroxybenzotriazole (HOBt) in the presence of an amine, or by other methods known to those skilled in the art.

The following abbreviations are used in the general scheme and in the examples:

Et$_3$N triethylamine
CD$_3$OD deuterated methanol
Na$_2$SO$_4$ sodium sulfate
DMF N,N dimethylformamide
EDCI/EDC 1-ethyl-3-(3-dimethylaminopropyl) carbodiimide
HOBt hydroxybenzotriazole
THF tetrahydrofuran
TMS tetramethylsilane
EtOAc ethylacetate
HCO$_2$H formic acid
DMAP 4-dimethylaminopyridine
DCC N,N'-Dicyclohexylcarbodiimide
HATU 1-[Bis(dimethylamino)methylene]-1H-1,2,3-triazolo[4,5-b]pyridinium 3-oxid hexafluorophosphate
DIEPA N,N-Diisopropylethylamine
HCl hydrochloric acid At this stage, those skilled in the art will appreciate that many additional compounds that fall under the scope of the invention may be prepared by performing various common chemical reactions. Details of certain specific chemical transformations are provided in the examples.

DRAWINGS

FIG. 1 shows the structure of Formula I.

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise.

It will be readily apparent to those skilled in the art that some of the compounds of the invention may contain one or more asymmetric centers, such that the compounds may exist in enantiomeric as well as in diastereomeric forms. Unless it is specifically noted otherwise, the scope of the present invention includes all enantiomers, diastereomers and racemic mixtures. Some of the compounds of the invention may form salts with pharmaceutically acceptable acids or bases, and such pharmaceutically acceptable salts of the compounds described herein are also within the scope of the invention.

The present invention includes all pharmaceutically acceptable isotopically enriched compounds. Any compound of the invention may contain one or more isotopic atoms enriched or different than the natural ratio such as deuterium $^2$H (or D) in place of hydrogen $^1$H (or H) or use of $^{13}$C enriched material in place of $^{12}$C and the like. Similar substitutions can be employed for N, O and S. The use of isotopes may assist in analytical as well as therapeutic aspects of the invention. For example, use of deuterium may increase the in vivo half-life by altering the metabolism (rate) of the compounds of the invention. These compounds can be prepared in accord with the preparations described by use of isotopically enriched reagents.

The following examples are for illustrative purposes only and are not intended, nor should they be construed, as limiting the invention in any manner. Those skilled in the art will appreciate that variations and modifications of the following examples can be made without exceeding the spirit or scope of the invention.

In embodiment (1), there is provided a compound represented by Formula I:

Formula I

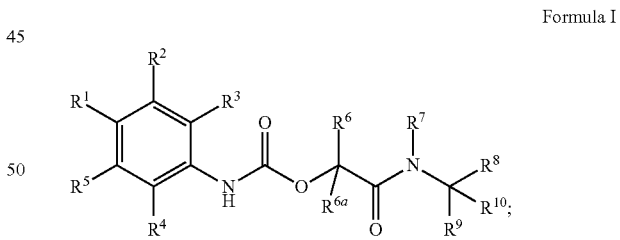

wherein:

R$^1$ is optionally substituted C$_{1-8}$ alkyl, optionally substituted C$_{3-8}$ cycloalkyl, optionally substituted heterocycle, optionally substituted C$_{6-10}$ aryl, optionally substituted C$_{3-8}$ cycloalkenyl, halogen, NR$^{11}$R$^{12}$, fluorinated C$_{1-8}$ alkyl, perfluorinated C$_{1-8}$ alkyl, —S(O)$_m$R$^{13}$, —C(O)R$^{14}$ or —OR$^{15}$;

R$^2$ is H, optionally substituted C$_{1-8}$ alkyl, optionally substituted C$_{3-8}$ cycloalkyl, optionally substituted heterocycle, optionally substituted C$_{6-10}$ aryl, optionally substituted C$_{3-8}$ cycloalkenyl, halogen, NR$^{11}$R$^{12}$, fluorinated C$_{1-8}$ alkyl, perfluorinated C$_{1-8}$ alkyl, —S(O)$_m$R$^{13}$—C(O)R$^{14}$ or —OR$^{15}$;

R$^3$ is H, optionally substituted C$_{1-8}$ alkyl, optionally substituted C$_{3-8}$ cycloalkyl, optionally substituted heterocycle, optionally substituted $C_{6-10}$ aryl, optionally substituted $C_{3-8}$ cycloalkenyl, halogen, $NR^{11}R^{12}$, fluorinated $C_{1-8}$ alkyl, perfluorinated $C_{1-8}$ alkyl, —S(O)$_m$R$^{13}$—C(O)R$^{14}$ or —OR$^{15}$;

$R^4$ is H, optionally substituted $C_{1-8}$ alkyl, optionally substituted $C_{3-8}$ cycloalkyl, optionally substituted heterocycle, optionally substituted $C_{6-10}$ aryl, optionally substituted $C_{3-8}$ cycloalkenyl, halogen, $NR^{11}R^{12}$, fluorinated $C_{1-8}$ alkyl, perfluorinated $C_{1-8}$ alkyl, —S(O)$_m$R$^{13}$—C(O)R$^{14}$ or —OR$^{15}$;

$R^5$ is H, optionally substituted $C_{1-8}$ alkyl, optionally substituted $C_{3-8}$ cycloalkyl, optionally substituted heterocycle, optionally substituted $C_{6-10}$ aryl, optionally substituted $C_{3-8}$ cycloalkenyl, halogen, $NR^{11}R^{12}$, fluorinated $C_{1-8}$ alkyl, perfluorinated $C_{1-8}$ alkyl, —S(O)$_m$R$^{13}$—C(O)R$^{14}$ or —OR$^{15}$;

$R^6$ is H, optionally substituted $C_{1-8}$ alkyl, optionally substituted heterocycle, —(CH$_2$)$_p$COOH, —(CH$_2$)$_p$—NH$_2$, —(CH$_2$)$_p$—OH, —(CH$_2$)$_p$—SH, —(CH$_2$)$_p$—CONH$_2$, —(CH$_2$)$_p$—CONH$_2$, —CH(OH)CH$_3$, —(CH$_2$)$_p$SCH$_3$, —(CH$_2$)$_p$NH—C(=NH)(NH$_2$) or —CH$_2$C$_{6-10}$ aryl, wherein said —C$_{6-10}$ aryl is optionally substituted;

$R^{6a}$ is H or optionally substituted $C_{1-8}$ alkyl;

$R^7$ is H or optionally substituted $C_{1-8}$ alkyl;

$R^8$ is H;

$R^9$ is H, optionally substituted $C_{1-8}$ alkyl, optionally substituted $C_{3-8}$ cycloalkyl, optionally substituted heterocycle, optionally substituted $C_{6-10}$ aryl or optionally substituted $C_{3-8}$ cycloalkenyl;

$R^{10}$ is —(CH$_2$)$_n$OR$^{16}$, —(CH$_2$)$_n$S(O)$_2$OH, —(CH$_2$)$_n$C(O)R$^{17}$, —(CH$_2$)$_n$OS(O)$_2$OH, —(CH$_2$)$_n$NR$^{18}$R$^{19}$, —(CH$_2$)$_n$P(O)(OC$_{1-6}$ alkyl)$_2$, —(CH$_2$)$_n$P(O)(OC$_{1-6}$ alkyl)OH, —(CH$_2$)$_n$—P(O)(OH)$_2$ or optionally substituted heterocycle;

$R^{11}$ is H, optionally substituted $C_{1-8}$ alkyl, optionally substituted $C_{3-8}$ cycloalkyl, optionally substituted heterocycle, optionally substituted $C_{6-10}$ aryl or optionally substituted $C_{3-8}$ cycloalkenyl;

$R^{12}$ is H, optionally substituted $C_{1-8}$ alkyl, optionally substituted $C_{3-8}$ cycloalkyl, optionally substituted heterocycle, optionally substituted $C_{6-10}$ aryl or optionally substituted $C_{3-8}$ cycloalkenyl;

$R^{13}$ is H, optionally substituted $C_{1-8}$ alkyl, optionally substituted $C_{3-8}$ cycloalkyl, optionally substituted heterocycle, optionally substituted $C_{6-10}$ aryl, OH or optionally substituted $C_{3-8}$ cycloalkenyl;

$R^{14}$ is optionally substituted $C_{1-8}$ alkyl, optionally substituted $C_{3-8}$ cycloalkyl, optionally substituted heterocycle, optionally substituted $C_{6-10}$ aryl, optionally substituted $C_{3-8}$ cycloalkenyl or —OR$^{15}$;

$R^{15}$ is H or optionally substituted $C_{1-8}$ alkyl;

$R^{16}$ is H, —C(O)(C$_{1-8}$ alkyl) or optionally substituted $C_{1-8}$ alkyl;

$R^{17}$ is OH, —OC$_{1-8}$ alkyl or $C_{1-8}$ alkyl;

$R^{18}$ is selected from the group consisting of H, optionally substituted $C_{1-8}$ alkyl, optionally substituted $C_{3-8}$ cycloalkyl, optionally substituted heterocycle, optionally substituted $C_{6-10}$ aryl, optionally substituted $C_{3-8}$ cycloalkenyl, —C(O)R$^{17}$ and —S(O)$_2$N(C$_{1-8}$ alkyl)$_2$;

$R^{19}$ is selected from the group consisting of H, optionally substituted $C_{1-8}$ alkyl, optionally substituted $C_{3-8}$ cycloalkyl, optionally substituted heterocycle, optionally substituted $C_{6-10}$ aryl, or optionally substituted $C_{3-8}$ cycloalkenyl, —C(O)R$^{17}$ and —S(O)$_2$N(C$_{1-8}$ alkyl)$_2$;

p is 1, 2 or 3;

n is 0, 1, 2, 3, 4, 5, 6, 7 or 8; and m is 0, 1 or 2;

wherein each $C_{1-8}$ alkyl substituent is independently selected from the group consisting of halogen, hydroxyl, —OC$_{1-8}$alkyl, $C_{3-8}$cycloalkyl, amino, heterocycle, $C_{6-10}$aryl, carboxylic acid, phosphonic acid, sulphonic acid, phosphoric acid, nitro, amide, sulfonamide, carboxylate ester and ketone;

each $C_{3-8}$ cycloalkyl substituent is independently selected from the group consisting of halogen, hydroxyl, sulfonyl $C_{1-8}$ alkyl, sulfoxide $C_{1-8}$ alkyl, sulfonamide, nitro, —OC$_{1-8}$ alkyl, —SC$_{1-8}$ alkyl groups, —C$_{1-8}$ alkyl, ketone, alkylamino, amino, $C_{6-10}$ aryl and $C_{3-8}$ cycloalkyl;

each heterocycle substituent is independently selected from the group consisting of halogen, hydroxyl, —OC$_{1-8}$ alkyl, sulfonyl $C_{1-8}$ alkyl, sulfoxide $C_{1-8}$ alkyl, nitro, —SC$_{1-8}$ alkyl, —C$_{1-8}$ alkyl, ketone, alkylamino, amino, $C_{6-10}$ aryl and $C_{3-8}$ cycloalkyl;

each $C_{6-10}$ aryl substituent is independently selected from the group consisting of halogen, hydroxyl, sulfonyl $C_{1-8}$ alkyl, sulfoxide $C_{1-8}$ alkyl, sulfonamide, carboxylic acid, $C_{1-8}$ alkyl carboxylate (ester), amide, nitro, —OC$_{1-8}$ alkyl, —SC$_{1-8}$ alkyl, —C$_{1-8}$ alkyl, ketone, alkylamino, amino and $C_{3-8}$ cycloalkyl; and each $C_{3-8}$ cycloalkenyl substituent is independently selected from the group consisting of halogen, hydroxyl, sulfonyl $C_{1-8}$ alkyl, sulfoxide $C_{1-8}$ alkyl, nitro, —OC$_{1-6}$ alkyl, —SC$_{1-6}$ alkyl, —C$_{1-6}$ alkyl, ketone, alkylamino, amino, $C_{6-10}$ aryl and $C_{3-8}$ cycloalkyl;

or an enantiomer, diastereomer or tautomer thereof;

or a pharmaceutically acceptable salt of any of the foregoing.

In embodiment (2), there is provided a compound according to embodiment (1), wherein:

n is 0 or 1;

$R^{10}$ is —(CH$_2$)$_n$OR$^{16}$, —(CH$_2$)$_n$C(O)R$^{17}$, —(CH$_2$)$_n$S(O)$_2$OH, —(CH$_2$)$_n$NR$^{18}$R$^{19}$, —(CH$_2$)$_n$—P(O)(OC$_{1-6}$ alkyl)$_2$, —(CH$_2$)$_n$—P(O)(OC$_{1-6}$alkyl)OH, —(CH$_2$)$_n$—P(O)(OH)$_2$ or optionally substituted heterocycle;

$R^{16}$ is H or —C(O)(C$_{1-8}$ alkyl);

$R^{17}$ is OH or —OC$_{1-8}$ alkyl;

$R^{18}$ H; and $R^{19}$ is selected from the group consisting of H, —C(O)R$^{17}$ and —S(O)$_2$N(C$_{1-8}$ alkyl)$_2$;

or an enantiomer, diastereomer or tautomer thereof;

or a pharmaceutically acceptable salt of any of the foregoing.

In embodiment (3), there is provided a compound according to any one of embodiments (1) or (2), wherein $R^9$ is H.

In embodiment (4), there is provided a compound according to any one of embodiments (1) through (3), wherein:

$R^6$ is H, optionally substituted $C_{1-8}$ alkyl or —CH$_2$—C$_{6-10}$aryl, wherein said $C_{1-6}$ aryl is optionally substituted; and $R^{6a}$ is H;

or an enantiomer, diastereomer or tautomer thereof;

or a pharmaceutically acceptable salt of any of the foregoing.

In embodiment (5), there is provided a compound according to any one of embodiments (1) through (4), wherein $R^7$ is H, methyl, ethyl, n-propyl, isopropyl, n-butyl, sec-butyl, isobutyl or t-butyl;

or an enantiomer, diastereomer or tautomer thereof;

or a pharmaceutically acceptable salt of any of the foregoing.

In embodiment (6), there is provided a compound according to any one of embodiments (1) through (5), wherein $R^1$ is selected from halogen, fluorinated $C_{1-8}$ alkyl and perfluorinated $C_{1-8}$ alkyl;

or an enantiomer, diastereomer or tautomer thereof;
or a pharmaceutically acceptable salt of any of the foregoing.

In embodiment (7), there is provided a compound according to any one of embodiments (1) through (6), wherein each of $R^2$, $R^3$, $R^4$ and $R^5$ is H;
or an enantiomer, diastereomer or tautomer thereof;
or a pharmaceutically acceptable salt of any of the foregoing.

In embodiment (8), there is provided a compound according to any one of embodiments (1) through (7), wherein $R^{10}$ is an optionally substituted heterocycle, wherein the heterocycle is selected from imidazole, triazole, tetrazole, oxazole and thiazole;
or an enantiomer, diastereomer or tautomer thereof;
or a pharmaceutically acceptable salt of any of the foregoing.

In embodiment (9), there is provided a compound according to any one of embodiments (1) through (8), wherein:
n is 0 or 1;
$R^1$ is selected from halogen, fluorinated $C_{1-8}$ alkyl and perfluorinated $C_{1-8}$ alkyl; each of $R^2$, $R^3$, $R^4$ and $R^5$ is H;
$R^6$ is H, optionally substituted $C_{1-8}$ alkyl or —$CH_2C_{6-10}$aryl, wherein said $C_{6-10}$aryl is optionally substituted;
$R^{6a}$ is H;
$R^9$ is H;
$R^{10}$ is —$(CH_2)_nOR^{16}$, —$(CH_2)_nC(O)R^{17}$, —$(CH_2)_n$—$S(O)_2OH$, —$(CH_2)_nNR^{18}R^{19}$, —$(CH_2)_n$—$P(O)(OC_{1-6}$ alkyl$)_2$, —$(CH_2)_n$—$P(O)(OC_{1-6}$alkyl$)OH$, —$(CH_2)_n$—$P(O)(OH)_2$ or optionally substituted heterocycle;
$R^{16}$ is H or —$C(O)(C_{1-8}$ alkyl);
$R^{17}$ is OH or —$OC_{1-8}$ alkyl;
$R^{18}$ H; and
$R^{19}$ is selected from the group consisting of H, —$C(O)R^{17}$ and —$S(O)_2N(C_{1-8}$ alkyl$)_2$;
or an enantiomer, diastereomer or tautomer thereof;
or a pharmaceutically acceptable salt of any of the foregoing.

In embodiment (10), there is provided a compound according to any one of embodiments (1) through (9) wherein —$CH_2$—$C_{6-10}$ aryl is optionally substituted benzyl.

In embodiment (11), there is provided a compound according to any one of embodiments (1) through (10), wherein:
each $C_{1-8}$ alkyl is independently selected from methyl, ethyl, n-propyl, isopropyl, n-butyl, sec-butyl, isobutyl and t-butyl; and
$R^7$ is H, methyl, ethyl, n-propyl, isopropyl, n-butyl, sec-butyl, isobutyl or t-butyl;
or an enantiomer, diastereomer or tautomer thereof;
or a pharmaceutically acceptable salt of any of the foregoing.

In embodiment (12), there is provided a compound selected from the group consisting of:
tert-Butyl {[(2S)-2-{[(4-Bromophenyl)carbamoyl]oxy}-4-methyl pentanoyl]amino}acetate;
tert-Butyl {[(2S)-4-Methyl-2-({[4-(trifluoromethyl)phenyl]carbamoyl}oxy)pentanoyl]amino}acetate;
tert-Butyl {[(2S)-2-{[(4-Bromophenyl)carbamoyl]oxy}-4-methylpentanoyl](methyl)amino}acetate;
(2S)-1-[(2-Hydroxyethyl)(methyl)amino]-4-methyl-1-oxopentan-2-yl (4-bromophenyl)carbamate;
Diethyl ({[(2S)-4-methyl-2-({[4-(Trifluoromethyl)phenyl]carbamoyl}oxy)pentanoyl]amino}methyl)phosphonate;
(2S)-1-[(2-Hydroxyethyl)amino]-4-Methyl-1-oxopentan-2-yl [4-(trifluoromethyl)phenyl]carbamate;
(2S)-1-[(2-Hydroxyethyl)amino]-4-methyl-1-oxopentan-2-yl (4-bromophenyl)carbamate;
Diethyl ({[(2S)-2-{[(4-bromophenyl)carbamoyl]oxy}-4-methylpentanoyl]amino}methyl)phosphonate;
tert-Butyl {[(2S)-2-{[(4-Bromophenyl)carbamoyl]oxy}-4-methylpentanoyl](propyl)amino}acetate;
tert-Butyl {[(2S)-2-{[(4-Bromophenyl)carbamoyl]oxy}-4-methylpentanoyl](propan-2-yl)amino}acetate;
tert-Butyl {[(2S)-2-{[(4-Bromophenyl)carbamoyl]oxy}-4-methylpentanoyl](ethyl)amino}acetate;
tert-Butyl {Methyl[(2S)-4-methyl-2-({[4-(trifluoromethyl)phenyl]carbamoyl}oxy)pentanoyl]amino}acetate;
tert-Butyl {Ethyl[(2S)-4-methyl-2-({[4-(trifluoromethyl)phenyl]carbamoyl}oxy)pentanoyl]amino}acetate;
(2S)-4-Methyl-1-oxo-1-[(1H-tetrazol-5-ylmethyl)amino]pentan-2-yl (4-bromophenyl)carbamate;
(2S)-4-methyl-1-oxo-1-[(1H-tetrazol-5-ylmethyl)amino]pentan-2-yl [4-(trifluoromethyl)phenyl]carbamate;
(2S)-4-methyl-1-[methyl(1H-tetrazol-5-ylmethyl)amino]-1-oxopentan-2-yl (4-bromophenyl)carbamate;
(2S)-4-methyl-1-[methyl(1H-tetrazol-5-ylmethyl)amino]-1-oxopentan-2-yl [4-(trifluoromethyl)phenyl]carbamate;
2-{[(2S)-4-Methyl-2-({[4-(trifluoromethyl)phenyl]carbamoyl}oxy)pentanoyl]amino}ethyl acetate;
{[(2S)-2-{[(4-Bromophenyl)carbamoyl]oxy}-4-methylpentanoyl]amino}acetic acid;
{[(2S)-4-Methyl-2-({[4-(trifluoromethyl)phenyl]carbamoyl}oxy)pentanoyl]amino}acetic acid;
{[(2S)-2-{[(4-Bromophenyl) carbamoyl]oxy}-4-methylpentanoyl](methyl)amino}acetic acid;
{[(2S)-2-{[(4-Bromophenyl)carbamoyl]oxy}-4-methylpentanoyl](propyl)amino}acetic acid;
{[(2S)-2-{[(4-Bromophenyl)carbamoyl]oxy}-4-methylpentanoyl](propan-2-yl)amino}acetic acid;
{[(2S)-2-{[(4-Bromophenyl) carbamoyl]oxy}-4-methylpentanoyl](ethyl)amino}acetic acid;
{Methyl[(2S)-4-methyl-2-({[4-(trifluoromethyl)phenyl]carbamoyl}oxy)pentanoyl]amino}acetic acid;
{Ethyl[(2S)-4-methyl-2-({[4-(trifluoromethyl)phenyl]carbamoyl}oxy)pentanoyl]amino}acetic acid;
(2S)-4-Methyl-1-{methyl[2-(sulfooxy)ethyl]amino}-1-oxopentan-2-yl (4-bromophenyl) carbamate;
({(2S)-4-methyl-2-[({[4-(trifluoromethyl)phenyl]amino}carbonyl)oxy]pentanoyl}amino)methanesulfonic acid;
tert-Butyl [{(2S)-4-methyl-2-[({[4-(trifluoromethyl)phenyl]amino}carbonyl) oxy]pentanoyl}(propyl)amino]acetate;
tert-Butyl (isopropyl{(2S)-4-methyl-2-[({[4-(trifluoromethyl)phenyl]amino}carbonyl)oxy]pentanoyl}amino)acetate;
(1S)-1-{[ethyl(1H-tetrazol-5-ylmethyl)amino]carbonyl}-3-methylbutyl (4-bromophenyl)carbamate;
(1S)-1-{[ethyl(1H-tetrazol-5-ylmethyl)amino]carbonyl}-3-methylbutyl [4-(trifluoromethyl)phenyl]carbamate;
(1S)-1-[({2-[(tert-butoxycarbonyl)amino]ethyl}amino)carbonyl]-3-methylbutyl (4-bromophenyl)carbamate;
tert-Butyl {[(2S)-2-({[(4-bromophenyl)amino]carbonyl}oxy)-3-phenylpropanoyl]amino}acetate;
(1S)-1-benzyl-2-oxo-2-[(1H-tetrazol-5-ylmethyl)amino]ethyl (4-bromophenyl)carbamate;
tert-Butyl {[(2S)-2-({[(4-bromophenyl)amino]carbonyl}oxy)-3-phenylpropanoyl](methyl)amino}acetate;
[{(2S)-4-methyl-2-[({[4-(trifluoromethyl)phenyl]amino}carbonyl)oxy]pentanoyl}(propyl)amino]acetic acid;

(Isopropyl{(2S)-4-methyl-2-[({[4-(trifluoromethyl)phenyl]amino}carbonyl) oxy]pentanoyl}amino)acetic acid;

(1S)-1-{[(2-aminoethyl)amino]carbonyl}-3-methylbutyl (4-bromophenyl) carbamate;

{[(2S)-2-({[(4-bromophenyl)amino]carbonyl}oxy)-3-phenylpropanoyl]amino}acetic acid;

{[(2S)-2-({[(4-Bromophenyl)amino]carbonyl}oxy)-3-phenylpropanoyl](methyl)amino}acetic acid; and (1S)-1-{[(2-{[(Dimethylamino)sulfonyl]amino}ethyl)amino]carbonyl}-3-methylbutyl (4-bromophenyl)carbamate;

and enantiomers, diastereomers and tautomer thereof;

and salts, including pharmaceutically acceptable salts, of any of the foregoing.

In embodiment (13), there is provided a compound selected from the group consisting of:

(S)-tert-Butyl 2-(((4-Bromophenyl)carbamoyl)oxy)-4-methylpentanoate;

(2S)-2-{[(4-Bromophenyl)carbamoyl]oxy}-4-methylpentanoic acid;

tert-Butyl (2S)-4-Methyl-2-({[4-(trifluoromethyl)phenyl]carbamoyl}oxy)pentanoate;

(2S)-4-Methyl-2-({[4-(Trifluoromethyl)phenyl]carbamoyl}oxy)pentanoic acid; tert-Butyl (2S)-2-({[(4-bromophenyl)amino]carbonyl}oxy)-3-phenyl propanoate; and (2S)-2-({[(4-bromophenyl)amino]carbonyl}oxy)-3-phenylpropanoic acid;

and enantiomers, diastereomers and tautomers thereof;
and salts of the foregoing.

In embodiment (14), there is provided a pharmaceutical composition comprising as active ingredient a therapeutically effective amount of a compound according to any one of embodiments (1) through (13), and a pharmaceutically acceptable adjuvant, diluent or carrier.

In embodiment (15), there is provided a method of treating an ocular inflammatory disease or condition in a subject in need of such treatment, the method comprising administering to the subject a pharmaceutical composition comprising a therapeutically effective amount of a compound according to any one of embodiments (1) through (13).

In embodiment (16), there is provided the method according to embodiment (15), wherein the ocular inflammatory disease or condition is selected from: uveitis, dry eye, keratitis, allergic eye disease, infectious keratitis, herpetic keratitis, corneal angiogenesis, lymphangiogenesis, retinitis, choroiditis, acute multifocal placoid pigment epitheliopathy, Behcet's disease, post-surgical corneal wound healing, post-cataract surgical inflammation, wet and dry age-related macular degeneration (ARMD).

In embodiment (17), there is provided a method of treating dermal inflammation or a dermal disease in a subject in need of such treatment, the method comprising administering to the subject a pharmaceutical composition comprising a therapeutically effective amount of a compound according to any one of embodiments (1) through (13).

In embodiment (18), there is provided the method according to embodiment (17), wherein the dermal inflammation or disease is selected from: dermal wound healing, hypertrophic scars, keloids, burns, rosacea, atopic dermatitis, acne, psoriasis, seborrheic dermatitis, actinic keratoses, basal cell carcinoma, squamous cell carcinoma, melanoma, viral warts, photoaging, photodamage, melasma, post-inflammatory hyperpigmentation, disorders of pigmentation and alopecia (scarring and non-scarring forms).

As will be evident to those skilled in the art, individual diastereoisomeric forms can be obtained by separation of mixtures thereof in conventional manner; chromatographic separation may be employed.

Compound names were generated with ACD Labs version 12.5. Some of the intermediate and reagent names used in the examples were generated with software such as Chem Bio Draw Ultra version 12.0 or Auto Nom 2000 from MDL ISIS Draw 2.5 SP1.

In general, characterization of the compounds is performed according to the following methods. NMR spectra are recorded on a 300 or 600 MHz Varian NMR spectrometer and acquired at room temperature. Chemical shifts are given in ppm referenced either to internal TMS or to the solvent signal. Most of the compounds of Formula I were obtained as rotamers.

All the reagents, solvents, catalysts for which the synthesis is not described are purchased from chemical vendors such as Sigma Aldrich, Fluka, Bio-Blocks, Combi-blocks, TCI, VWR, Lancaster, Oakwood, Trans World Chemical, Alfa, Fisher, Maybridge, Frontier, Matrix, Ukrorgsynth, Toronto, Ryan Scientific, SiliCycle, Anaspec, Syn Chem, Chem-Impex, MIC-scientific, Ltd; however, some known intermediates were prepared according to published procedures.

Usually the compounds of the invention were purified by medium pressure liquid chromatography, unless noted otherwise.

Example 1

Intermediate 1

(S)-tert-Butyl 2-(((4-Bromophenyl)carbamoyl)oxy)-4-methylpentanoate

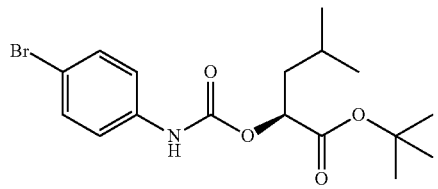 [SMILES: CC(C)C[C@H](OC(=O)Nc1ccc(Br)cc1)C(=O)OC(C)(C)C]

To a solution of (2S)-2-hydroxy-4-methyl-pentanoic acid, 1,1-dimethyl ethyl ester (1.10 g, 5.85 mmol) and 25 mL of methylene chloride at 25° C. was added 4-bromo-phenyl isocyanate (1.15 g, 5.85 mmol) and triethylamine (1.22 mL, 8.78 mmol). The resulting mixture was stirred at 25° C. for 4 hours. The mixture was concentrated and the residue was purified by medium pressure liquid chromatography on silica gel using ethyl acetate:hexane (8:92) to yield Intermediate 1 as viscous oil.

$^1$H NMR (CD$_3$OD, 300 MHz) δ: 7.33-7.47 (m, 4H), 4.87 (m, 1H), 1.56-1.91 (m, 1H), 1.47 (s, 9H), 0.93-1.04 (m, 6H).

Intermediate 2 tert-Butyl (2S)-4-Methyl-2-[({[4-(trifluoromethyl)phenyl]carbamoyl}oxy]pentanoate

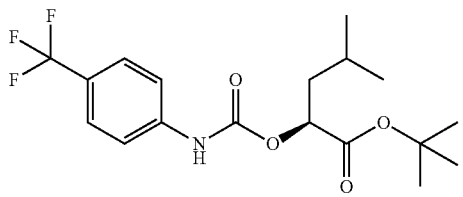 [SMILES: CC(C)C[C@H](OC(=O)Nc1ccc(C(F)(F)F)cc1)C(=O)OC(C)(C)C]

Intermediate 2 was prepared from the corresponding alpha-hydroxy carboxylic acid ester in a similar manner to the procedure described in Example 1 for Intermediate 1. Intermediate 2 was obtained as white solid; $^1$H NMR (CD$_3$OD 300 MHz) δ: 7.52-7.67 (m, 4H), 4.89 (m, 1H), 1.71-1.92 (m, 2H), 1.58-1.70 (m, 1H), 1.47 (s, 9H), 0.98 (t, J=6.2 Hz, 6H).

Example 2

Intermediate 3

(2S)-2-([[(4-Bromophenyl)carbamoyl]oxy)-4-methylpentanoic acid

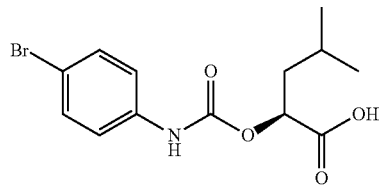 [SMILES: CC(C)C[C@H](OC(=O)Nc1ccc(Br)cc1)C(=O)O]

A solution of Intermediate 1 (1.53 g, 3.98 mmol) and 20 mL of formic acid was stirred at 25° C. for 5 hours. The resulting mixture was quenched with water (20 mL) then extracted with ethyl acetate. The organic layer was washed with water, brine, dried over Na$_2$SO$_4$, filtered, and the filtrate was concentrated under reduced pressure. The residue was rinsed 4 times with methylene chloride:hexane (1:9) to yield Intermediate 3 as white solid; $^1$H NMR (CD$_3$OD, 300 MHz) δ: 7.33-7.45 (m, 4H), 4.94-5.04 (m, 1H), 1.73-1.95 (m, 2H), 1.63-1.73 (m, 1H), 0.98 (dd, J=6.6, 3.7 Hz, 6H).

Intermediate 4

(2S)-4-Methyl-2-[({[4-(trifluoromethyl)phenyl]carbamoyl}oxy]pentanoic acid

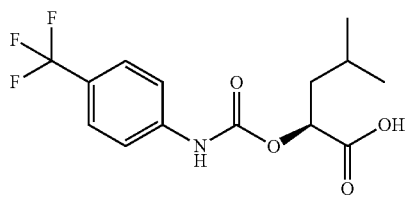 [SMILES: CC(C)C[C@H](OC(=O)Nc1ccc(C(F)(F)F)cc1)C(=O)O]

Intermediate 4 was prepared from the corresponding carbamate derivative in a similar manner to the procedure described in Example 2 for Intermediate 3. Intermediate 4 was obtained as white solid; $^1$H NMR (CD$_3$OD 300 MHz) δ: 7.60-7.66 (m, 2H), 7.53-7.59 (m, 2H), 5.02 (dd, J=9.2, 3.7 Hz, 1H), 1.76-1.91 (m, 2H), 1.66-1.75 (m, 1H), 0.99 (dd, J=6.3, 3.4 Hz, 6H).

Example 3

Compound 1 tert-Butyl {[(2S)-2-{[(4-Bromophenyl)carbamoyl]oxy}-4-methyl pentanoyl]amino}acetate

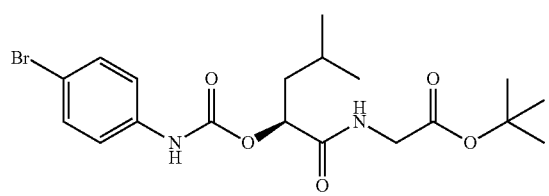 [SMILES: CC(C)C[C@H](OC(=O)Nc1ccc(Br)cc1)C(=O)NCC(=O)OC(C)(C)C]

To a solution of Intermediate 3 (300 mg, 0.911 mmol) and 12 mL of anhydrous DMF at 25° C. was added EDCI (262 mg, 1.37 mmol), HOBt (185 mg, 1.37 mmol), glycine tert-butyl ester (179 mg, 1.37 mmol), and N-methylmorpholine (184 mg, 1.82 mmol). The resulting mixture was stirred at 25° C. for 12 hours. The mixture was quenched with water (5 mL), and the product was extracted with ethyl acetate (40 mL). The layers were separated, and the organic layer was washed with water, brine, dried over Na$_2$SO$_4$, filtered, and the filtrate was concentrated under reduced pressure. The resulting product was purified by medium pressure liquid chromatography on silica gel using ethyl acetate:hexane (1:4) to yield Compound 1 as white solid; $^1$H NMR (CD$_3$OD, 300 MHz) δ: 7.34-7.46 (m, 4H), 5.10 (dd, J=9.5, 4.0 Hz, 1H), 3.75-3.94 (m, 2H), 1.73-1.92 (m, 2H), 1.60-1.72 (m, 1H), 1.45 (s, 9H), 0.99 (s, 3H), 0.97 (s, 3H).

Compounds 2, 3, 4, 5, 6, 7 and 8 were prepared from the corresponding carbamate derivative in a similar manner to the procedure described in Example 3 for Compound 1. Specifically, Compounds 3, 4, 7 and 8 were prepared from Intermediate 3, and compounds 2, 5 and 6 were prepared from Intermediate 4. Compounds 2, 3, 4, 5, 6, 7 and 8 were obtained as white solids; their characteristics are described below in Table 1.

TABLE 1

| Comp. number | IUPAC name Structure | ¹H NMR δ (ppm) |
|---|---|---|
| 2 | tert-Butyl {[(2S)-4-Methyl-2-({[4-(trifluoromethyl)phenyl]carbamoyl}oxy)pentanoyl]amino} acetate | ¹H NMR (CD$_3$OD, 300 MHz) δ: 7.61-7.66 (m, 2H), 7.54-7.60 (m, 2H), 5.12 (dd, J = 9.8, 3.7 Hz, 1H), 3.75-3.95 (m, 2H), 1.75-1.93 (m, 2H), 1.69 (dd, J = 9.5, 4.8 Hz, 1H), 1.45 (s, 9H), 1.00 (s, 3H), 0.98 (s, 3H). |
| 3 | tert-Butyl {[(2S)-2-{[(4-Bromophenyl)carbamoyl]oxy}-4-methylpentanoyl](methyl)amino} acetate | ¹H NMR (CD$_3$OD, 300 MHz) δ: 7.31-7.47 (m, 4H), 5.42 (d, J = 10.8 Hz, 1H), 4.19-4.36 (m, 1H), 3.80 (m, 1H), 3.19 (s, 3H), 1.70-1.97 (m, 2H), 1.52-1.67 (m, 1H), 1.46 (s, 9H), 1.01 (d, J = 5.9 Hz, 6H). |
| 4 | (2S)-1-[(2-Hydroxyethyl)(methyl)amino]-4-methyl-1-oxopentan-2-yl (4-bromophenyl)carbamate | ¹H NMR (CD$_3$OD, 300 MHz) δ: 7.98 (s, NH), 7.30-7.45 (m, 4H), 5.30-5.48 (m, 1H), 3.63-3.86 (m, 2H), 3.36-3.62 (m, 2H), 2.98 (s, 3H), 1.71-1.95 (m, 2H), 1.44-1.62 (m, 1H), 0.94-1.06 (m, 6H). |
| 5 | Diethyl ({[(2S)-4-methyl-2-({[4-(Trifluoromethyl)phenyl]carbamoyl}oxy)pentanoyl]amino} methyl)phosphonate | ¹H NMR (CD$_3$OD, 300 MHz) δ: 7.50-7.69 (m, 4H), 5.04-5.15 (m, 1H), 4.04-4.20 (m, 4H), 3.58-3.87 (m, 2H), 1.72-1.93 (m, 2H), 1.55-1.69 (m, 1H), 1.22-1.38 (m, 6H), 1.00 (s, 3H), 0.98 (s, 3H). |
| 6 | (2S)-1-[(2-Hydroxyethyl)amino]-4-Methyl-1-oxopentan-2-yl [4-(trifluoromethyl)phenyl]carbamate | ¹H NMR (CD$_3$OD, 300 MHz) δ: 7.51-7.68 (m, 4H), 5.07 (dd, J = 9.4, 3.5 Hz, 1H), 3.55-3.66 (m, 2H), 3.32-3.38 (m, 2H), 1.80 (m, 2H), 1.56-1.70 (m, 1H), 0.99 (s, 3H), 0.97 (s, 3H). |
| 7 | (2S)-1-[(2-Hydroxyethyl)amino]-4-methyl-1-oxopentan-2-yl (4-bromophenyl)carbamate | ¹H NMR (CD$_3$OD, 300 MHz) δ: 7.32-7.46 (m, 4H), 5.05 (dd, J = 9.7, 3.5 Hz, 1H), 3.54-3.65 |

TABLE 1-continued

| Comp. number | IUPAC name Structure | $^1$H NMR δ (ppm) |
|---|---|---|
| | ![structure with Br-phenyl carbamate, methylpentanoyl, ethanolamine] | (m, 2H), 3.32-3.38 (m, 2H), 1.70-1.90 (m, 2H), 1.56-1.69 (m, 1H), 0.98 (s, 3H), 0.96 (s, 3H). |
| 8 | Diethyl ({[(2S)-2-{[(4-bromophenyl)carbamoyl]oxy}-4-methylpentanoyl]amino}methyl)phosphonate <br><br>![structure] | $^1$H NMR (CD$_3$OD, 300 MHz) δ: 8.35 (br. s., NH), 7.33-7.46 (m, 4H), 5.01-5.12 (m, 1H), 4.04-4.22 (m, 4H), 3.59-3.89 (m, 2H), 1.69-1.92 (m, 2H), 1.55-1.67 (m, 1H), 1.24-1.35 (m, 6H), 0.99 (s, 3H), 0.97 (s, 3H). |

Example 4

Compound 9 tert-Butyl {[(2S)-2-{[(4-Bromophenyl)carbamoyl]oxy}-4-methylpentanoyl](propyl)amino}acetate

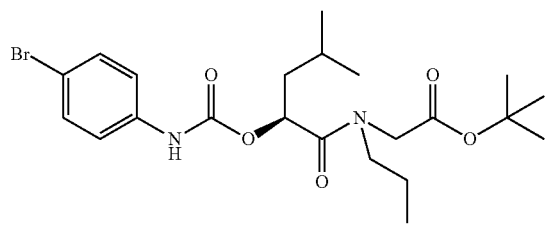 [SMILES: CCCN(CC(=O)OC(C)(C)C)C(=O)[C@H](CC(C)C)OC(=O)Nc1ccc(Br)cc1]

A solution of Intermediate 3 (170 mg, 0.52 mmol), DCC (106 mg, 0.52 mmol) and 14 mL of anhydrous dichloromethane was stirred at 25° C. for 12 hours. The mixture was filtered. The filtrate was quenched with 10% HCl (5 mL), and the product was extracted with ethyl acetate (20 mL). The layers were separated, and the organic layer was washed with water, brine, dried over Na$_2$SO$_4$, filtered, and the filtrate was concentrated under reduced pressure. The resulting product was purified by medium pressure liquid chromatography on silica gel using ethyl acetate:hexane (15:85) to yield Compound 9 as a white solid; $^1$H NMR (CD$_3$OD, 300 MHz) δ: 7.30-7.47 (m, 4H), 5.39 (d, J=11.1 Hz, 1H), 4.19 (d, J=17.0 Hz, 1H), 3.75 (d, J=17.0 Hz, 1H), 3.38 (t, J=7.5 Hz, 2H), 1.66-1.95 (m, 3H), 1.52-1.64 (m, 2H), 1.44 (s, 9H), 0.91-1.07 (m, 9H).

Compounds 10, 11, 12, 13, 14, 15, 16 and 17 were prepared from the corresponding carbamate derivative in a similar manner to the procedure described in Example 4 for Compound 9. Specifically, Compounds 10, 11, 14 and 16 were prepared from Intermediate 3, and Compounds 12, 13, 15 and 17 were prepared from Intermediate 4. Compound 10, 11, 12, 13, 14, 15, 16 and 17 were each obtained as a white solid; their characteristics are described below in Table 2.

TABLE 2

| Cmpd. number | IUPAC name Structure | $^1$H NMR δ (ppm) |
|---|---|---|
| 10 | tert-Butyl {[(2S)-2-{[(4-Bromophenyl)carbamoyl]oxy}-4-methylpentanoyl](propan-2-yl)amino}acetate <br><br>![structure] | $^1$H NMR (CD$_3$OD, 300 MHz) δ: 7.31-7.44 (m, 4H), 5.46 (d, J = 9.1 Hz, 1H), 4.19-4.36 (m, 1H), 3.94-4.04 (m, 1H), 3.67-3.79 (m, 1H), 1.75-1.94 (m, 2H), 1.58 (m, 1H), 1.43 (s, 9H), 1.21-1.34 (m, 6H), 0.94-1.05 (m, 6H). |

TABLE 2-continued

| Cmpd. number | IUPAC name Structure | $^1$H NMR δ (ppm) |
|---|---|---|
| 11 | tert-Butyl {[(2S)-2-{[(4-Bromophenyl)carbamoyl]oxy}-4-methylpentanoyl](ethyl)amino} acetate 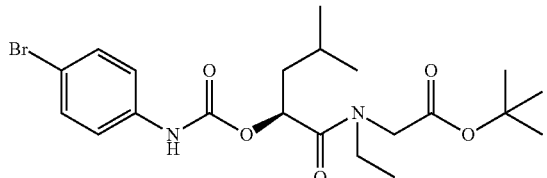 | $^1$H NMR (CD$_3$OD, 300 MHz) δ: 7.38 (s, 4H), 5.39 (d, J = 10.3 Hz, 1H), 4.19 (d, J = 17.0 Hz, 1H), 3.75 (d, J = 16.7 Hz, 1H), 3.42-3.58 (m, 2H), 1.76-1.95 (m, 2H), 1.53-1.66 (m, 1H), 1.45 (s, 9H), 1.23-1.37 (m, 3H), 0.93-1.06 (m, 6H). |
| 12 | tert-Butyl {Methyl[(2S)-4-methyl-2-({[4-(trifluoromethyl)phenyl]carbamoyl}oxy)pentanoyl]amino} acetate 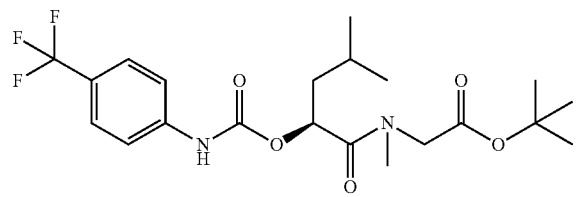 [SMILES: CC(C)C[C@H](OC(=O)Nc1ccc(C(F)(F)F)cc1)C(=O)N(C)CC(=O)OC(C)(C)C] | $^1$H NMR (CD$_3$OD, 300 MHz) δ: 7.48-7.68 (m, 4H), 5.44 (d, J = 8.2 Hz, 1H), 4.31 (s, 1H), 3.79 (d, J = 17.3 Hz, 1H), 3.21 (s, 3H), 1.74-1.97 (m, 2H), 1.54-1.68 (m, 1H), 1.46 (s, 9H), 0.91-1.07 (m, 6H). |
| 13 | tert-Butyl {Ethyl[(2S)-4-methyl-2-({[4-(trifluoromethyl)phenyl]carbamoyl}oxy)pentanoyl]amino} acetate 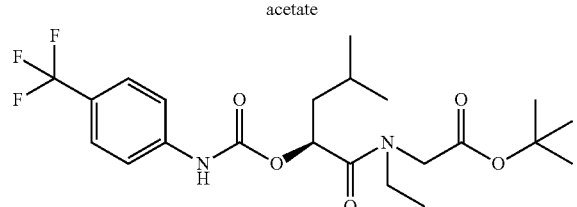 | $^1$H NMR (CD$_3$OD, 300 MHz) δ: 7.49-7.69 (m, 4H), 5.43 (s, 1H), 4.56 (d, J = 18.2 Hz, 1H), 4.20 (d, J = 17.0 Hz, 1H), 3.69-3.85 (m, 1H), 3.42-3.61 (m, 2H), 1.76-2.01 (m, 2H), 1.53-1.70 (m, 1H), 1.45 (s, 9H), 1.23-1.37 (m, 3H), 0.95-1.07 (m, 6H). |
| 14 | (2S)-4-Methyl-1-oxo-1-[(1H-tetrazol-5-ylmethyl)amino]pentan-2-yl (4-bromophenyl)carbamate 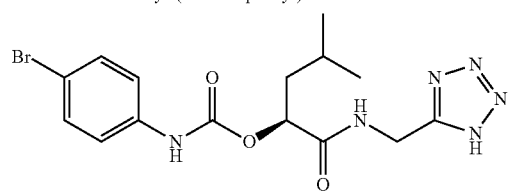 | $^1$H NMR (CD$_3$OD, 300 MHz) δ: 7.33-7.47 (m, 4H), 5.03-5.14 (m, 1H), 4.70 (s, 2H), 1.72-1.90 (m, 2H), 1.66 (m, 1H), 0.98 (s, 3H), 0.96 (s, 3H). |
| 15 | (2S)-4-methyl-1-oxo-1-[(1H-tetrazol-5-ylmethyl)amino]pentan-2-yl [4-(trifluoromethyl)phenyl]carbamate 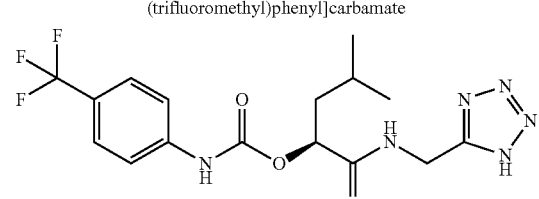 | $^1$H NMR (CD$_3$OD, 300 MHz) δ: 7.98 (s, NH), 7.60 (m, 4H), 5.12 (dd, J = 9.7, 3.2 Hz, 1H), 4.70 (s, 2H), 1.81 (m, 2H), 1.57-1.74 (m, 1H), 0.98 (s, 3H), 0.96 (s, 3H). |

TABLE 2-continued

| Cmpd. number | IUPAC name Structure | $^1$H NMR δ (ppm) |
|---|---|---|
| 16 | (2S)-4-methyl-1-[methyl(1H-tetrazol-5-ylmethyl)amino]-1-oxopentan-2-yl (4-bromophenyl)carbamate | $^1$H NMR (CD$_3$OD, 300 MHz) δ: 7.98 (s, NH), 7.29-7.46 (m, 4H), 5.36 (d, J = 10.3 Hz, 1H), 4.73-5.04 (m, 2H), 2.99 (s, 3H), 1.60-1.97 (m, 2H), 1.25-1.47 (m, 1H), 0.95-1.08 (m, 6H). |
| 17 | (2S)-4-methyl-1-[methyl(1H-tetrazol-5-ylmethyl)amino]-1-oxopentan-2-yl [4-(trifluoromethyl)phenyl]carbamate | $^1$H NMR (CD$_3$OD, 300 MHz) δ: 7.98 (s, NH), 7.50-7.67 (m, 4H), 5.35-5.46 (m, 1H), 4.94-5.04 (m, 1H), 4.73-4.88 (m, 1H), 2.99 (s, 3H), 1.53-1.97 (m, 2H), 1.13-1.46 (m, 1H), 0.91-1.06 (m, 6H). |

Example 5

Compound 18

2-{[(2S)-4-Methyl-2-({[4-(trifluoromethyl)phenyl]carbamoyl}oxy)pentanoyl]amino}ethyl acetate

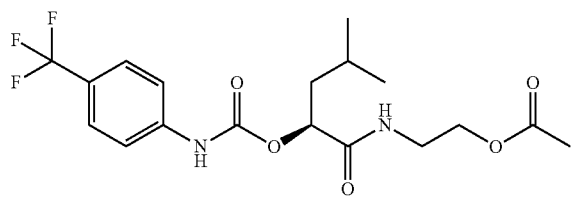 [SMILES: CC(=O)OCCNC(=O)[C@H](CC(C)C)OC(=O)Nc1ccc(C(F)(F)F)cc1]

A solution of Compound 6 (50 mg, 0.14 mmol), 4 mL of anhydrous THF and acetic anhydride (0.014 mL, 0.15 mmol) was stirred at 25° C. for 1 hour. The mixture was concentrated and the resulting product was purified by medium pressure liquid chromatography on silica gel using ethyl acetate:hexane (4:6) to yield Compound 18 as clear oil; $^1$H NMR (CD$_3$OD, 300 MHz) δ: 7.51-7.70 (m, 4H), 5.04 (dd, J=9.1, 3.3 Hz, 1H), 4.05-4.21 (m, 2H), 3.47 (m, 2H), 1.99 (s, 3H), 1.71-1.90 (m, 2H), 1.63 (m, 1H), 0.99 (s, 3H), 0.97 (s, 3H).

Example 6

Compound 19

{[(2S)-2-{[(4-Bromophenyl)carbamoyl]oxy)}-4-methylpentanoyl]amino}acetic acid

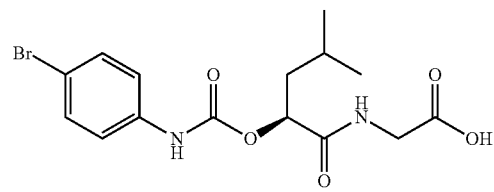 [SMILES: CC(C)C[C@H](OC(=O)Nc1ccc(Br)cc1)C(=O)NCC(=O)O]

A solution of Compound 1 (368 mg, 0.83 mmol) and 8 mL of formic acid was stirred at 25° C. for 12 hours. The resulting reaction was quenched with water (10 mL), and the product was extracted with EtOAc. The organic layer was washed with water, brine, dried over Na$_2$SO$_4$, filtered, and concentrated under reduced pressure. The residue was rinsed four times with acetone:hexane (1:99) to yield Compound 19 as a white solid; $^1$H NMR (CD$_3$OD, 300 MHz) δ: 8.26 (s, 1H), 7.33-7.45 (m, 4H), 5.06-5.17 (m, 1H), 3.84-4.04 (m, 2H), 1.74-1.90 (m, 2H), 1.63-1.74 (m, 1H), 0.99 (s, 3H), 0.97 (s, 3H).

Compounds 20, 21, 22, 23, 24, 25 and 26 were prepared from the corresponding ester derivative in a similar manner to the procedure described in Example 6 for Compound 19. Specifically, Compound 20 was prepared from Compound 2; Compound 21 was prepared from Compound 3; Compound 22 was prepared from Compound 9; Compound 23 was prepared from Compound 10; Compound 24 was prepared from Compound 11; Compound 25 was prepared from Compound 12; and Compound 26 was prepared from Compound 13. Compounds 20, 21, 22, 23, 24, 25 and 26 obtained as white solids; their characteristics are described below in Table 3.

TABLE 3

| Cmpd No. | IUPAC name Structure | $^1$H NMR δ (ppm) |
|---|---|---|
| 20 | {[(2S)-4-Methyl-2-({[4-(trifluoromethyl)phenyl]carbamoyl}oxy)pentanoyl]amino}acetic acid | $^1$H NMR (CD$_3$OD, 300 MHz) δ: 8.31 (br. s., NH), 7.61-7.66 (m, 2H), 7.54-7.60 (m, 2H), 5.14 (dd, J = 9.7, 3.5 Hz, 1H), 3.87-4.02 (m, 2H), 1.76-1.91 (m, 2H), 1.63-1.75 (m, 1H), 1.00 (s, 3H), 0.98 (s, 3H). |
| 21 | {[(2S)-2-{[(4-Bromophenyl)carbamoyl]oxy}-4-methylpentanoyl](methyl)amino}acetic acid | $^1$H NMR (CD$_3$OD, 300 MHz) δ: 7.28-7.45 (m, 4H), 5.43 (d, J = 7.6 Hz, 1H), 4.44 (m, 1H), 3.83 (d, J = 17.3 Hz, 1H), 3.21 (s, 3H), 1.72-1.99 (m, 2H), 1.48-1.68 (m, 1H), 1.02 (d, J = 1.8 Hz, 6H). |
| 22 | {[(2S)-2-{[(4-Bromophenyl)carbamoyl]oxy}-4-methylpentanoyl](propyl)amino}acetic acid | $^1$H NMR (CD$_3$OD, 300 MHz) δ: 7.31-7.47 (m, 4H), 5.39 (d, J = 10.3 Hz, 1H), 4.34 (d, J = 17.3 Hz, 1H), 3.80 (d, J = 17.3 Hz, 1H), 3.35-3.51 (m, 2H), 1.68-1.97 (m, 3H), 1.50-1.66 (m, 2H), 0.91-1.09 (m, 9H). |
| 23 | {[(2S)-2-{[(4-Bromophenyl)carbamoyl]oxy}-4-methylpentanoyl](propan-2-yl)amino}acetic acid | $^1$H NMR (CD$_3$OD, 300 MHz) δ: 7.30-7.45 (m, 4H), 5.46 (dd, J = 10.0, 3.2 Hz, 1H), 4.28 (quin, J = 6.6 Hz, 1H), 4.02-4.16 (m, 1H), 3.82 (d, J = 17.3 Hz, 1H), 1.72-1.98 (m, 2H), 1.48-1.65 (m, 1H), 1.20-1.37 (m, 6H), 0.93-1.03 (m, 6H |
| 24 | {[(2S)-2-{[(4-Bromophenyl)carbamoyl]oxy}-4-methylpentanoyl](ethyl)amino}acetic acid | $^1$H NMR (CD$_3$OD, 300 MHz) δ: 7.38 (m, 4H), 5.40 (d, J = 10.3 Hz, 1H), 4.33 (d, J = 16.7 Hz, 1H), 3.73 (d, J = 16.4 Hz, 1H), 3.38-3.66 (m, 2H), 1.71-1.97 (m, 2H), 1.53-1.69 (m, 1H), 1.22-1.36 (m, 3H), 0.87-1.05 (m, 6H). |

TABLE 3-continued

| Cmpd No. | IUPAC name Structure | $^1$H NMR δ (ppm) |
|---|---|---|
| 25 | {Methyl[(2S)-4-methyl-2-({[4-(trifluoromethyl)phenyl]carbamoyl}oxy)pentanoyl]amino}acetic acid | $^1$H NMR (CD$_3$OD, 300 MHz) δ: 7.49-7.69 (m, 4H), 5.46 (d, J = 10.3 Hz, 1H), 4.44 (s, 1H), 3.81 (d, J = 17.3 Hz, 1H), 3.21 (s, 3H), 1.71-1.98 (m, 2H), 1.50-1.71 (m, 1H), 0.91-1.07 (m, 6H). |
| 26 | {Ethyl[(2S)-4-methyl-2-({[4-(trifluoromethyl)phenyl]carbamoyl}oxy)pentanoyl]amino}acetic acid | $^1$H NMR (CD$_3$OD, 300 MHz) δ: 7.48-7.68 (m, 4H), 5.42 (d, J = 10.84 Hz, 1H), 4.34 (d, J = 17.29 Hz, 1H), 3.82 (d, J = 17.29 Hz, 1H), 3.41-3.65 (m, 2H), 1.74-2.00 (m, 2H), 1.51-1.69 (m, 1H), 1.24-1.38 (m, 3H), 0.86-1.06 (m, 6H). |

Example 7

Compound 27

(2S)-4-Methyl-1-{methyl[2-(sulfooxy)ethyl]amino}-1-oxopentan-2-yl (4-bromophenyl)carbamate

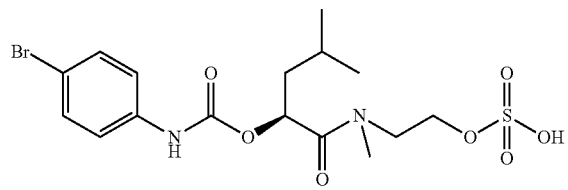 [SMILES: CC(C)C[C@H](OC(=O)Nc1ccc(Br)cc1)C(=O)N(C)CCOS(=O)(=O)O]

To a solution of Compound 4 (166 mg, 0.42 mmol) and 8 mL of anhydrous THF at 25° C. under argon was added Et$_3$N (0.12 mL, 0.84 mmol), DMAP (56 mg, 0.42 mmol), and 2,2,2-trichloroethyl chlorosulfate (205 mg, 0.84 mmol). The resulting mixture was stirred at 25° C. for 12 hours. The mixture was quenched with 10% HCl (2 mL), and the product was extracted with ethyl acetate (20 mL). The layers were separated, and the organic layer was washed with water, brine, dried over Na$_2$SO$_4$, filtered, and the filtrate was concentrated under reduced pressure. The resulting product was purified by medium pressure liquid chromatography on silica gel using methanol:dichloromethane (15:85) to yield Compound 27 as an off white solid; $^1$H NMR (CD$_3$OD, 300 MHz) δ: 7.38 (s, 4H), 5.32-5.44 (m, 1H), 4.08-4.28 (m, 2H), 3.39-3.67 (m, 2H), 3.25 (s, 3H), 1.71-1.96 (m, 2H), 1.50-1.70 (m, 1H), 1.00 (d, J=5.0 Hz, 6H).

Example 8

Compound 28

({(2S)-4-methyl-2-[({[4-(trifluoromethyl)phenyl]amino}carbonyl)oxy]pentanoyl}amino)methanesulfonic acid

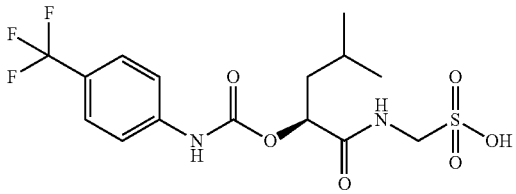 [SMILES: CC(C)C[C@H](OC(=O)Nc1ccc(C(F)(F)F)cc1)C(=O)NCS(=O)(=O)O]

To a solution of Intermediate 4 (750 mg, 2.35 mmol) and 10 mL of DMF at 25° C. was added aminomethane sulfonic acid (260 mg, 2.35 mmol), HATU (983 mg, 2.58 mmol) and diisopropylethylamine (0.49 mL, 2.82 mmol). The resulting mixture was stirred at 100° C. for 12 hours. The mixture was concentrated and quenched with water (4 mL), and the product was extracted with ethyl acetate (20 mL). The layers were separated, and the organic layer was washed with water, brine, dried over Na$_2$SO$_4$, filtered, and the filtrate was concentrated under reduced pressure. The residue was purified by medium pressure liquid chromatography on silica gel using methanol:dichloromethane (15:85) to yield Compound 28 as a white solid; $^1$H NMR (CD$_3$OD, 300 MHz) δ: 7.51-7.69 (m, 4H), 5.18 (dd, J=9.2, 3.7 Hz, 1H), 4.22-4.48 (m, 2H), 1.68-1.91 (m, 3H), 0.99 (s, 3H), 0.98 (s, 3H).

Example 9

Intermediate 2a tert-Butyl (2S)-2-({[(4-bromophenyl)amino]carbonyl}oxy)-3-phenyl propanoate

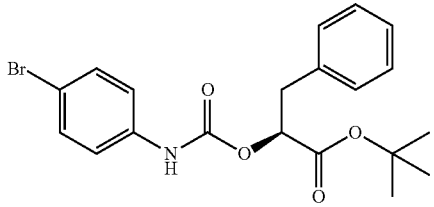 [SMILES: CC(C)(C)OC(=O)[C@H](Cc1ccccc1)OC(=O)Nc1ccc(Br)cc1]

Intermediate 2a was prepared from the corresponding amino acid in a similar manner to the procedure described in Example 1 for Intermediate 1. Intermediate 2a was obtained as clear oil; [α]D=−13.7, (c=1.00, MeOH); $^1$H NMR (CD$_3$OD, 300 MHz) δ: 7.16-7.45 (m, 8H), 5.07 (dd, J=7.3, 5.6 Hz, 1H), 3.09-3.17 (m, 2H), 1.35-1.42 (m, 9H).

Intermediate 4a (2S)-2-({[(4-bromophenyl)amino]carbonyl}oxy)-3-phenylpropanoic acid

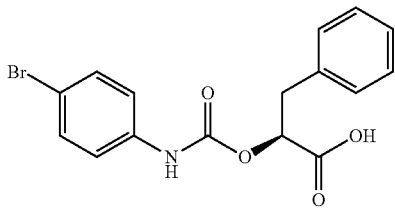 [SMILES: O=C(Nc1ccc(Br)cc1)O[C@@H](Cc1ccccc1)C(=O)O]

Intermediate 4a was prepared from the corresponding carbamate derivative in a similar manner to the procedure described in Example 2 for Intermediate 3. Intermediate 4a was obtained as white solid; [α]D=−13.3, c=1.00, MeOH; $^1$H NMR (CD$_3$OD, 300 MHz) δ: 7.15-7.42 (m, 8H), 5.20 (s, 1H), 3.19-3.30 (m, 1H), 3.05-3.17 (m, 1H).

Compounds 29, 30, 31, 32, 33, 34, 35 and 36 were prepared from the corresponding carbamate derivative in a similar manner to the procedure described in Example 4 for Compound 9. Specifically, Compounds 29, 30 and 32 were obtained from Intermediate 4; Compounds 31 and 33 were obtained from Intermediate 3; and Compounds 34, 35 and 36 were obtained from Intermediate 4a. The characteristics of the compounds so obtained are described below.

Compound 29 tert-Butyl [{(2S)-4-methyl-2-[({[4-(trifluoromethyl)phenyl]amino}carbonyl)oxy]pentanoyl}(propyl)amino]acetate

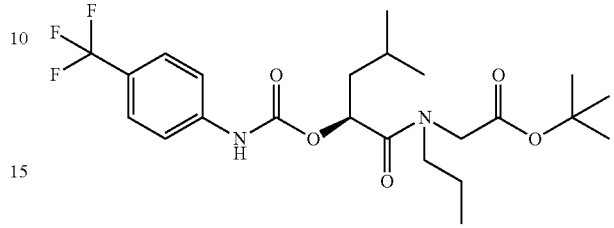

White solid; [α]D=−18.6 (c=1.00, MeOH); $^1$H NMR (CD$_3$OD, 300 MHz) δ: 7.49-7.69 (m, 4H), 5.41 (d, J=10.3 Hz, 1H), 4.20 (d, J=17.3 Hz, 1H), 3.76 (d, J=16.7 Hz, 1H), 3.36-3.45 (m, 1H), 1.83 (m, 3H), 1.56 (m, 2H), 1.45 (s, 9H), 0.88-1.09 (m, 9H); the $^1$H NMR spectrum showed the existence of rotomers.

Compound 30 tert-Butyl (Isopropyl{(2S)-4-methyl-2-[({[4-(trifluoromethyl)phenyl]amino}carbonyl)oxy]pentanoyl}amino)acetate

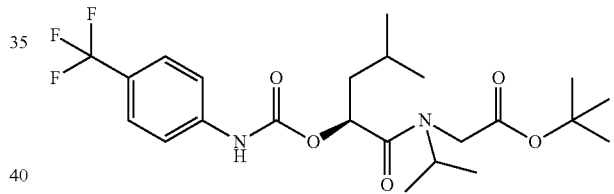

White solid; [α]D=−22.3 (c=1.00, MeOH); $^1$H NMR (CD$_3$OD, 300 MHz) δ: 7.51-7.67 (m, 4H), 5.49 (d, J=10.0 Hz, 1H), 4.20-4.35 (m, 1H), 3.89-4.05 (m, 1H), 3.69-3.80 (m, 1H), 1.77-1.98 (m, 2H), 1.54-1.68 (m, 1H), 1.44 (s, 9H), 1.21-1.35 (m, 6H), 0.91-1.06 (m, 6H); the $^1$H NMR spectrum showed the existence of rotomers.

Compound 31

(1S)-1-{[ethyl(1H-tetrazol-5-ylmethyl)amino]carbonyl}-3-methybutyl (4-bromophenyl)carbamate

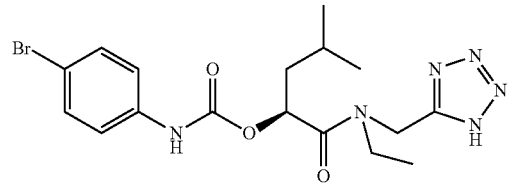 [SMILES: CCN(Cc1nnn[nH]1)C(=O)[C@H](CC(C)C)OC(=O)Nc1ccc(Br)cc1]

White solid; [α]D=−12.6 (c=1.00, MeOH); $^1$H NMR (CD$_3$OD, 300 MHz) δ: 7.27-7.47 (m, 4H), 5.34 (m, 1H), 5.00 (d, J=15.8 Hz, 1H), 4.70 (d, J=15.8 Hz, 1H), 3.54-3.71

(m, 2H), 1.72-1.96 (m, 2H), 1.54 (m, 1H), 1.35 (t, J=7.2 Hz, 3H), 0.90-1.07 (m, 6H); the ¹H NMR spectrum showed the existence of rotomers.

Compound 32

(1S)-1-{[ethyl(1H-tetrazol-5-ylmethyl)amino]carbonyl}-3-methylbutyl [4-(trifluoromethyl)phenyl]carbamate

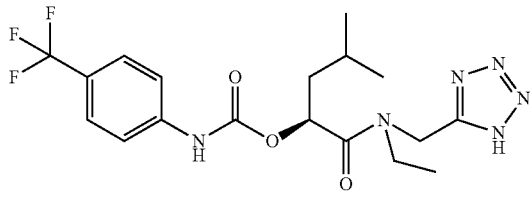 [SMILES: CCN(Cc1nnn[nH]1)C(=O)[C@H](CC(C)C)OC(=O)Nc1ccc(C(F)(F)F)cc1]

White solid; [α]D=−9.1 (c=1.00, MeOH); ¹H NMR (CD₃OD, 300 MHz) δ: 7.51-7.69 (m, 4H), 7.43 (s, NH), 5.28-5.44 (m, 1H), 5.08 (d, J=14.9 Hz, 1H), 4.56-4.69 (m, 1H), 3.48-3.64 (m, 1H), 1.70-1.98 (m, 2H), 1.58 (m, 1H), 1.23-1.42 (m, 3H), 0.93-1.07 (m, 6H); the ¹H NMR spectrum showed the existence of rotomers.

Compound 33

(1S)-1-({2-[(tert-butoxycarbonyl)amino]ethyl}amino)carbonyl-3-methylbutyl (4-bromophenyl)carbamate

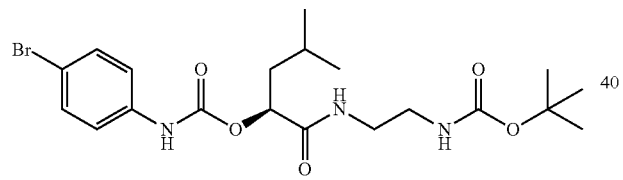

White solid; [α]D=−12.4 (c=1.00, MeOH); ¹H NMR (CD₃OD, 300 MHz) δ: 7.40 (s, 4H), 4.94-5.06 (m, 1H), 3.24-3.31 (m, 2H), 3.17 (m, 2H), 1.79 (m, 2H), 1.55-1.69 (m, 2H), 1.40 (s, 9H), 0.97 (d, J=6.4 Hz, 6H).

Compound 34 tert-Butyl {[(2S)-2-({[(4-bromophenyl)amino]carbonyl}oxy)-3-phenylpropanoyl]amino}acetate

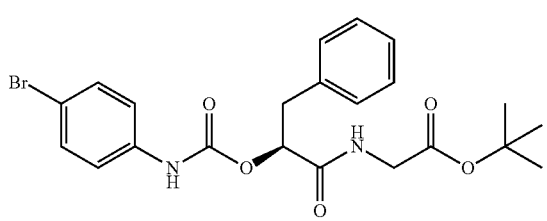 [SMILES: CC(C)(C)OC(=O)CNC(=O)[C@H](Cc1ccccc1)OC(=O)Nc1ccc(Br)cc1]

White solid; [α]D=−23.0 (c=1.00, MeOH); ¹H NMR (CD₃OD, 300 MHz) δ: 7.15-7.43 (m, 8H), 5.27 (s, 1H), 3.84 (d, J=7.6 Hz, 2H), 3.02-3.29 (m, 2H), 1.46 (s, 9H).

Compound 35

(1S)-1-benzyl-2-oxo-2-[(1H-tetrazol-5-ylmethyl)amino]ethyl (4-bromophenyl)carbamate

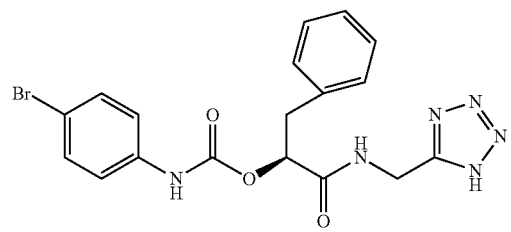 [SMILES: O=C(Nc1ccc(Br)cc1)O[C@@H](Cc1ccccc1)C(=O)NCc1nnn[nH]1]

Off white solid; ¹H NMR (CD₃OD, 300 MHz) δ: 7.18-7.41 (m, 9H), 5.22 (m., 1H), 4.66-4.85 (m, 2H), 3.15-3.26 (m, 2H).

Compound 36 tert-Butyl {[(2S)-2-({[(4-bromophenyl)amino]carbonyl})oxy)-3-phenylpropanoyl](methyl)amino}acetate

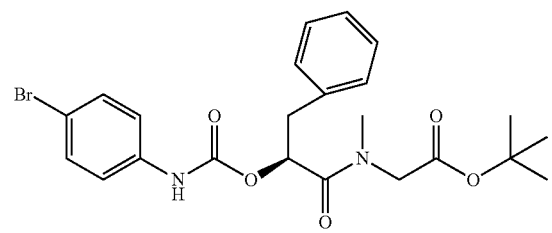 [SMILES: CN(CC(=O)OC(C)(C)C)C(=O)[C@H](Cc1ccccc1)OC(=O)Nc1ccc(Br)cc1]

White solid; [α]D=−18.3 (c=1.00, MeOH); ¹H NMR (CD₃OD, 300 MHz) δ: 7.20-7.45 (m, 9H), 5.57 (dd, J=8.4, 5.4 Hz, 1H), 4.02-4.15 (m, 2H), 3.18 (m, 2H), 3.16 (S, 3H), 1.40-1.53 (m, 9H).

Compounds 37, 38, 39, 40 and 41 were prepared from the corresponding ester derivative in a similar manner to the procedure described in Example 6 for Compound 19. Specifically, Compound 37 was obtained from Compound 29; Compound 38 was obtained from Compound 30; Compound 39 was obtained from Compound 33; Compound 40 was obtained from Compound 34; and Compound 41 was obtained from Compound 36. The characteristics of the compounds so obtained are described below.

Compound 37

[{(2S)-4-methyl-2-[({[4-(trifluoromethyl)phenyl]amino}carbonyl)oxy]pentanoyl}propyl)amino]acetic acid

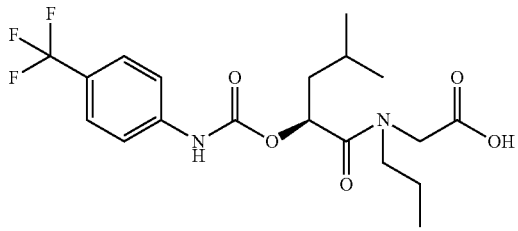 [SMILES: CCCN(CC(=O)O)C(=O)[C@H](CC(C)C)OC(=O)Nc1ccc(C(F)(F)F)cc1]

White solid; [α]D=−10.3 (c=1.00, MeOH); ¹H NMR (CD₃OD, 300 MHz) δ: 7.49-7.68 (m, 4H), 5.42 (d, J=10.8 Hz, 1H), 4.34 (d, J=17.3 Hz, 1H), 3.81 (d, J=17.3 Hz, 1H), 3.36-3.57 (m, 1H), 1.62-1.98 (m, 3H), 1.61-1.48 (m, 2H), 0.81-1.08 (m, 9H); the ¹H NMR spectrum showed the existence of rotomers.

Compound 38

(Isopropyl{(2S)-4-methyl-2-[({[4-(trifluoromethyl)phenyl]amino}carbonyl) oxy]pentanoyl}amino)acetic acid

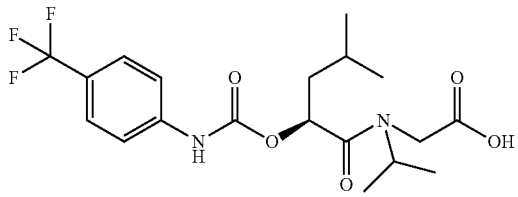 [SMILES: CC(C)C[C@H](OC(=O)Nc1ccc(C(F)(F)F)cc1)C(=O)N(CC(=O)O)C(C)C]

White solid; [α]D=−9.5 (c=1.00, MeOH); ¹H NMR (CD₃OD, 300 MHz) δ: 7.47-7.68 (m, 4H), 5.50 (d, J=9.7 Hz, 1H), 4.20-4.41 (m, 1H), 3.96-4.17 (m, 1H), 3.82 (d, J=17.3 Hz, 1H), 1.73-2.03 (m, 2H), 1.61 (m, 1H), 1.29 (m, 6H), 0.83-1.16 (m, 6H); the ¹H NMR spectrum showed the existence of rotomers.

Compound 39

(1S)-1-{[(2-aminoethyl)amino]carbonyl}-3-methylbutyl (4-bromophenyl) carbamate

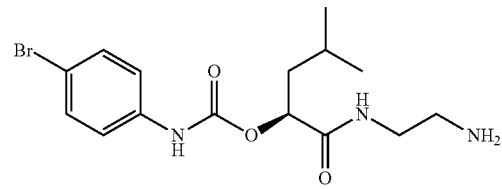 [SMILES: CC(C)C[C@H](OC(=O)Nc1ccc(Br)cc1)C(=O)NCCN]

White solid; [α]D=−9.8 (c=1.00, MeOH); ¹H NMR (CD₃OD, 300 MHz) δ: 7.32-7.47 (m, 4H), 4.94-5.03 (m, 1H), 3.48 (m, 2H), 2.99-3.10 (m, 2H), 1.54-1.90 (m, 3H), 0.94-1.02 (m, 6H).

Compound 40

{[(2S)-2-({[(4-bromophenyl)amino]carbonyl})oxy)-3-phenylpropanoyl]amino}acetic acid

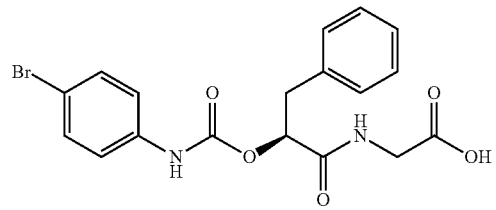 [SMILES: O=C(O)CNC(=O)[C@H](Cc1ccccc1)OC(=O)Nc1ccc(Br)cc1]

White solid; [α]D=−13.1 (c=1.00, MeOH); ¹H NMR (CD₃OD, 300 MHz) δ: 7.15-7.43 (m, 8H), 5.30 (dd, J=8.6, 4.2 Hz, 1H), 3.84-4.02 (m, 2H), 3.01-3.29 (m, 2H).

Compound 41

{[(2S)-2-({[(4-Bromophenyl)amino]carbonyl}oxy)-3-phenylpropanoyl](methyl)amino}acetic acid

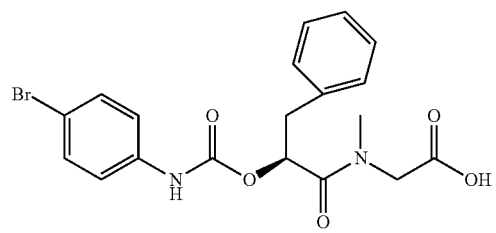 [SMILES: CN(CC(=O)O)C(=O)[C@H](Cc1ccccc1)OC(=O)Nc1ccc(Br)cc1]

White solid; [α]D=−16.1 (c=1.00, MeOH); ¹H NMR (CD₃OD, 300 MHz) δ: 7.21-7.40 (m, 9H), 5.58 (dd, J=8.5, 5.3 Hz, 1H), 4.28 (d, J=17.3 Hz, 1H), 3.91 (d, J=17.3 Hz, 1H), 3.03-3.21 (m, 5H).

Compound 42

(1S)-1-{[(2-{[(Dimethylamino)sulfonyl]amino}ethyl)amino]carbonyl}-3-methylbutyl (4-bromophenyl)carbamate

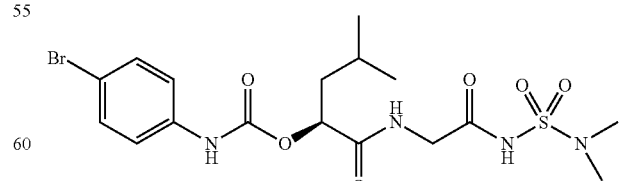

A solution of Compound 39 (78 mg, 0.19 mmol) in 14 mL of anhydrous THF, N,N-dimethylsulfomoyl chloride (33 mg, 0.23 mmol) and Et₃N (48 mg, 0.48 mmol) 14 mL was stirred at 25° C. for 12 hours. The mixture was quenched with water (2 mL), extracted with ethyl acetate (10 mL). The organic layer was washed with water, brine, dried over Na$_2$SO$_4$, filtered, and the filtrate was concentrated under reduced pressure. The resulting product was purified by medium pressure liquid chromatography on silica gel using ethyl acetate:hexane (8:2) to yield Compound 42 as white solid; $^1$H NMR (CD3OD, 600 MHz) δ: 7.32-7.47 (m, 4H), 4.97-5.07 (m, 1H), 3.32 (m, 2H), 3.07-3.19 (m, 2H), 1.73-1.89 (m, 2H), 1.64 (m, 1H), 0.97 (d, J=6.2 Hz, 6H).

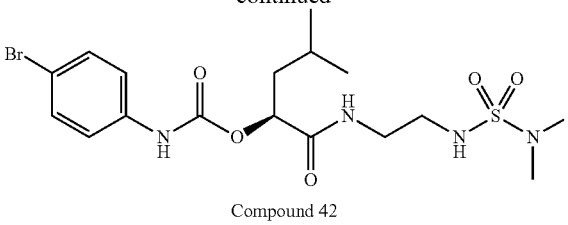

Compound 42

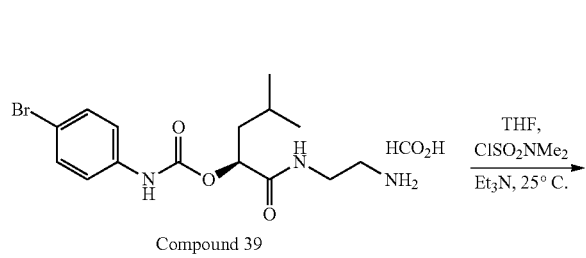

Compound 39

Biological Data

Biological activity of compounds according to Formula I is set forth in Table 4 below. CHO-Gα16 cells stably expressing FPR2 were cultured in (F12, 10% FBS, 1% PSA, 400 μg/ml geneticin and 50 μg/ml hygromycin) and HEK-Gqi5 cells stable expressing FPR1 were cultured in (DMEM high glucose, 10% FBS, 1% PSA, 400 μg/ml geneticin and 50 μg/ml hygromycin). In general, the day before the experiment, 18,000 cells/well were plated in a 384-well clear bottom poly-D-lysine coated plate. The following day the screening compound-induced calcium activity was assayed on the FLIPR$^{Tetra}$. The drug plates were prepared in 384-well microplates using the EP3 and the MultiPROBE robotic liquid handling systems. Compounds were tested at concentrations ranging from 0.61 to 10,000 nM. Results are expressed as EC$_{50}$ (nM) and % efficacy values.

TABLE 4

| Compound No. | Structure/ IUPAC name | FPR2 Gα16- CHO EC$_{50}$ (% eff) |
|---|---|---|
| 1 | tert-Butyl {[(2S)-2-{[(4-Bromophenyl)carbamoyl]oxy}-4-methyl pentanoyl]amino}acetate | 526 nM (0.89) |
| 2 | tert-Butyl {[(2S)-4-Methyl-2-({[4-(trifluoromethyl)phenyl]carbamoyl}oxy)pentanoyl]amino}acetate | 2017 nM (1.12) |
| 3 | tert-Butyl {[(2S)-2-{[(4-Bromophenyl)carbamoyl]oxy}-4-methylpentanoyl](methyl)amino}acetate | 109 nM (1.01) |

TABLE 4-continued

| Compound No. | Structure/ IUPAC name | FPR2 Gα16-CHO EC$_{50}$ (% eff) |
|---|---|---|
| 4 | 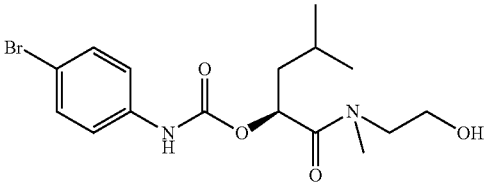 [SMILES: CC(C)C[C@H](OC(=O)Nc1ccc(Br)cc1)C(=O)N(C)CCO]<br>(2S)-1-[(2-Hydroxyethyl)(methyl)amino]-4-methyl-1-oxopentan-2-yl (4-bromophenyl)carbamate | 59 nM (0.97) |
| 5 | 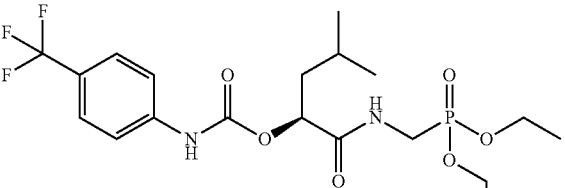<br>Diethyl ({[(2S)-4-methyl-2-({[4-(Trifluoromethyl)phenyl]carbamoyl}oxy)pentanoyl]amino}methyl)phosphonate | 6.7 nM (1.01) |
| 6 | 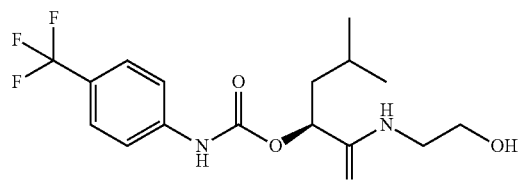<br>(2S)-1-[(2-Hydroxyethyl)amino]-4-Methyl-1-oxopentan-2-yl [4-(trifluoromethyl)phenyl]carbamate | 146 nM (0.75) |
| 7 | 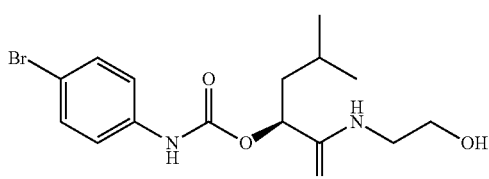<br>(2S)-1-[(2-Hydroxyethyl)amino]-4-methyl-1-oxopentan-2-yl (4-bromophenyl)carbamate | 35 nM (0.98) |
| 8 | 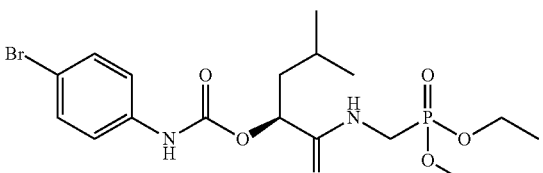<br>Diethyl ({[(2S)-2-{[(4-bromophenyl)carbamoyl]oxy}-4-methylpentanoyl]amino}methyl)phosphonate | 1.8 nM (1.00) |
| 9 | 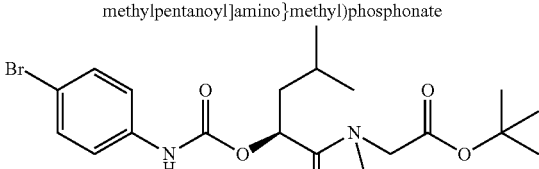<br>tert-Butyl {[(2S)-2-{[(4-Bromophenyl)carbamoyl]oxy}-4-methylpentanoyl](propyl)amino}acetate | 4.4 nM (1.04) |

TABLE 4-continued

| Compound No. | Structure/ IUPAC name | FPR2 Gα16-CHO EC$_{50}$ (% eff) |
|---|---|---|
| 10 | 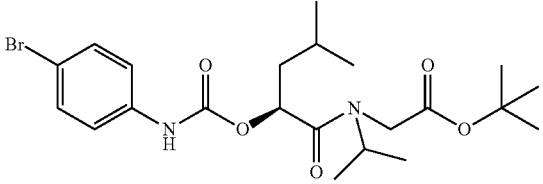 [SMILES: CC(C)C[C@H](OC(=O)Nc1ccc(Br)cc1)C(=O)N(CC(=O)OC(C)(C)C)C(C)C]<br>tert-Butyl {[(2S)-2-{[(4-Bromophenyl)carbamoyl]oxy}-4-methylpentanoyl](propan-2-yl)amino}acetate | 11 nM (1.03) |
| 11 | 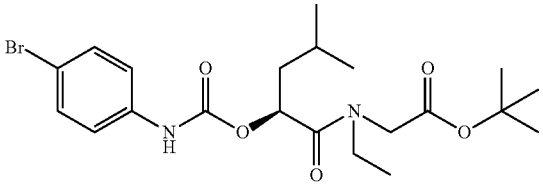 [SMILES: CCN(CC(=O)OC(C)(C)C)C(=O)[C@H](CC(C)C)OC(=O)Nc1ccc(Br)cc1]<br>tert-Butyl {[(2S)-2-{[(4-Bromophenyl)carbamoyl]oxy}-4-methylpentanoyl](ethyl)amino}acetate | 8.0 nM (0.97) |
| 12 | 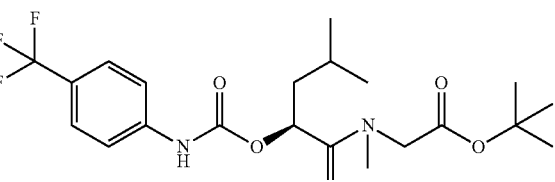<br>tert-Butyl {Methyl[(2S)-4-methyl-2-({[4-(trifluoromethyl)phenyl]carbamoyl}oxy)pentanoyl]amino}acetate | 24.8 nM (1.00) |
| 13 | 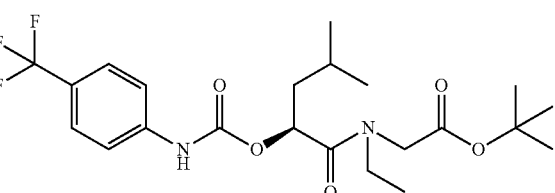<br>tert-Butyl {Ethyl[(2S)-4-methyl-2-({[4-(trifluoromethyl)phenyl]carbamoyl}oxy)pentanoyl]amino}acetate | 16.6 nM (0.99) |
| 14 | 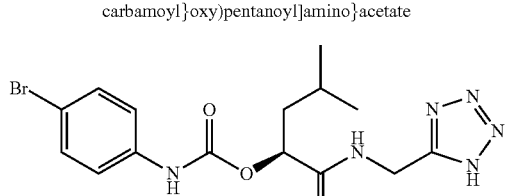<br>(2S)-4-Methyl-1-oxo-1-[(1H-tetrazol-5-ylmethyl)amino]pentan-2-yl (4-bromophenyl)carbamate | 1.3 nM (1.01) |
| 15 | 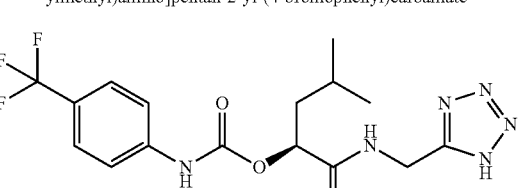<br>(2S)-4-methyl-1-oxo-1-[(1H-tetrazol-5-ylmethyl)amino]pentan-2-yl [4-(trifluoromethyl)phenyl]carbamate | 3.6 nM (0.96) |

TABLE 4-continued

| Compound No. | Structure/ IUPAC name | FPR2 Gα16-CHO EC$_{50}$ (% eff) |
| --- | --- | --- |
| 16 | (2S)-4-methyl-1-[methyl(1H-tetrazol-5-ylmethyl)amino]-1-oxopentan-2-yl (4-bromophenyl)carbamate | 0.81 nM (0.98) |
| 17 | (2S)-4-methyl-1-[methyl(1H-tetrazol-5-ylmethyl)amino]-1-oxopentan-2-yl [4-(trifluoromethyl)phenyl]carbamate | 2.4 nM (0.91) |
| 18 | 2-{[(2S)-4-Methyl-2-({[4-(trifluoromethyl)phenyl]carbamoyl}oxy)pentanoyl]amino}ethyl acetate | 195 nM (0.89) |
| 19 | {[(2S)-2-{[(4-Bromophenyl)carbamoyl]oxy}-4-methylpentanoyl]amino}acetic acid | 0.84 nM (1.01) |
| 20 | {[(2S)-4-Methyl-2-({[4-(trifluoromethyl)phenyl]carbamoyl}oxy)pentanoyl]amino}acetic acid | 3.9 nM (0.99) |
| 21 | {[(2S)-2-{[(4-Bromophenyl)carbamoyl]oxy}-4-methylpentanoyl](methyl)amino}acetic acid | 0.25 nM (1.06) |

TABLE 4-continued

| Compound No. | Structure/ IUPAC name | FPR2 Gα16-CHO EC$_{50}$ (% eff) |
|---|---|---|
| 22 | 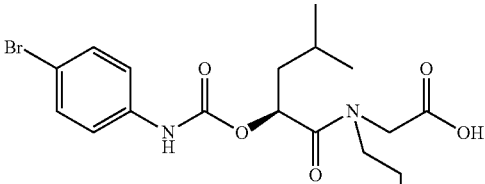 {[(2S)-2-{[(4-Bromophenyl)carbamoyl]oxy}-4-methylpentanoyl](propyl)amino}acetic acid | 0.44 nM (0.91) |
| 23 | 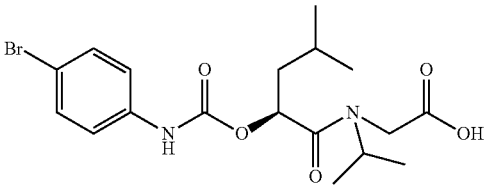 [SMILES: CC(C)C[C@H](OC(=O)Nc1ccc(Br)cc1)C(=O)N(CC(=O)O)C(C)C] {[(2S)-2-{[(4-Bromophenyl)carbamoyl]oxy}-4-methylpentanoyl](propan-2-yl)amino}acetic acid | 0.32 nM (1.05) |
| 24 | 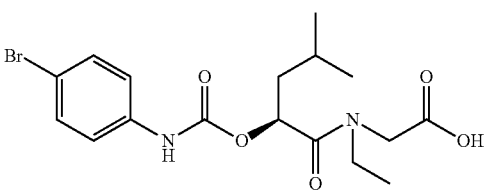 [SMILES: CCN(CC(=O)O)C(=O)[C@H](CC(C)C)OC(=O)Nc1ccc(Br)cc1] {[(2S)-2-{[(4-Bromophenyl)carbamoyl]oxy}-4-methylpentanoyl](ethyl)amino}acetic acid | 0.24 nM (0.95) |
| 25 | 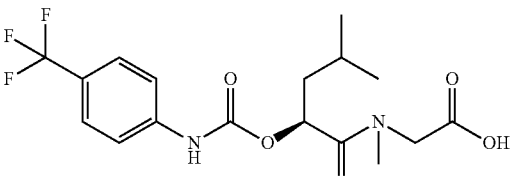 {Methyl[(2S)-4-methyl-2-({[4-(trifluoromethyl)phenyl]carbamoyl}oxy)pentanoyl]amino}acetic acid | 0.94 nM (0.97) |
| 26 | 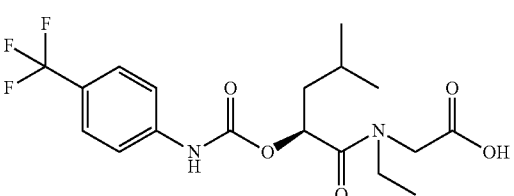 {Ethyl[(2S)-4-methyl-2-({[4-(trifluoromethyl)phenyl]carbamoyl}oxy)pentanoyl]amino}acetic acid | 0.29 nM (0.98) |
| 27 | 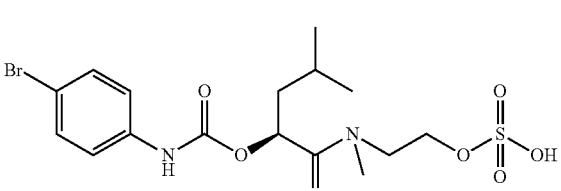 (2S)-4-Methyl-1-{methyl[2-(sulfooxy)ethyl]amino}-1-oxopentan-2-yl (4-bromophenyl)carbamate | 8.7 nM (0.99) |

TABLE 4-continued

| Compound No. | Structure/ IUPAC name | FPR2 Gα16-CHO EC$_{50}$ (% eff) |
|---|---|---|
| 28 | 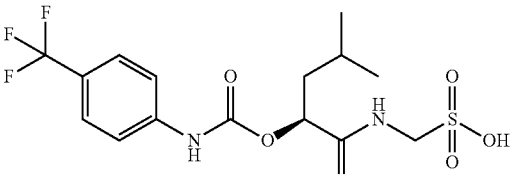<br>({(2S)-4-methyl-2-[({[4-(trifluoromethyl)phenyl]amino}carbonyl)oxy]pentanoyl}amino)methanesulfonic acid | 4.3 nM (0.85) |
| 29 | 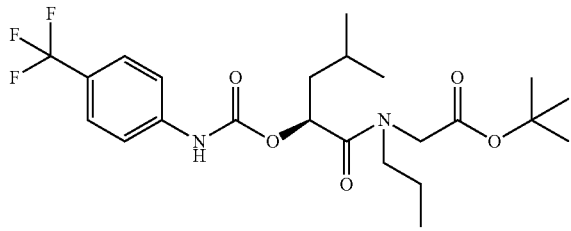 [SMILES: CCCN(CC(=O)OC(C)(C)C)C(=O)[C@H](CC(C)C)OC(=O)Nc1ccc(C(F)(F)F)cc1]<br>tert-Butyl [{(2S)-4-methyl-2-[({[4-(trifluoromethyl)phenyl]amino}carbonyl)oxy]pentanoyl}(propyl)amino]acetate | 11.4 nM (1.01) |
| 30 | 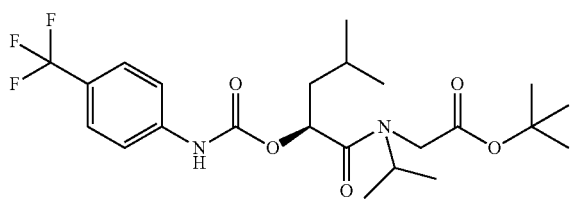 [SMILES: CC(C)C[C@H](OC(=O)Nc1ccc(C(F)(F)F)cc1)C(=O)N(CC(=O)OC(C)(C)C)C(C)C]<br>tert-Butyl (isopropyl{(2S)-4-methyl-2-[({[4-(trifluoromethyl)phenyl]amino}carbonyl)oxy]pentanoyl}amino)acetate | 301 nM (0.76) |
| 31 | 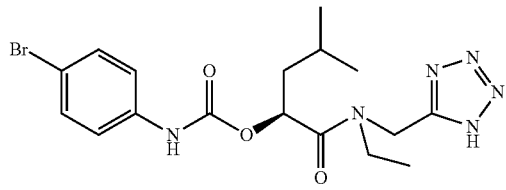 [SMILES: CCN(Cc1nnn[nH]1)C(=O)[C@H](CC(C)C)OC(=O)Nc1ccc(Br)cc1]<br>(1S)-1-{[ethyl(1H-tetrazol-5-ylmethyl)amino]carbonyl}-3-methylbutyl (4-bromophenyl)carbamate | 0.30 nM (0.95) |
| 32 | 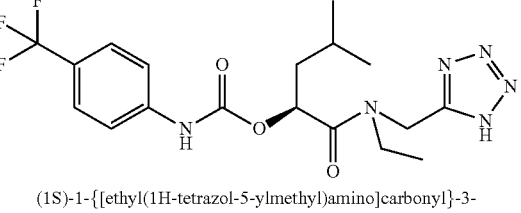<br>(1S)-1-{[ethyl(1H-tetrazol-5-ylmethyl)amino]carbonyl}-3-methylbutyl [4-(trifluoromethyl)phenyl]carbamate | 0.66 nM (1.00) |

TABLE 4-continued

| Compound No. | Structure/ IUPAC name | FPR2 Gα16-CHO EC$_{50}$ (% eff) |
| --- | --- | --- |
| 33 | (1S)-1-[({2-[(tert-butoxycarbonyl)amino]ethyl}amino)carbonyl]-3-methylbutyl (4-bromophenyl)carbamate | 397 nM (1.03) |
| 34 | tert-Butyl {[(2S)-2-({[(4-bromophenyl)amino]carbonyl}oxy)-3-phenylpropanoyl]amino}acetate | 106 nM (1.03) |
| 35 | (1S)-1-benzyl-2-oxo-2-[(1H-tetrazol-5-ylmethyl)amino]ethyl (4-bromophenyl)carbamate | 0.83 nM (1.03) |
| 36 | tert-Butyl {[(2S)-2-({[(4-bromophenyl)amino]carbonyl}oxy)-3-phenylpropanoyl](methyl)amino}acetate | 11.7 nM (1.05) |
| 37 | [{(2S)-4-methyl-2-[({[4-(trifluoromethyl)phenyl]amino}carbonyl)oxy]pentanoyl}(propyl)amino]acetic acid | 1.2 nM (1.02) |

TABLE 4-continued

| Compound No. | Structure/IUPAC name | FPR2 Gα16-CHO EC$_{50}$ (% eff) |
|---|---|---|
| 38 | 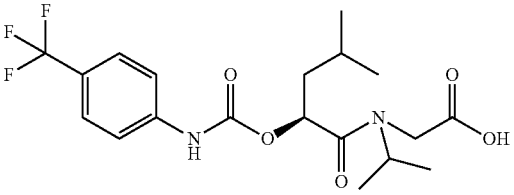 [SMILES: CC(C)C[C@H](OC(=O)Nc1ccc(C(F)(F)F)cc1)C(=O)N(CC(=O)O)C(C)C]<br>(Isopropyl{(2S)-4-methyl-2-[({[4-(trifluoromethyl)phenyl]amino}carbonyl)oxy]pentanoyl}amino)acetic acid | 0.66 nM (1.07) |
| 39 | 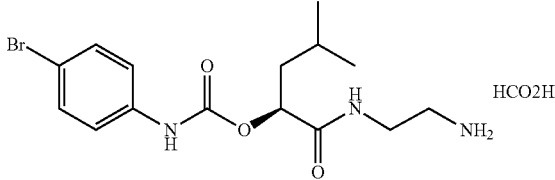 [SMILES: CC(C)C[C@H](OC(=O)Nc1ccc(Br)cc1)C(=O)NCCN ; "HCO2H"]<br>(1S)-1-{[(2-aminoethyl)amino]carbonyl}-3-methylbutyl (4-bromophenyl)carbamate | 78 nM (0.89) |
| 40 | 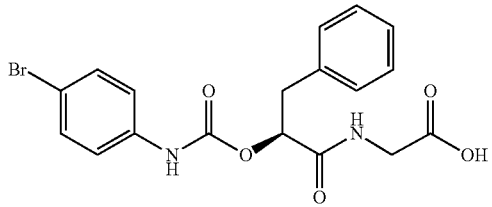<br>{[(2S)-2-({[(4-bromophenyl)amino]carbonyl}oxy)-3-phenylpropanoyl]amino}acetic acid | 1.3 nM (0.95) |
| 41 | 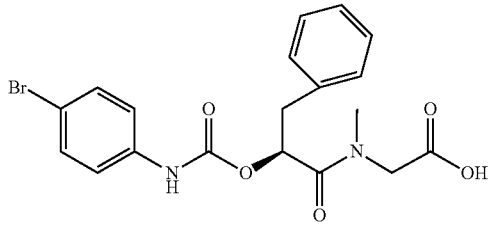<br>{[(2S)-2-({[(4-Bromophenyl)amino]carbonyl}oxy)-3-phenylpropanoyl](methyl)amino}acetic acid | 0.41 nM (0.98) |
| 42 | 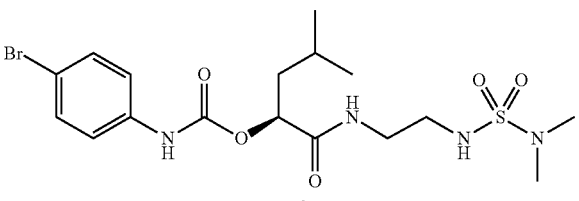 [SMILES: CC(C)C[C@H](OC(=O)Nc1ccc(Br)cc1)C(=O)NCCNS(=O)(=O)N(C)C]<br>(1S)-1-{[(2-{[(Dimethylamino)sulfonyl]amino}ethyl)amino]carbonyl}-3-methylbutyl (4-bromophenyl)carbamate | 125 nM (0.99) |

TABLE 4-continued

| Compound No. | Structure/ IUPAC name | FPR2 Gα16-CHO EC$_{50}$ (% eff) |
|---|---|---|
| Intermediate 1 | (S)-tert-Butyl 2-(((4-Bromophenyl)carbamoyl)oxy)-4-methyl pentanoate | Not Determined |
| Intermediate 2 | tert-Butyl (2S)-4-Methyl-2-[({[4-(trifluoromethyl)phenyl]carbamoyl}oxy]pentanoate | 10000 nM (0.56) |
| Intermediate 3 | (2S)-2-{[(4-Bromophenyl)carbamoyl]oxy}-4-methylpentanoic acid | 8.6 nM (0.85) |
| Intermediate 4 | (2S)-4-Methyl-2-[({[4-(trifluoromethyl)phenyl]carbamoyl}oxy]pentanoic acid | 24.7 nM (0.88) |
| Intermediate 2a | tert-Butyl (2S)-2-({[(4-bromophenyl)amino]carbonyl}oxy)-3-phenyl propanoate | 2195 nM (0.55) |
| Intermediate 4a | (2S)-2-({[(4-bromophenyl)amino]carbonyl}oxy)-3-phenylpropanoic acid | 1.43 nM (1.03) |

What is claimed is:
1. A compound of Formula I:

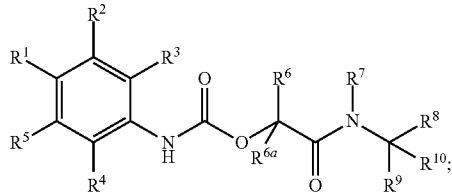

Formula I wherein:
- $R^1$ is optionally substituted $C_{1-8}$ alkyl, optionally substituted $C_{3-8}$ cycloalkyl, optionally substituted heterocycle, optionally substituted $C_{6-10}$ aryl, optionally substituted $C_{3-8}$ cycloalkenyl, halogen, $NR^{11}R^{12}$, fluorinated $C_{1-8}$ alkyl, perfluorinated $C_{1-8}$ alkyl, —S(O)$_m$R$^{13}$, —C(O)R$^{14}$ or —OR$^{15}$;
- $R^2$ is H, optionally substituted $C_{1-8}$ alkyl, optionally substituted $C_{3-8}$ cycloalkyl, optionally substituted heterocycle, optionally substituted $C_{6-10}$ aryl, optionally substituted $C_{3-8}$ cycloalkenyl, halogen, $NR^{11}R^{12}$, fluorinated $C_{1-8}$ alkyl, perfluorinated $C_{1-8}$ alkyl, —S(O)$_m$R$^{13}$, —C(O)R$^{14}$ or —OR$^{15}$;
- $R^3$ is H, optionally substituted $C_{1-8}$ alkyl, optionally substituted $C_{3-8}$ cycloalkyl, optionally substituted heterocycle, optionally substituted $C_{6-10}$ aryl, optionally substituted $C_{3-8}$ cycloalkenyl, halogen, $NR^{11}R^{12}$, fluorinated $C_{1-8}$ alkyl, perfluorinated $C_{1-8}$ alkyl, —S(O)$_m$R$^{13}$, —C(O)R$^{14}$ or —OR$^{15}$;
- $R^4$ is H, optionally substituted $C_{1-8}$ alkyl, optionally substituted $C_{3-8}$ cycloalkyl, optionally substituted heterocycle, optionally substituted $C_{6-10}$ aryl, optionally substituted $C_{3-8}$ cycloalkenyl, halogen, $NR^{11}R^{12}$, fluorinated $C_{1-8}$ alkyl, perfluorinated $C_{1-8}$ alkyl, —S(O)$_m$R$^{13}$—C(O)R$^{14}$ or —OR$^{15}$;
- $R^5$ is H, optionally substituted $C_{1-8}$ alkyl, optionally substituted $C_{3-8}$ cycloalkyl, optionally substituted heterocycle, optionally substituted $C_{6-10}$ aryl, optionally substituted $C_{3-8}$ cycloalkenyl, halogen, $NR^{11}R^{12}$, fluorinated $C_{1-8}$ alkyl, perfluorinated $C_{1-8}$ alkyl, —S(O)$_m$R$^{13}$, —C(O)R$^{14}$ or —OR$^{15}$;
- $R^6$ is H, optionally substituted $C_{1-8}$ alkyl, optionally substituted heterocycle, —(CH$_2$)$_p$COOH, —(CH$_2$)$_p$—NH$_2$, —(CH$_2$)$_p$—OH, —(CH$_2$)$_p$—SH, —(CH$_2$)$_p$—CONH$_2$, —(CH$_2$)$_p$—CONH$_2$, —CH(OH)CH$_3$, —(CH$_2$)$_p$SCH$_3$, —(CH$_2$)$_p$NH—C(=NH)(NH$_2$) or —CH$_2$C$_{6-10}$aryl, wherein said —C$_{6-10}$aryl is optionally substituted;
- $R^{6a}$ is H or optionally substituted $C_{1-8}$ alkyl;
- $R^7$ is H or optionally substituted $C_{1-8}$ alkyl;
- $R^8$ is H;
- $R^9$ is H, optionally substituted $C_{1-8}$ alkyl, optionally substituted $C_{3-8}$ cycloalkyl, optionally substituted heterocycle, optionally substituted $C_{6-10}$ aryl or optionally substituted $C_{3-8}$ cycloalkenyl;
- $R^{10}$ is —(CH$_2$)$_n$OR$^{16}$, —(CH$_2$)—S(O)$_2$OH, —(CH$_2$)$_n$C(O)R$^{17}$, —(CH$_2$)$_n$OS(O)$_2$OH, (CH$_2$)$_n$NR$^{18}$R$^{19}$, —(CH$_2$)—P(O)(OC$_{1-6}$ alkyl)$_2$, —(CH$_2$)$_n$P(O)(OC$_{1-6}$ alkyl)OH, —(CH$_2$)$_n$—P(O)(OH)$_2$ or optionally substituted heterocycle;
- $R^{11}$ is optionally substituted $C_{1-8}$ alkyl, optionally substituted $C_{3-8}$ cycloalkyl, optionally substituted heterocycle, optionally substituted $C_{6-10}$ aryl or optionally substituted $C_{3-8}$ cycloalkenyl;
- $R^{12}$ is H, optionally substituted $C_{1-8}$ alkyl, optionally substituted $C_{3-8}$ cycloalkyl, optionally substituted heterocycle, optionally substituted $C_{6-10}$ aryl or optionally substituted $C_{3-8}$ cycloalkenyl;
- $R^{13}$ is H, optionally substituted $C_{1-8}$ alkyl, optionally substituted $C_{3-8}$ cycloalkyl, optionally substituted heterocycle, optionally substituted $C_{6-10}$ aryl, OH or optionally substituted $C_{3-8}$ cycloalkenyl;
- $R^{14}$ is optionally substituted $C_{1-8}$ alkyl, optionally substituted $C_{3-8}$ cycloalkyl, optionally substituted heterocycle, optionally substituted $C_{6-10}$ aryl, optionally substituted $C_{3-8}$ cycloalkenyl or —OR$^{15}$;
- $R^{15}$ is H or optionally substituted $C_{1-8}$ alkyl;
- $R^{16}$ is H, —C(O)(C$_{1-8}$ alkyl) or optionally substituted $C_{1-8}$ alkyl;
- $R^{17}$ is OH, —OC$_{1-8}$ alkyl or C$_{1-8}$ alkyl;
- $R^{18}$ is selected from the group consisting of H, optionally substituted $C_{1-8}$ alkyl, optionally substituted $C_{3-8}$ cycloalkyl, optionally substituted heterocycle, optionally substituted $C_{6-10}$ aryl, optionally substituted $C_{3-8}$ cycloalkenyl, —C(O)R$^{17}$ and —S(O)$_2$N(C$_{1-8}$ alkyl)$_2$;
- $R^{19}$ is selected from the group consisting of H, optionally substituted $C_{1-8}$ alkyl, optionally substituted $C_{3-8}$ cycloalkyl, optionally substituted heterocycle, optionally substituted $C_{6-10}$ aryl, or optionally substituted $C_{3-8}$ cycloalkenyl, —C(O)R$^{17}$ and —S(O)$_2$N(C$_{1-8}$ alkyl)$_2$; with a proviso when $R^{10}$ is —(CH)$_n$C(O)R$^{17}$ and $R^{17}$ is $C_{1-8}$ alkyl, then $R^9$ is H;
- p is 1, 2 or 3;
- n is 0, 1, 2, 3, 4, 5, 6, 7 or 8; and
- m is 0, 1 or 2;

wherein
- each $C_{1-8}$ alkyl substituent is independently selected from the group consisting of halogen, hydroxyl, —OC$_{1-8}$alkyl, $C_{3-8}$cycloalkyl, amino, heterocycle, $C_{6-10}$aryl, carboxylic acid, phosphonic acid, sulphonic acid, phosphoric acid, nitro, amide, sulfonamide, sulfonamide and carboxylate ester;
- each $C_{3-8}$ cycloalkyl substituent is independently selected from the group consisting of halogen, hydroxyl, sulfonyl $C_{1-8}$ alkyl, sulfoxide $C_{1-8}$ alkyl, sulfonamide, nitro, —OC$_{1-8}$ alkyl, —SC$_{1-8}$ alkyl groups, —C$_{1-8}$ alkyl, ketone, alkylamino, amino, $C_{6-10}$ aryl and $C_{3-8}$ cycloalkyl;
- each heterocycle substituent is independently selected from the group consisting of halogen, hydroxyl, —OC$_{1-8}$ alkyl, sulfonyl $C_{1-8}$ alkyl, sulfoxide $C_{1-8}$ alkyl, nitro, —SC$_{1-8}$ alkyl, —C$_{1-8}$ alkyl, ketone, alkylamino, amino, $C_{6-10}$ aryl and $C_{3-8}$ cycloalkyl;
- each $C_{6-10}$ aryl substituent is independently selected from the group consisting of halogen, hydroxyl, sulfonyl $C_{1-8}$ alkyl, sulfoxide $C_{1-8}$ alkyl, sulfonamide, carboxylic acid, $C_{1-8}$ alkyl carboxylate (ester), amide, nitro, —OC$_{1-6}$ alkyl, —SC$_{1-8}$ alkyl, —C$_{1-8}$ alkyl, ketone, alkylamino, amino and $C_{3-8}$ cycloalkyl; and
- each $C_{3-8}$ cycloalkenyl substituent is independently selected from the group consisting of halogen, hydroxyl, sulfonyl $C_{1-8}$ alkyl, sulfoxide $C_{1-8}$ alkyl, nitro, —OC$_{1-6}$ alkyl, —SC$_{1-6}$ alkyl, —C$_{1-6}$ alkyl, ketone, alkylamino, amino, $C_{6-10}$ aryl and $C_{3-8}$ cycloalkyl;

or an enantiomer, diastereomer or tautomer thereof;
or a pharmaceutically acceptable salt of any of the foregoing.

2. The compound of claim 1, wherein:
R$^1$ is selected from the group consisting of halogen, fluorinated C$_{1-8}$ alkyl and perfluorinated C$_{1-8}$ alkyl.
3. The compound of claim 1, wherein:
each of R$^2$, R$^3$, R$^4$ and R$^5$ is H.
4. The compound of claim 1, wherein:
R$^6$ is H, optionally substituted C$_{1-8}$ alkyl or —CH$_2$C$_{6-10}$aryl, wherein said C$_{1-6}$ aryl is optionally substituted;
R$^{6a}$ is H; and
R$^7$ is H, methyl, ethyl, n-propyl, isopropyl, n-butyl, sec-butyl, isobutyl or t-butyl.
5. The compound of claim 1, wherein:
n is 0 or 1;
R$^9$ is H;
R$^{10}$ is —(CH$_2$)$_n$OR$^{16}$, —(CH$_2$)—C(O)R$^{17}$, —(CH$_2$)$_n$S(O)$_2$OH, —(CH$_2$)—NR$^{18}$R$^{19}$, —(CH$_2$)$_n$—P(O)(OC$_{1-6}$alkyl)$_2$, —(CH$_2$)$_n$—P(O)(OC$_{1-6}$alkyl)OH, —(CH$_2$)$_n$—P(O)(OH)$_2$ or optionally substituted heterocycle;
R$^{16}$ is H or —C(O)(C$_{1-8}$ alkyl);
R$^{17}$ is OH or —OC$_{1-8}$ alkyl;
R$^{18}$ H; and
R$^{19}$ is selected from the group consisting of H, —C(O)R$^{17}$ and —S(O)$_2$N(C$_{1-8}$ alkyl)$_2$.
6. The compound of claim 1, wherein:
R$^1$ is selected from the group consisting of halogen, fluorinated C$_{1-8}$ alkyl and perfluorinated C$_{1-8}$ alkyl;
each of R$^2$, R$^3$, R$^4$ and R$^5$ is H;
R$^6$ is H, optionally substituted C$_{1-8}$ alkyl or —CH$_2$C$_{6-10}$aryl, wherein said C$_{6-10}$aryl is optionally substituted;
R$^{6a}$ is H;
R$^9$ is H;
R$^{10}$ is —(CH$_2$)$_n$OR$^{16}$, —(CH$_2$)—C(O)R$^{17}$, —(CH$_2$)$_n$—S(O)$_2$OH, —(CH$_2$)$_n$NR$^{18}$R$^{19}$, —(CH$_2$)$_n$—P(O)(OC$_{1-6}$alkyl)$_2$, —(CH$_2$)$_n$—P(O)(OC$_{1-6}$alkyl)OH, —(CH$_2$)$_n$—P(O)(OH)$_2$ or optionally substituted heterocycle;
R$^{16}$ is H or —C(O)(C$_{1-8}$ alkyl);
R$^{17}$ is OH or —OC$_{1-8}$ alkyl;
R$^{18}$ H; and
R$^{19}$ is selected from the group consisting of H, —C(O)R$^{17}$ and —S(O)$_2$N(C$_{1-8}$ alkyl)$_2$.
7. The compound of claim 6, wherein:
each C$_{1-8}$ alkyl is independently selected from the group consisting of methyl, ethyl, n-propyl, isopropyl, n-butyl, sec-butyl, isobutyl and t-butyl; and
R$^7$ is H, methyl, ethyl, n-propyl, isopropyl, n-butyl, sec-butyl, isobutyl or t-butyl.
8. The compound of claim 1, selected from the group consisting of:

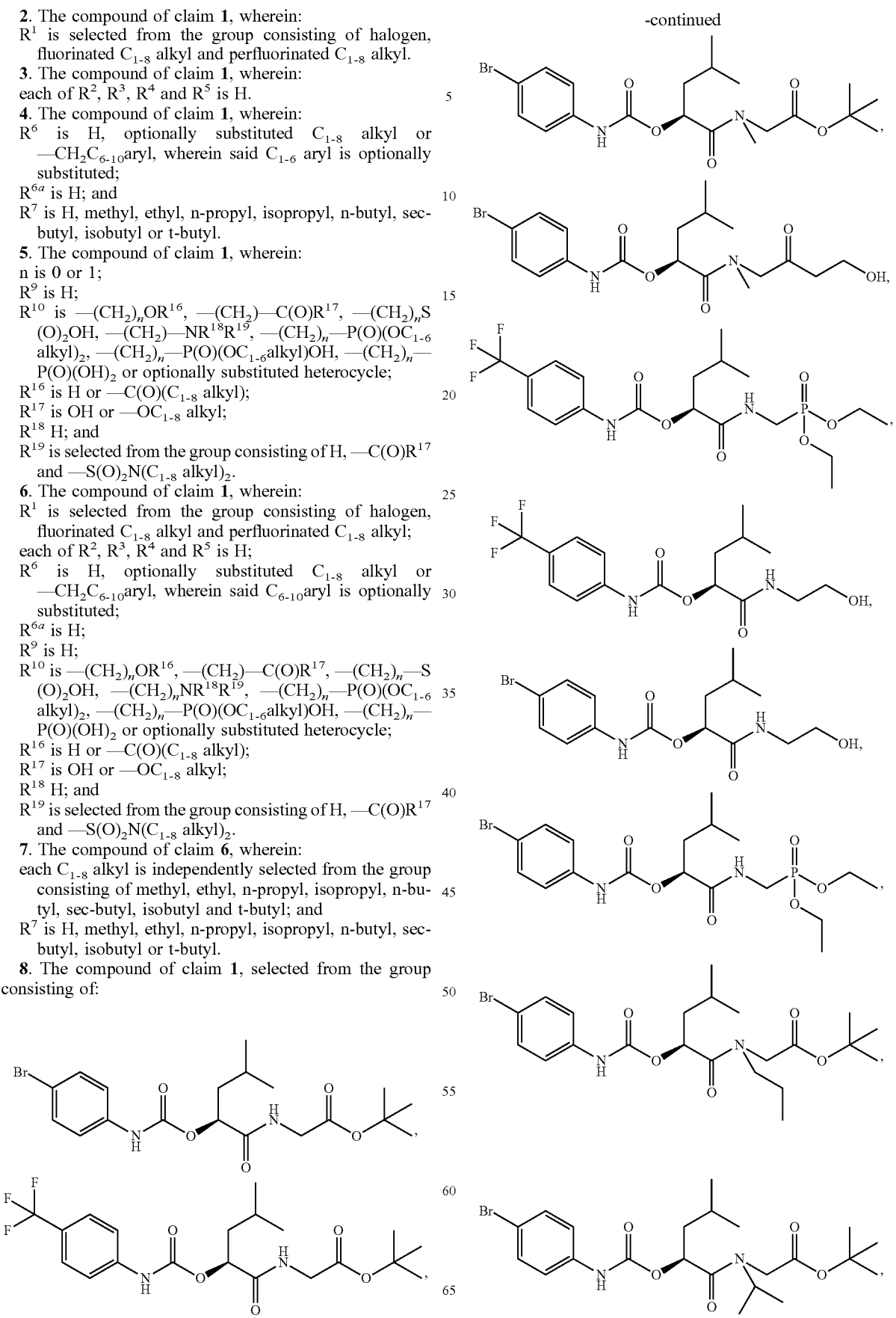

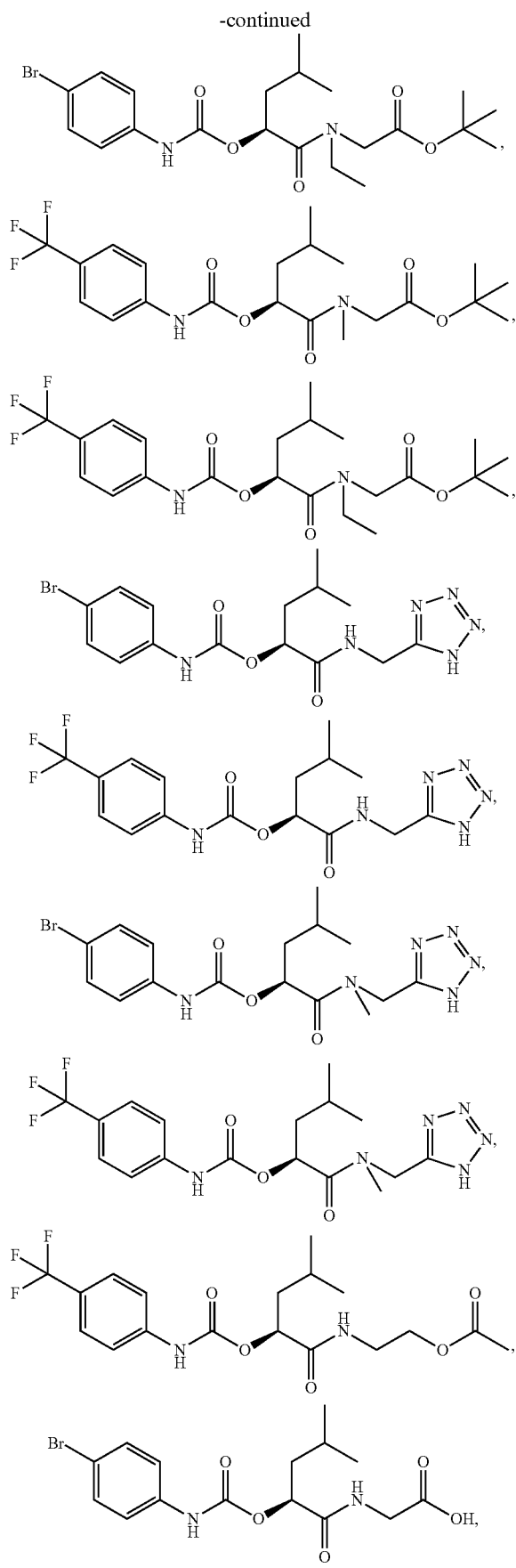
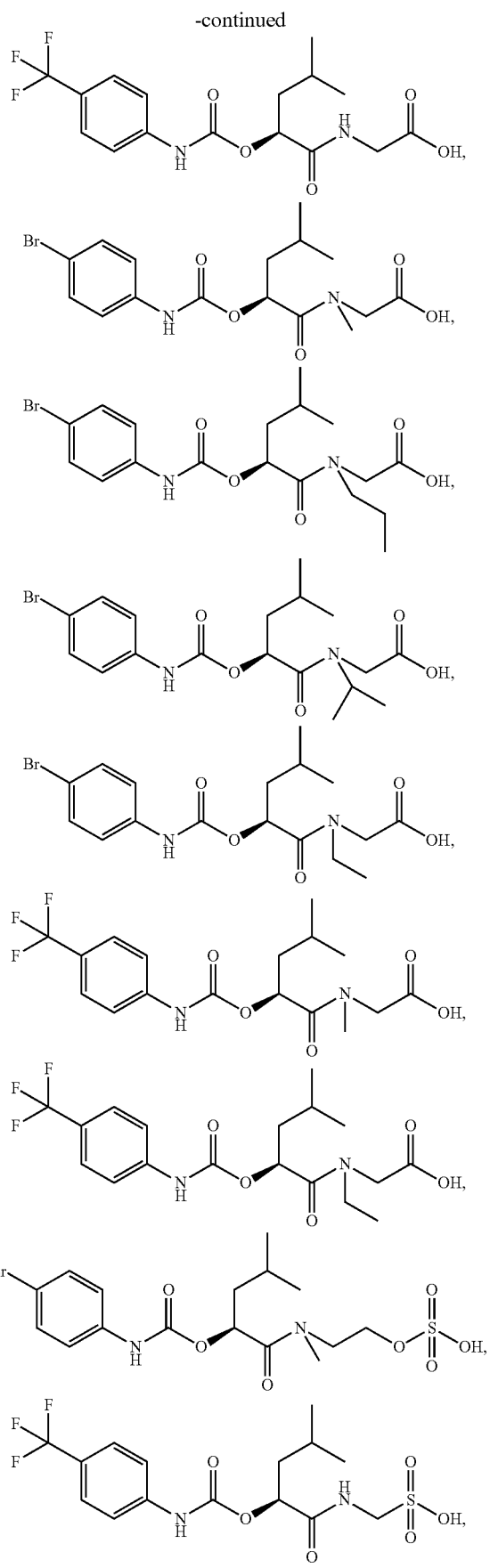

-continued

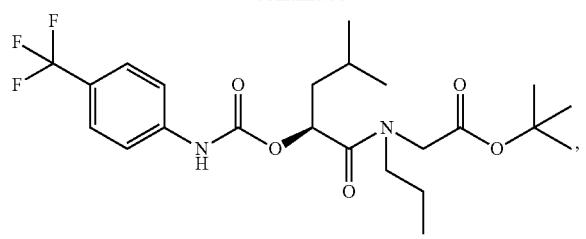

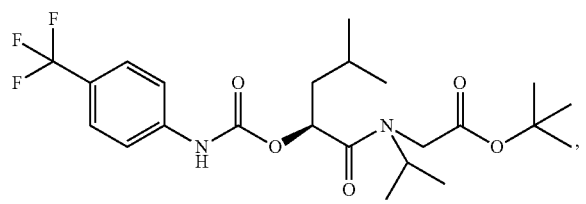

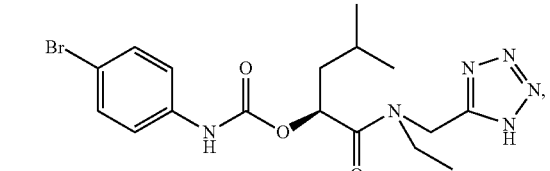

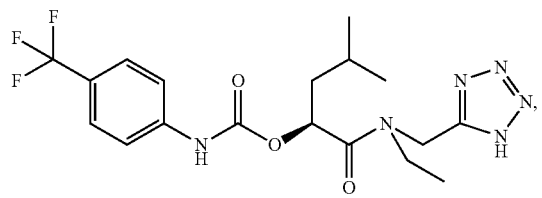

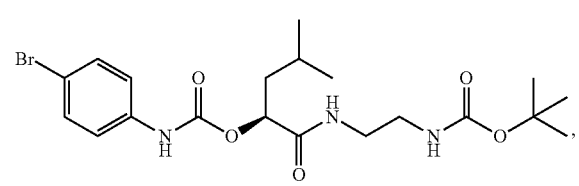

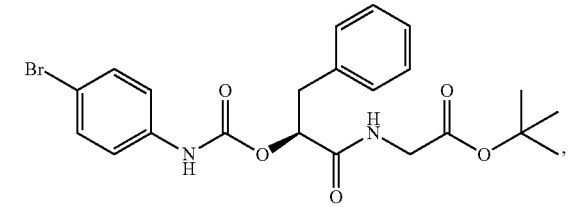

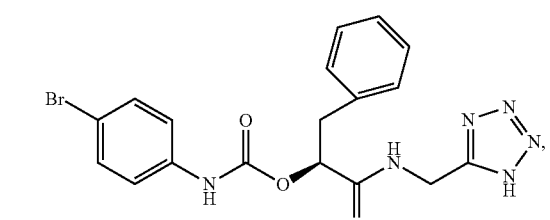

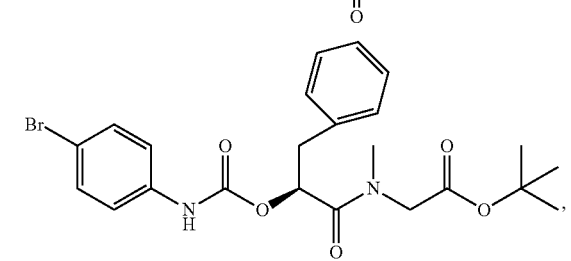

-continued

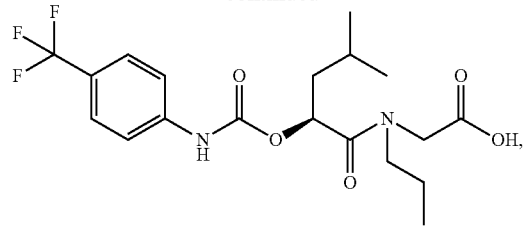

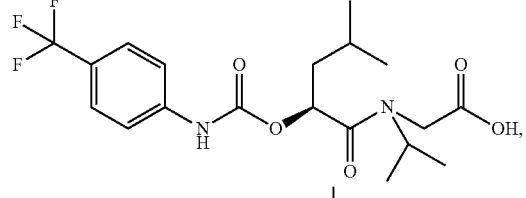

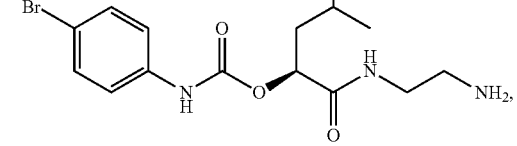

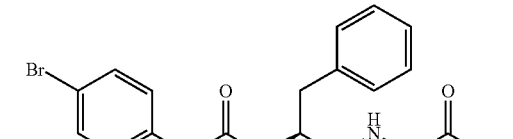

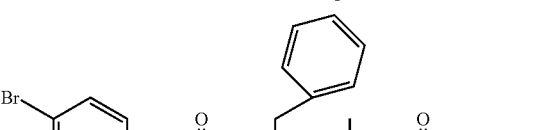

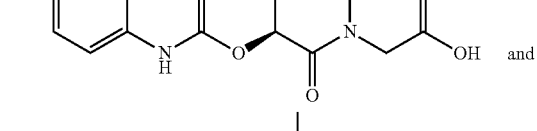

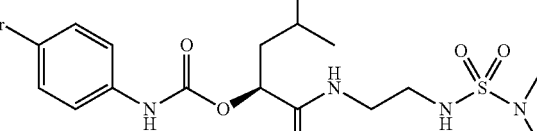

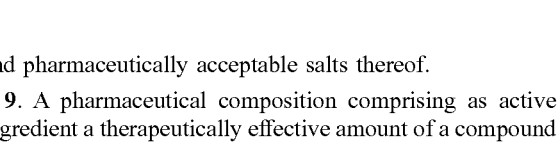 and

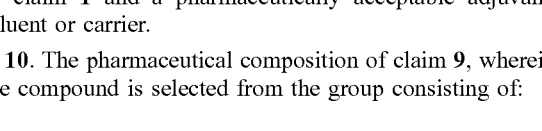

and pharmaceutically acceptable salts thereof.

9. A pharmaceutical composition comprising as active ingredient a therapeutically effective amount of a compound of claim 1 and a pharmaceutically acceptable adjuvant, diluent or carrier.

10. The pharmaceutical composition of claim 9, wherein the compound is selected from the group consisting of:

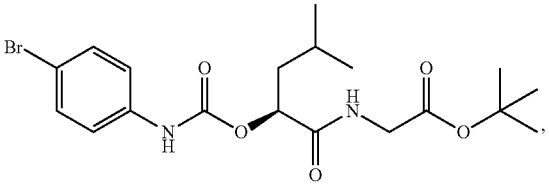

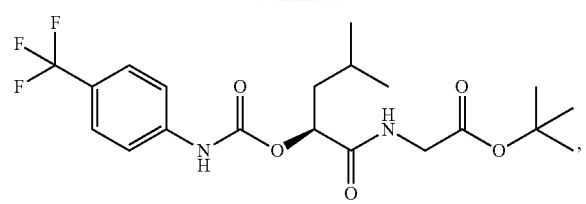
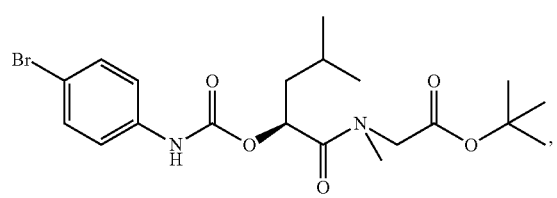
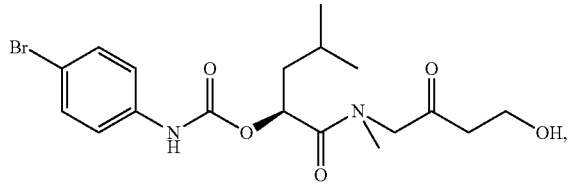
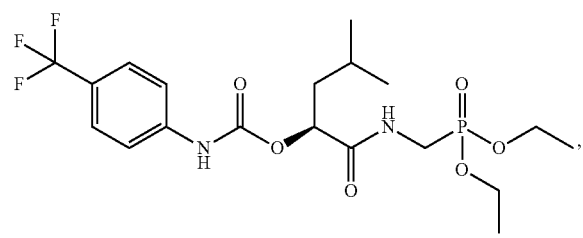
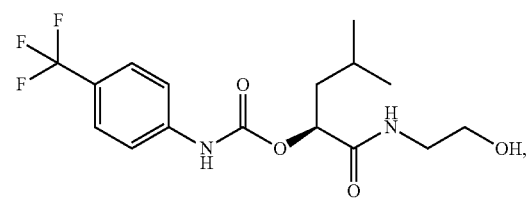
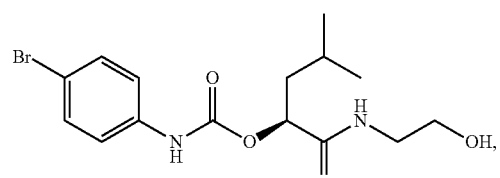
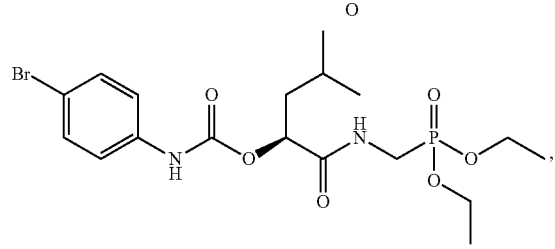
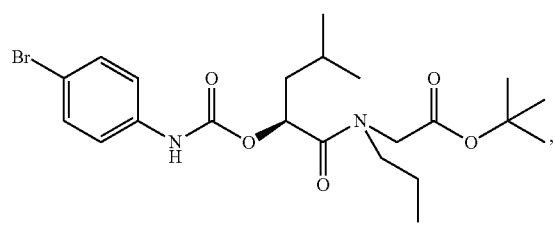
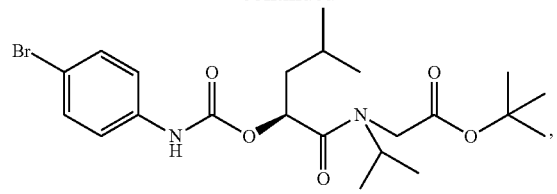
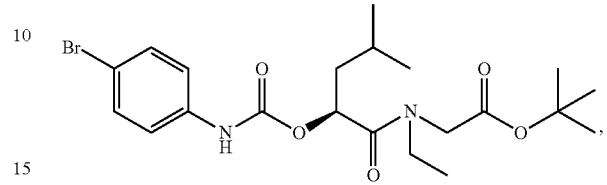
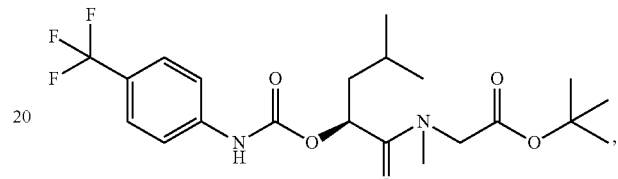
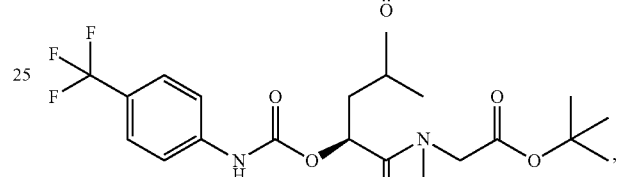
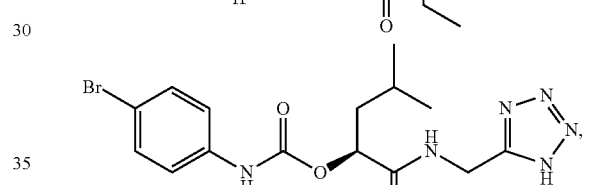
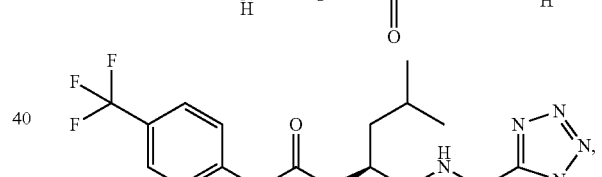
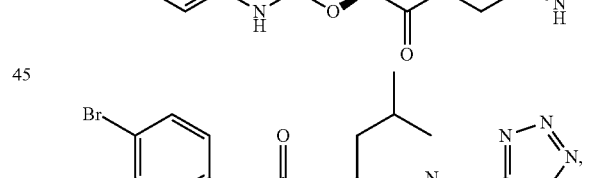
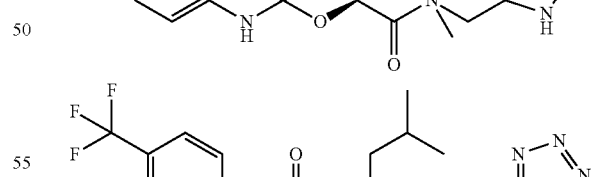
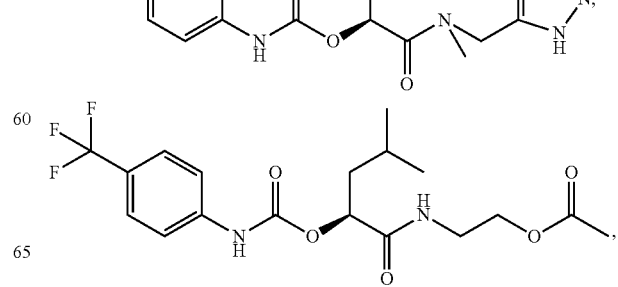

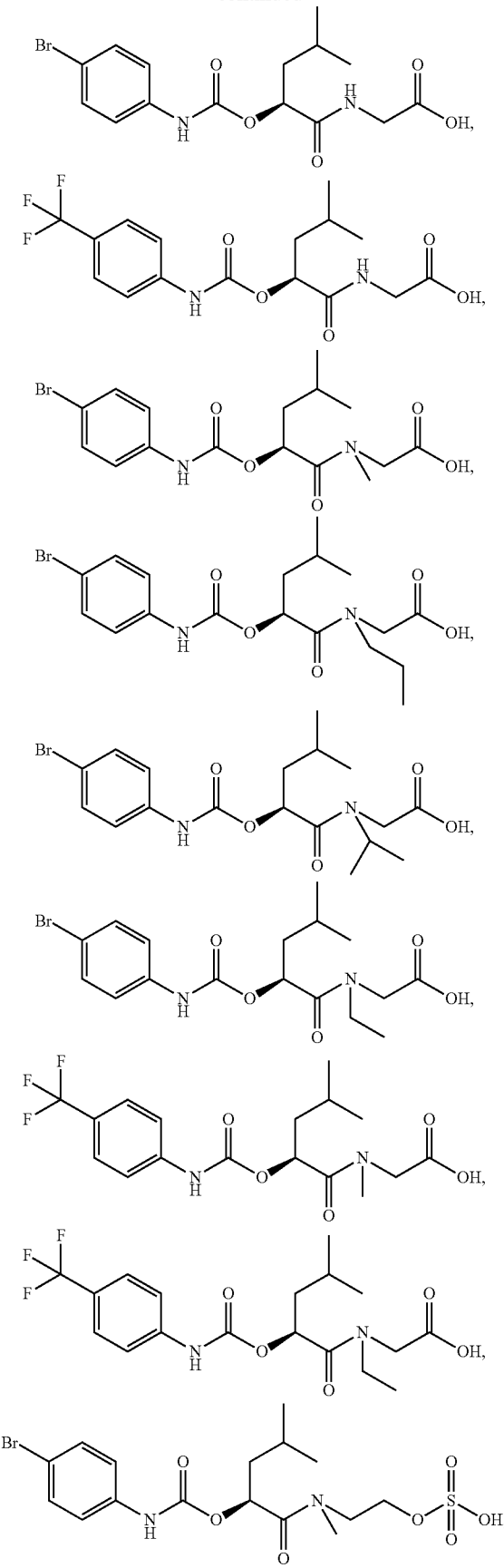
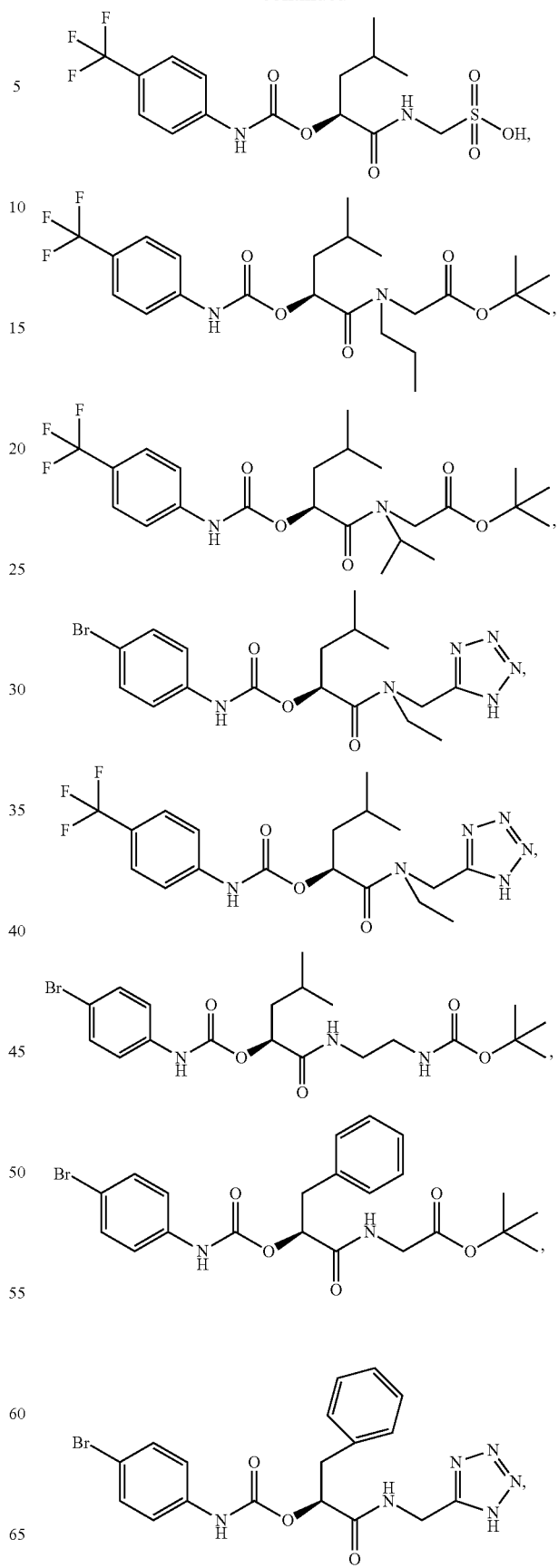

75
-continued
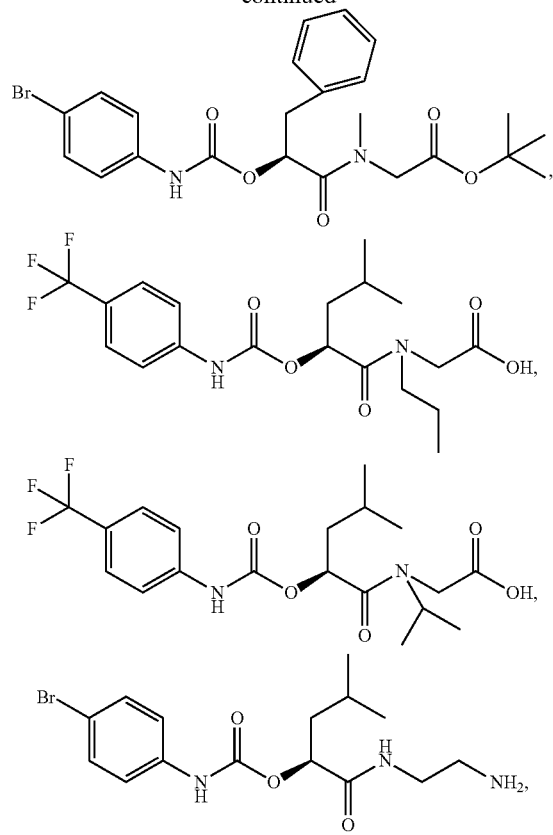
76
-continued
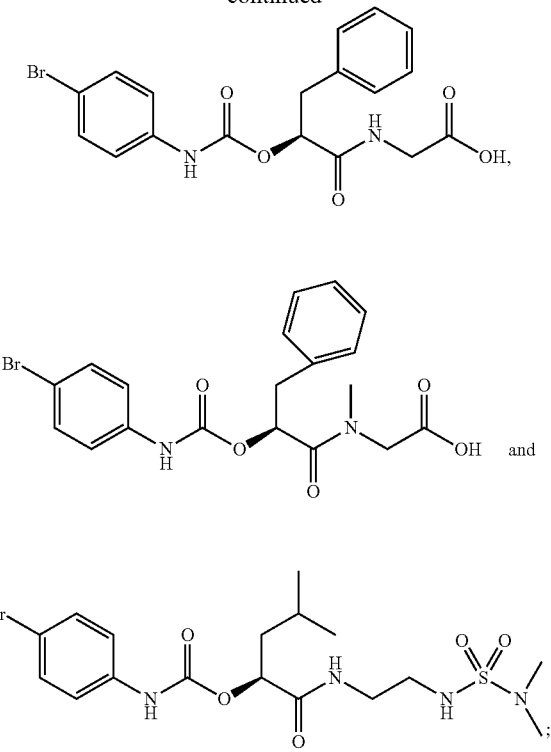
and pharmaceutically acceptable salts thereof.
* * * * *

UNITED STATES PATENT AND TRADEMARK OFFICE
CERTIFICATE OF CORRECTION

PATENT NO. : 9,926,264 B2
APPLICATION NO. : 15/034793
DATED : March 27, 2018
INVENTOR(S) : Richard L. Beard et al.

Page 1 of 5

It is certified that error appears in the above-identified patent and that said Letters Patent is hereby corrected as shown below:

On the page 2, in Column 1, under "Other Publications", Line 3, delete "U52014" and insert -- US2014 --, therefor.

In Column 2, Line 12, delete "Madema" and insert -- Maderna --, therefor.

In Column 3, Line 57, delete "$C_{1-8}$alkyl," and insert -- $C_{1-8}$ alkyl, --, therefor.

In Column 3, Line 66, delete "—$S(O)_mR^{13}$—$C(O)R^{14}$" and insert -- —$S(O)_mR^{13}$, —$C(O)R^{14}$ --, therefor.

In Column 4, Line 5, delete "—$S(O)_mR^{13}$—$C(O)R^{14}$" and insert -- —$S(O)_mR^{13}$, —$C(O)R^{14}$ --, therefor.

In Column 4, Line 10, delete "—$S(O)_mR^{13}$—$C(O)R^{14}$" and insert -- —$S(O)_mR^{13}$, —$C(O)R^{14}$ --, therefor.

In Column 4, Line 16, delete "—$S(O)_mR^{13}$—$C(O)R^{14}$" and insert -- —$S(O)_mR^{13}$, —$C(O)R^{14}$ --, therefor.

In Column 4, Line 22, delete "—$CH_2C_{6-10}$ aryl," and insert -- —$CH_2C_{6-10}$aryl, --, therefor.

In Column 4, Line 23, delete "—$C_{6-10}$ aryl" and insert -- —$C_{6-10}$aryl --, therefor.

In Column 5, Line 16, delete "—$C_{1-6}$ alkyl," and insert -- —$C_{1-8}$ alkyl, --, therefor.

In Column 5, Line 29, delete "—$C_{1-8}$ alkyl," and insert -- —$C_{1-6}$ alkyl, --, therefor.

In Column 6, Line 53, delete "—$SC_{1-8}$ alkyl" and insert -- —$SC_{1-6}$ alkyl --, therefor.

In Column 6, Line 63, delete "carbocylic" and insert -- carbocyclic --, therefor.
In Column 6, Line 64, delete "heterocylic" and insert -- heterocyclic --, therefor.

Signed and Sealed this
Fifteenth Day of May, 2018

Andrei Iancu
*Director of the United States Patent and Trademark Office*

CERTIFICATE OF CORRECTION (continued)
U.S. Pat. No. 9,926,264 B2

In Column 7, Line 46, delete ""—C(O)NR$^x$R$^y$"" and insert -- "—C(O)NR$^x$R$^y$," --, therefor.

In Column 8, Lines 45-47, delete "{[(2S)-2-{[(4-Bromophenyl)carbamoyl]oxy}-4-methylpentanoyl](propan-2-yl)amino}acetic acid;" and insert the same in Column 8, Line 46, as a new paragraph.

In Column 9, Lines 32-34, delete "tert-Butyl (2S)-2-({[(4-bromophenyl)amino]carbonyl}oxy)-3-phenyl propanoate; and" and insert the same in Column 9, Line 33, as a new paragraph.

In Column 12, Line 31, delete "vasuclar" and insert -- vascular --, therefor.

In Column 15, Line 12, after "convenient" insert -- . --.

In Column 18, Line 64, delete "—S(O)$_m$R$^{13}$—C(O)R$^{14}$" and insert -- —S(O)$_m$R$^{13}$, —C(O)R$^{14}$ --, therefor.

In Column 19, Line 3, delete "—S(O)$_m$R$^{13}$—C(O)R$^{14}$" and insert -- —S(O)$_m$R$^{13}$, —C(O)R$^{14}$ --, therefor.

In Column 19, Line 9, delete "—S(O)$_m$R$^{13}$—C(O)R$^{14}$" and insert -- —S(O)$_m$R$^{13}$, —C(O)R$^{14}$ --, therefor.

In Column 19, Line 15, delete "—S(O)$_m$R$^{13}$—C(O)R$^{14}$" and insert -- —S(O)$_m$R$^{13}$, —C(O)R$^{14}$ --, therefor.

In Column 19, Line 21, delete "—CH$_2$C$_{6-10}$ aryl," and insert -- —CH$_2$C$_{6-10}$aryl, --, therefor.

In Column 19, Line 22, delete "—C$_{6-10}$ aryl" and insert -- —C$_{6-10}$aryl --, therefor.

In Column 20, Line 19, delete "—OC$_{1-8}$ alkyl," and insert -- —OC$_{1-6}$ alkyl, --, therefor.

In Column 20, Line 40, after "R$^{18}$" insert -- is --.

In Column 21, Line 34, after "R$^{18}$" insert -- is --.

In Column 23, Lines 25-27, delete "tert-Butyl (2S)-2-({[(4-bromophenyl)amino]carbonyl}oxy)-3-phenyl propanoate; and" and insert the same in Column 23, Line 26, as a new paragraph.

In Column 23, Line 49, delete "comeal" and insert -- corneal --, therefor.

In Column 23, Line 51, delete "comeal" and insert -- corneal --, therefor.

In Column 24, Line 25, delete "Ukrorgsynth," and insert -- Ukrorgsynthesis, --, therefor.

In Column 25, Line 20, delete "(CD$_3$OD" and insert -- (CD$_3$OD, --, therefor.

CERTIFICATE OF CORRECTION (continued)

In Column 25, Line 29, delete "-2-([[(4-Bromophenyl)carbamoyl]oxy)-" and insert -- -2-{[(4-Bromophenyl)carbamoyl]oxy}- --, therefor.

In Column 26, Line 5, delete "(CD₃OD" and insert -- (CD₃OD, --, therefor.

In Column 34, Line 34, delete "]oxy)}-" and insert -- ]oxy}- --, therefor.

In Column 40, Line 24, delete "rotomers." and insert -- rotamers. --, therefor.

In Column 40, Line 28, delete "(Isopropyl" and insert -- (isopropyl --, therefor.

In Column 40, Line 48, delete "rotomers." and insert -- rotamers. --, therefor.

In Column 40, Line 53, delete "-methybutyl" and insert -- -methylbutyl --, therefor.

In Column 41, Line 3, delete "rotomers." and insert -- rotamers. --, therefor.

In Column 41, Line 27, delete "rotomers." and insert -- rotamers. --, therefor.

In Column 41, Lines 31-32, delete "-({2-[(tert-butoxycarbonyl)amino]ethyl}amino)carbonyl-" and insert -- -[({2-[(tert-butoxycarbonyl)amino]ethyl}amino)carbonyl]- --, therefor.

In Column 43, Line 4, delete "]pentanoyl}propyl" and insert -- ]pentanoyl}(propyl --, therefor.

In Column 43, Line 24, delete "rotomers." and insert -- rotamers. --, therefor.

In Column 43, Line 49, delete "rotomers." and insert -- rotamers. --, therefor.

In Column 44, Line 8, delete "})oxy)-" and insert -- }oxy)- --, therefor.

In Column 44, Lines 55-62, delete " 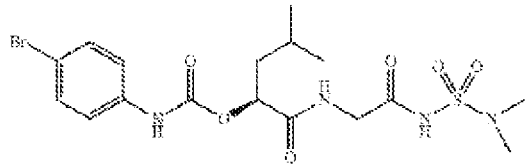 " and insert -- 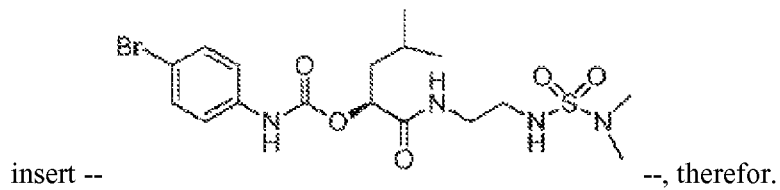 --, therefor.

In Column 44, Line 65, delete "N,N-dimethylsulfomoyl" and insert -- N,N-dimethylsulfamoyl --, therefor.

In Columns 61-62, Line 10 (TABLE 4-continued), delete "methyl pentanoate" and insert -- methylpentanoate --, therefor.

In Column 63, Line 40, in Claim 1, delete "—S(O)$_m$R$^{13}$—C(O)R$^{14}$" and insert -- —S(O)$_m$R$^{13}$, —C(O)R$^{14}$ --, therefor.

In Column 63, Line 48, in Claim 1, delete "(Ch$_2$)$_p$COOH," and insert -- —(CH$_2$)$_p$COOH, --, therefor.

In Column 63, Line 61, in Claim 1, delete "—(CH$_2$)—S(O)$_2$OH," and insert -- —(CH$_2$)$_n$S(O)$_2$OH, --, therefor.

In Column 63, Lines 62-63, in Claim 1, delete "(CH$_2$)$_n$NR$^{18}$R$^{19}$, —(CH$_2$)—P(O)(OC$_{1-6}$ alkyl)$_2$," and insert -- —(CH$_2$)$_n$NR$^{18}$R$^{19}$, —(CH$_2$)$_n$P(O)(OC$_{1-6}$ alkyl)$_2$, --, therefor.

In Column 64, Line 30, in Claim 1, delete "—(CH)$_n$C(O)R$^{17}$" and insert -- —(CH$_2$)$_n$C(O)R$^{17}$ --, therefor.

In Column 64, Line 40, in Claim 1, after "amide," delete "sulfonamide,".

In Column 65, Line 16, in Claim 5, delete "—(CH$_2$)—C(O)R$^{17}$," and insert -- —(CH$_2$)$_n$C(O)R$^{17}$, --, therefor.

In Column 65, Line 17, in Claim 5, delete "—(CH$_2$)—NR$^{18}$R$^{19}$," and insert -- —(CH$_2$)$_n$NR$^{18}$R$^{19}$, --, therefor.

In Column 65, Line 22, in Claim 5, after "R$^{18}$" insert -- is --.

In Column 65, Line 34, in Claim 6, delete "—(CH$_2$)—C(O)R$^{17}$," and insert -- —(CH$_2$)$_n$C(O)R$^{17}$, --, therefor.

In Column 65, Line 40, in Claim 6, after "R$^{18}$" insert -- is --.

In Column 66, Lines 9-16, in Claim 8, delete " 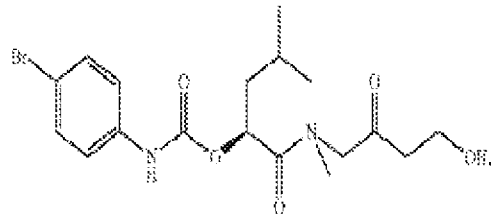 " and insert -- 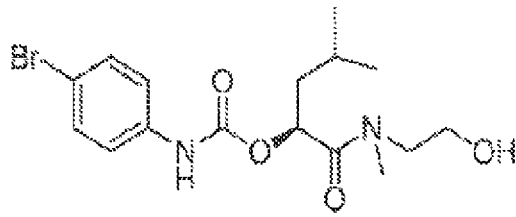 --, therefor.

CERTIFICATE OF CORRECTION (continued)
U.S. Pat. No. 9,926,264 B2

In Column 71, Lines 17-24, in Claim 10, delete " 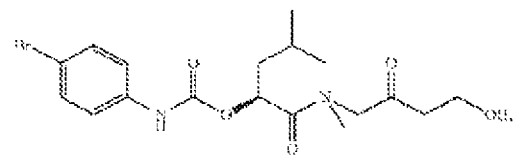 " and insert -- 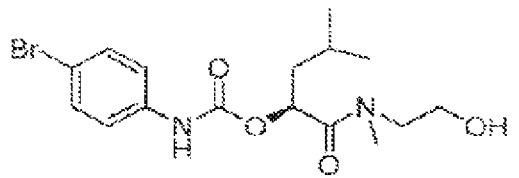 --, therefor.